(12) United States Patent
Que et al.

(10) Patent No.: US 11,898,168 B2
(45) Date of Patent: Feb. 13, 2024

(54) METHODS OF PROMOTING ESOPHAGEAL DIFFERENTIATION OF PLURIPOTENT STEM CELLS

(71) Applicant: The Trustees of Columbia University in the City of New York, New York, NY (US)

(72) Inventors: Jianwen Que, Fort Lee, NJ (US); Yongchun Zhang, Fort Lee, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 1217 days.

(21) Appl. No.: 16/156,401

(22) Filed: Oct. 10, 2018

(65) Prior Publication Data
US 2019/0112579 A1 Apr. 18, 2019

Related U.S. Application Data

(60) Provisional application No. 62/571,555, filed on Oct. 12, 2017.

(51) Int. Cl.
C12N 5/071 (2010.01)
A61K 35/37 (2015.01)

(52) U.S. Cl.
CPC ........... *C12N 5/0679* (2013.01); *A61K 35/37* (2013.01); *C12N 2500/38* (2013.01); *C12N 2500/90* (2013.01); *C12N 2500/99* (2013.01); *C12N 2501/11* (2013.01); *C12N 2501/115* (2013.01); *C12N 2501/119* (2013.01); *C12N 2501/15* (2013.01); *C12N 2501/155* (2013.01); *C12N 2501/16* (2013.01); *C12N 2501/385* (2013.01); *C12N 2501/415* (2013.01); *C12N 2501/727* (2013.01); *C12N 2501/998* (2013.01); *C12N 2501/999* (2013.01); *C12N 2506/02* (2013.01); *C12N 2506/23* (2013.01); *C12N 2506/45* (2013.01); *C12N 2513/00* (2013.01); *C12N 2533/90* (2013.01)

(58) Field of Classification Search
CPC .............. C12N 5/0679; C12N 2500/38; C12N 2500/90; C12N 2500/99; C12N 2501/11; C12N 2501/115; C12N 2501/119; C12N 2501/15; C12N 2501/155; C12N 2501/16; C12N 2501/385; C12N 2501/415; C12N 2501/727; C12N 2501/998; C12N 2501/999; C12N 2506/02; C12N 2506/23; C12N 2506/45; C12N 2513/00; C12N 2533/90; A61K 35/37
See application file for complete search history.

(56) References Cited

PUBLICATIONS

Woo et al., Barx1-mediated inhibition of Wnt signaling in the mouse thoracic foregut controls tracheo-esophageal separation and epithelial differentiation, PLoS ONE, 6(7): 1-8. (Year: 2011).*

Chen et al., Development of small molecules targeting the Wnt pathway for the treatment of colon cancer: a high-throughput screening approach, American Journal of Physiology-Gastrointestinal and Liver Physiology, 299: G292-G300. (Year: 2010).*

Yang et al., The evolving roles of canonical WNT signaling in stem cells and tumorigenesis: implications in targeted cancer therapies, Pathology in Focus, Labratory Investigation, 96: 116-136. (Year: 2016).*

Smith, TGFb inhibitors new and unexpected requirements in vertebrate development, Trends in Genetics, 15(1): 3-5. (Year: 1999).*

Spender et al., Preclinical Evaluation of AZ12601011 and AZ12799734, Inhibitors of Transforming Growth Factor b Superfamily Type 1 Receptors, Molecular Pharmacology, p. 222-234. (Year: 2019).*

Hao et al., Dorsomorphin, a Selective Small Molecule Inhibitor of BMP Signaling, Promotes Cardiomyogenesis in Embryonic Stem Cells, PLoS ONE, 3(8): 1-8. (Year: 2008).*

Niehrs et al., The complex world of WNT receptor signalling, Nature Reviews, 13: 767-779. (Year: 2012).*

Pettinato et al., Scalable Differentiation of Human iPSCs in a Multicellular Spheroid-based 3D Culture into Hepatocyte-like Cells through Direct Wnt/β-catenin Pathway Inhibition, Nature Scientific Reports, 6(32888): 1-16. (Year: 2016).*

Song et al., New insights into the regulation of Axin function in canonical Wnt signaling pathway, Protein Cell, 5(3): 186-193. (Year: 2014).*

Xiao et al., Importance of WNT-dependent signaling for derivation and maintenance of primed pluripotent bovine embryonic stem cells, 105(1): 52-63. (Year: 2021).*

Goumans et al., Functional analysis of the TGFb receptor/Smad pathway through gene ablation in mice, International Journal of Developmental Biology, 44: 253-265. (Year: 2000).*

Trisno et al., Esophageal Organoids from Human Pluripotent Stem Cells Delineate Sox2 Functions during Esophageal Specification, Cell Stem Cell, 23: 501-515. (Year: 2018).*

Barbera et al., (Jan. 2015). The human squamous oesophagus has widespread capacity for clonal expansion from cells at diverse stages of differentiation. *Gut* 64, 11-19.

Blank et al., (Sep. 18, 2008). An in vivo reporter of BMP signaling in organogenesis reveals targets in the developing kidney. *BMC Dev Biol* 8, 86.

(Continued)

*Primary Examiner* — Laura Schuberg
*Assistant Examiner* — Joseph Paul Miano
(74) *Attorney, Agent, or Firm* — Leason Ellis LLP

(57) ABSTRACT

The current invention provides for methods of promoting differentiation of human pluripotent stem cells into esophageal progenitor cells as well as the cells obtained from the methods, solutions, compositions, and pharmaceutical compositions comprising such cells. The current invention also provides for methods of using the esophageal progenitor cells for treatment and prevention of disease, and kits.

16 Claims, 51 Drawing Sheets
(41 of 51 Drawing Sheet(s) Filed in Color)
Specification includes a Sequence Listing.

(56) References Cited

PUBLICATIONS

Brooker et al., (Apr. 2006). Notch ligands with contrasting functions: Jagged1 and Delta1 in the mouse inner ear. *Development* 133, 1277-1286.

Burke, and Oliver, (Oct. 2002). Prox1 is an early specific marker for the developing liver and pancreas in the mammalian foregut endoderm. *Mech Develop* 118, 147-155.

Chang et al., (Nov. 5, 2013). Lung epithelial branching program antagonizes alveolar differentiation. Proc Natl Acad Sci U S A 110, 18042-18051.

Chen et al., (Apr. 24, 2017). A three-dimensional model of human lung development and disease from pluripotent stem cells. *Nat Cell Biol* 19, 542-549.

Dathan et al., (Aug. 2002). Distribution of the titf2/foxe1 gene product is consistent with an important role in the development of foregut endoderm, alate, and hair. *Dev Dyn* 224, 450-456.

De Ward et al., (Oct. 23, 2014). Cellular heterogeneity in the mouse esophagus implicates the presence of a nonquiescent epithelial stem cell population. *Cell Rep* 9, 701-711.

Domyan et al., (Mar. 2011). Signaling through BMP receptors promotes respiratory identity in the foregut via repression of Sox2. *Development* 138, 971-981.

Giroux et al., (Jun. 1, 2017). Long-lived keratin 15+ esophageal progenitor cells contribute to homeostasis and regeneration. *J Clin Invest* 127, 2378-2391.

Goldstein et al., (Jun. 2007). Overexpression of Kruppel-like factor 5 in esophageal epithelia in vivo leads to increased proliferation in basal but not suprabasal cells. *Am J Physiol Gastrointest Liver Physiol* 292, G1784-1792.

Goss et al., (Aug. 2009). Wnt2/2b and beta-catenin signaling are necessary and sufficient to specify lung progenitors in the foregut. *Dev Cell* 17, 290-298.

Han et al., (Jun. 2002). Inducible gene knockout of transcription factor recombination signal binding protein-J reveals its essential role in T versus B lineage decision. *Int Immunol* 14, 637-645.

Harfe et al., (Aug. 20, 2004). Evidence for an expansion-based temporal Shh gradient in specifying vertebrate digit identities. *Cell* 118, 517-528.

Harris-Johnson et al., (Sep. 22, 2009). beta-Catenin promotes respiratory progenitor identity in mouse foregut. *Proc Natl Acad Sci U S A* 106, 16287-16292.

Hawkins et al., (Jun. 1, 2017). Prospective isolation of NKX2-1-expressing human lung progenitors derived from pluripotent stem cells. *J Clin Invest* 127, 2277-2294.

Huang et al., (Mar. 2015). The in vitro generation of lung and airway progenitor cells from human pluripotent stem cells. *Nat Protoc* 10, 413-425.

Huang et al., (Jan. 2014). Efficient generation of lung and airway epithelial cells from human pluripotent stem cells. *Nat Biotechnol* 32, 84-91.

Jacobs et al., (Sep. 1, 2012). Genetic and cellular mechanisms regulating anterior foregut and esophageal development. *Dev Biol* 369, 54-64.

Jiang et al., (Mar. 16, 2015). BMP-driven NRF2 activation in esophageal basal cell differentiation and eosinophilic esophagitis. *J Clin Invest* 125, 1557-1568.

Jiang et al., (Oct. 26, 2017). Transitional basal cells at the squamous-columnar junction generate Barrett's oesophagus. Nature Accepted.

Kalabis et al., (Dec. 1, 2008). A subpopulation of mouse esophageal basal cells has properties of stem cells with the capacity for self-renewal and lineage specification. *J Clin Invest* 118, 3860-3869.

Kalabis et al., (Jan. 12, 2012). Isolation and characterization of mouse and human esophageal epithelial cells in 3D organotypic culture. *Nat Protoc* 7, 235-246.

Kopan and Ilagan (Apr. 17, 2009). The canonical Notch signaling pathway: unfolding the activation mechanism. *Cell* 137, 216-233.

Liu et al., (2013). Sox2 cooperates with inflammation-mediated Stat3 activation in the malignant transformation of foregut basal progenitor cells. *Cell Stem Cell* 12, 304-315.

Longmire et al., (Mar. 7, 2012). Efficient derivation of purified lung and thyroid progenitors from embryonic stem cells. *Cell Stem Cell* 10, 398-411.

McCauley et al., (Jun. 1, 2017). Efficient Derivation of Functional Human Airway Epithelium from Pluripotent Stem Cells via Temporal Regulation of Wnt Signaling. *Cell Stem Cell* 20, 844-857 e846.

McCracken et al., (Dec. 18, 2014). Modelling human development and disease in pluripotent stem-cell-derived gastric organoids. *Nature* 516, 400-404.

McMahon et al., (May 15, 1998). Noggin-mediated antagonism of BMP signaling is required for growth and patterning of the neural tube and somite. *Genes Dev* 12, 1438-1452.

Minoo et al., (May 1, 1999). Defects in tracheoesophageal and lung morphogenesis in Nkx2.1(−/−) mouse embryos. *Dev Biol* 209, 60-71.

Mori et al., (Jan. 15, 2015). Notch3-Jagged signaling controls the pool of undifferentiated airway progenitors. *Development* 142, 258-267.

Mou et al., (Aug. 4, 2016). Dual SMAD Signaling Inhibition Enables Long-Term Expansion of Diverse Epithelial Basal Cells. *Cell Stem Cell* 19, 217-231.

Mou et al., (Apr. 6, 2012). Generation of multipotent lung and airway progenitors from mouse ESCs and patient-specific cystic fibrosis iPSCs. *Cell Stem Cell* 10, 385-397.

Okano et al., (May 4, 2000). The Kruppel-like transcriptional factors Zf9 and GKLF coactivate the human keratin 4 promoter and physically interact. *FEBS Lett* 473, 95-100.

Pagliuca et al., (Oct. 9, 2014). Generation of functional human pancreatic beta cells in vitro. *Cell* 159, 428-439.

Peters et al., (Sep. 1, 1998). Pax9-deficient mice lack pharyngeal pouch derivatives and teeth and exhibit craniofacial and limb abnormalities. *Genes Dev* 12, 2735-2747.

Piazzolla et al., (Jun. 30, 2014). Lineage-restricted function of the pluripotency factor NANOG in stratified epithelia. *Nat Commun* 5, 4226.

Que, (Jul.-Aug. 2015). The initial establishment and epithelial morphogenesis of the esophagus: a new model of tracheal-esophageal separation and transition of simple columnar into stratified squamous epithelium in the developing esophagus. *Wiley Interdiscip Rev Dev Biol* 4, 419-430.

Que et al., (Jun. 1, 2009). Multiple roles for Sox2 in the developing and adult mouse trachea. *Development* 136, 1899-1907.

Que et al., (Jul. 2007). Multiple dose-dependent roles for Sox2 in the patterning and differentiation of anterior foregut endoderm. *Development* 134, 2521-2531.

Rockich et al., (Nov. 19, 2013). Sox9 plays multiple roles in the lung epithelium during branching morphogenesis. *Proc Natl Acad Sci U S A* 110, E4456-4464.

Rodriguez et al., (Dec. 2010). BMP signaling in the development of the mouse esophagus and forestomach. *Development* 137, 4171-4176.

Roost et al., (Jun. 9, 2015). KeyGenes, a Tool to Probe Tissue Differentiation Using a Human Fetal Transcriptional Atlas. *Stem Cell Rep* 4, 1112-1124.

Shi et al., (May 4, 2017). Genome Editing in hPSCs Reveals GATA6 Haploinsufficiency and a Genetic Interaction with GATA4 in Human Pancreatic Development. *Cell Stem Cell* 20, 675-688 e676.

Song et al., (Aug. 1, 2014). Hippo coactivator YAP1 upregulates SOX9 and endows esophageal cancer cells with stem-like properties. *Cancer Res* 74, 4170-4182.

Spence et al., (Aug. 1, 2011). Directed differentiation of human pluripotent stem cells into intestinal tissue in vitro. *Nature* 470, 105-U120.

Trounson and DeWitt, (Mar. 2016). Pluripotent stem cells progressing to the clinic. *Nat Rev Mol Cell Biol* 17, 194-200.

Tsao et al., (Jul. 19, 2016). Epithelial Notch signaling regulates lung alveolar morphogenesis and airway epithelial integrity. *Proc Natl Acad Sci USA* 113, 8242-8247.

Tetreault et al., (May 17, 2016). KLF4 transcriptionally activates non-canonical WNT5A to control epithelial stratification. *Sci Rep* 6, 26130.

(56) References Cited

PUBLICATIONS

Wang et al., (Sep. 2014). Hedgehog signaling regulates FOXA2 in esophageal embryogenesis and Barrett's metaplasia. *J Clin Invest* 124, 3767-3780.

Wang et al., (Jun. 24, 2011). Residual embryonic cells as precursors of a Barrett's-like metaplasia. *Cell* 145, 1023-1035.

Wang et al., (Sep. 15, 2006). Retinoic acid regulates morphogenesis and patterning of posterior foregut derivatives. *Dev Biol* 297, 433-445.

Wells et al., (Jan. 12, 2007). Wnt/beta-catenin signaling is required for development of the exocrine pancreas. *Bmc Developmental Biology* 7.

Wong et al., (Sep. 2012). Directed differentiation of human pluripotent stem cells into mature airway epithelia expressing functional CFTR protein. *Nature Biotechnology* 30, 876-U108.

Xu et al., (Jun. 2010). Generation of mice with a conditional null allele of the Jagged2 gene. *Genesis* 48, 390-393.

Yu et al., (Aug. 1, 2005). Conversion of columnar to stratified squamous epithelium in the developing mouse esophagus. *Dev Biol* 284, 157-170.

Zhang et al., (Jun. 2017). Development and stem cells of the esophagus. *Semin Cell Dev Biol* 66, 25-35.

Yiangou et al., (Apr. 5, 2018). Human Pluripotent Stem Cell-Derived Endoderm for Modeling Development and Clinical Applications. *Cell Stem Cell* 22 485-499.

Jacob et al., (Oct. 5, 2017). Differentiation of Human Pluripotent Stem Cells into Functional Lung Alveolar Epithelial Cells. *Cell Stem Cell* 21 472-488.

Green et al. (Mar. 2011). Generation of anterior foregut endoderm from human embryonic and induced pluripotent stem cells. *Nature Biotechnology* vol. 29, No. 3 267-273

Ober et al., (Aug. 10, 2006). Mesodermal Wnt2b signaling positively regulates liver specification. *Nature* 442, 688-691.

Que et al., (Sep. 2006). Morphogenesis of the trachea and esophagus: current players and new roles for noggin and Bmps. *Differentiation* 74, 422-437.

Liu et al., (Mar. 7, 2013). Sox2 cooperates with inflammation-mediated Stat3 activation in the malignant transformation of foregut basal progenitor cells. *Cell Stem Cell* 12, 304-315.

\* cited by examiner

Figure 1B

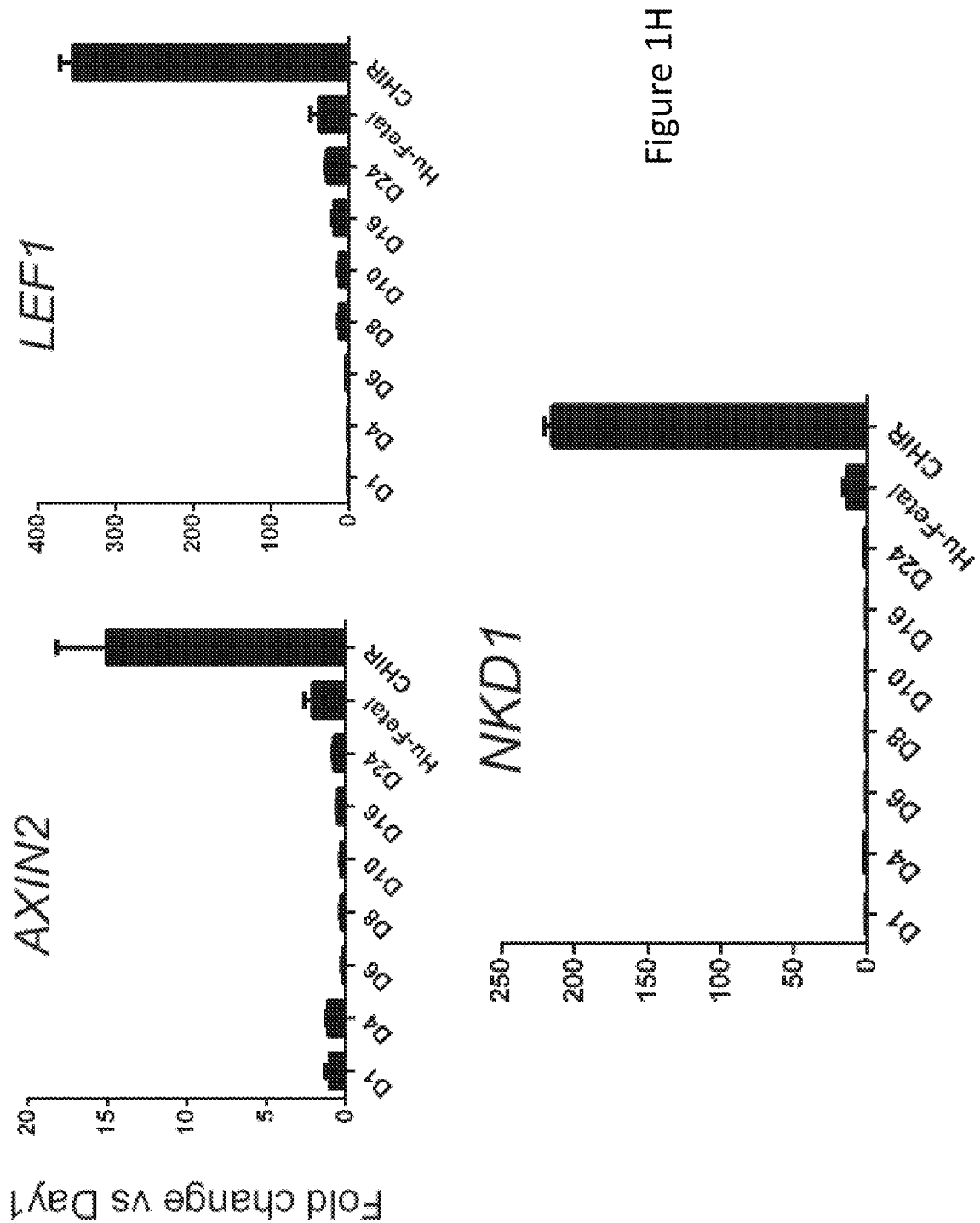

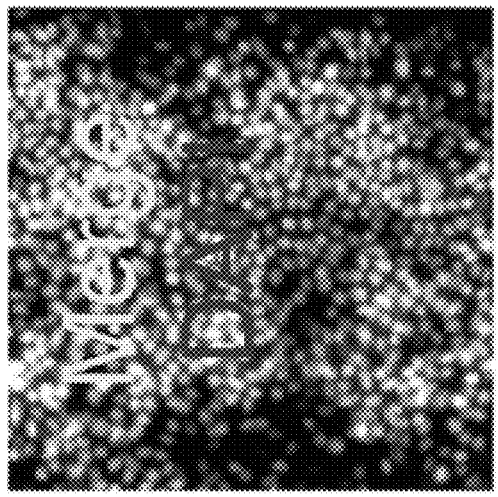
Figure 3C
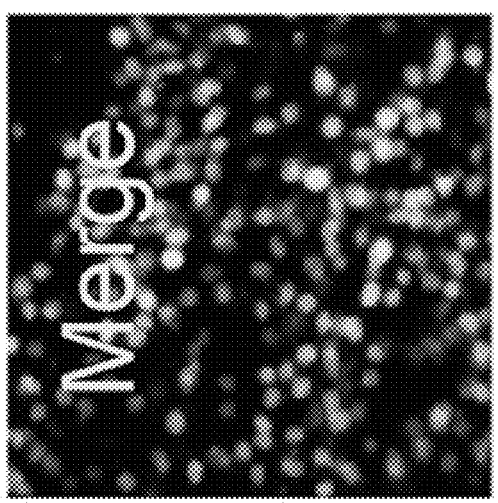
Figure 3D
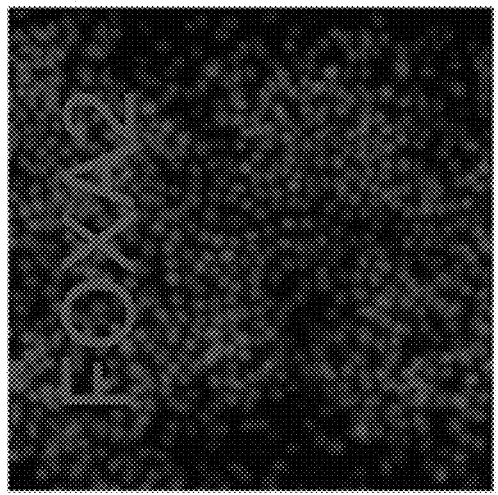
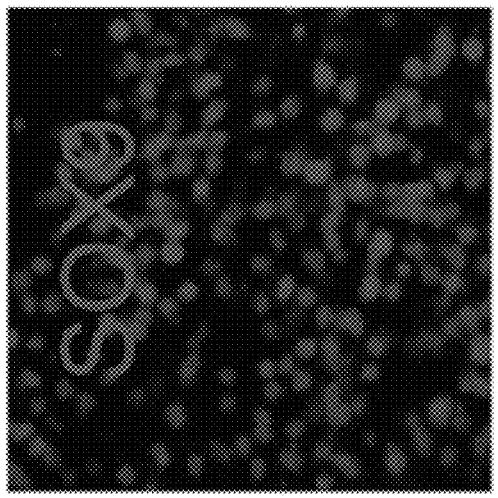
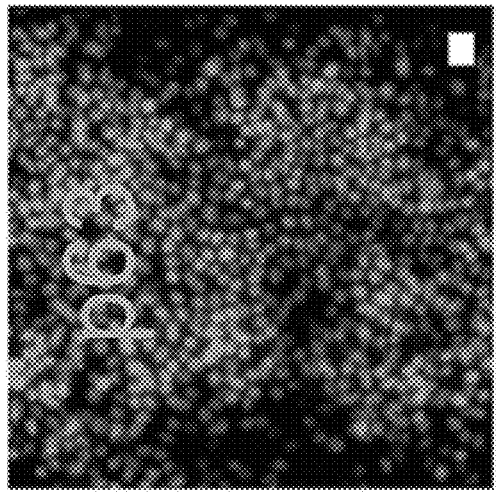
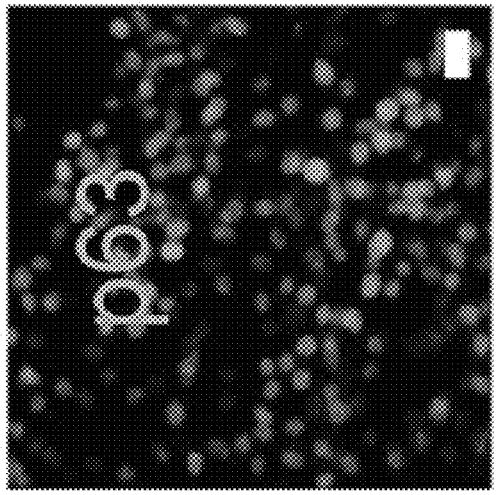

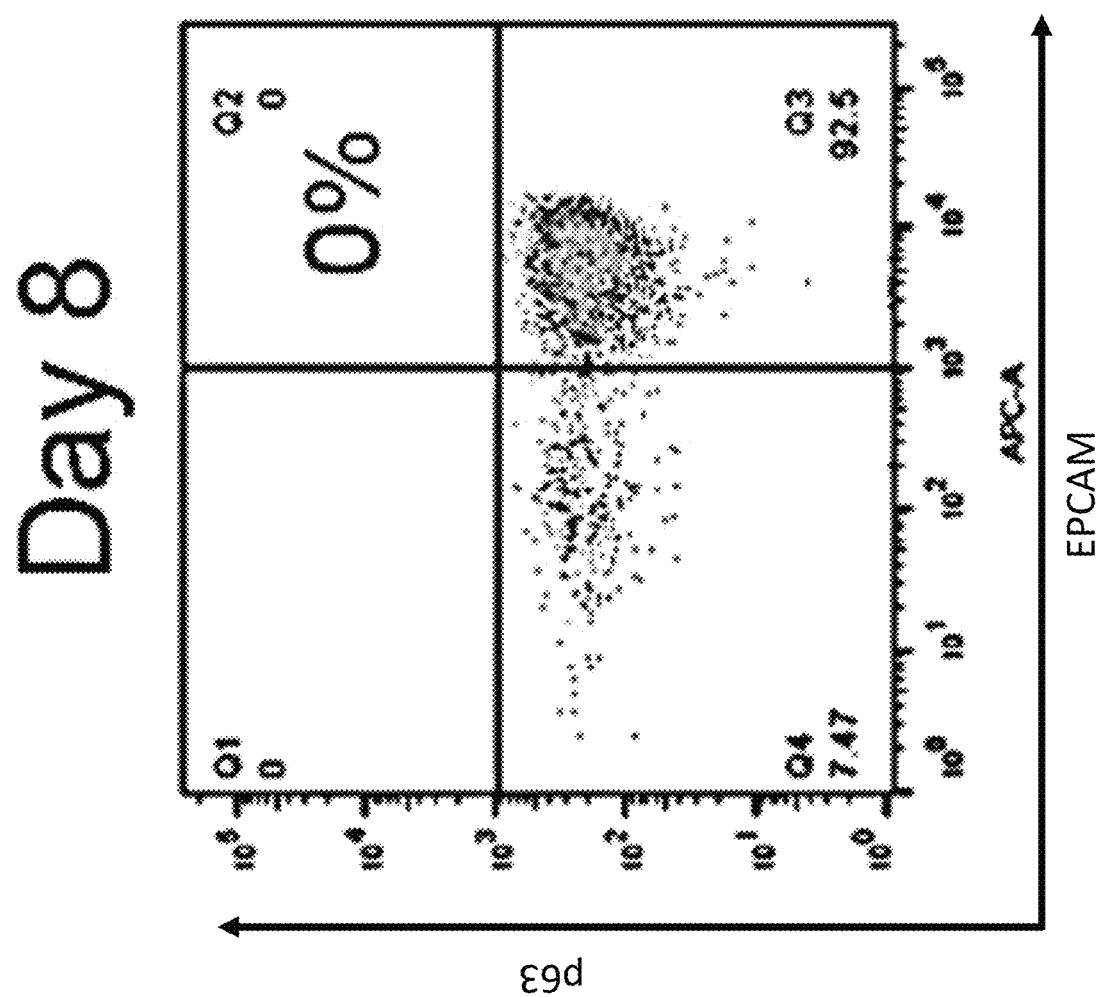

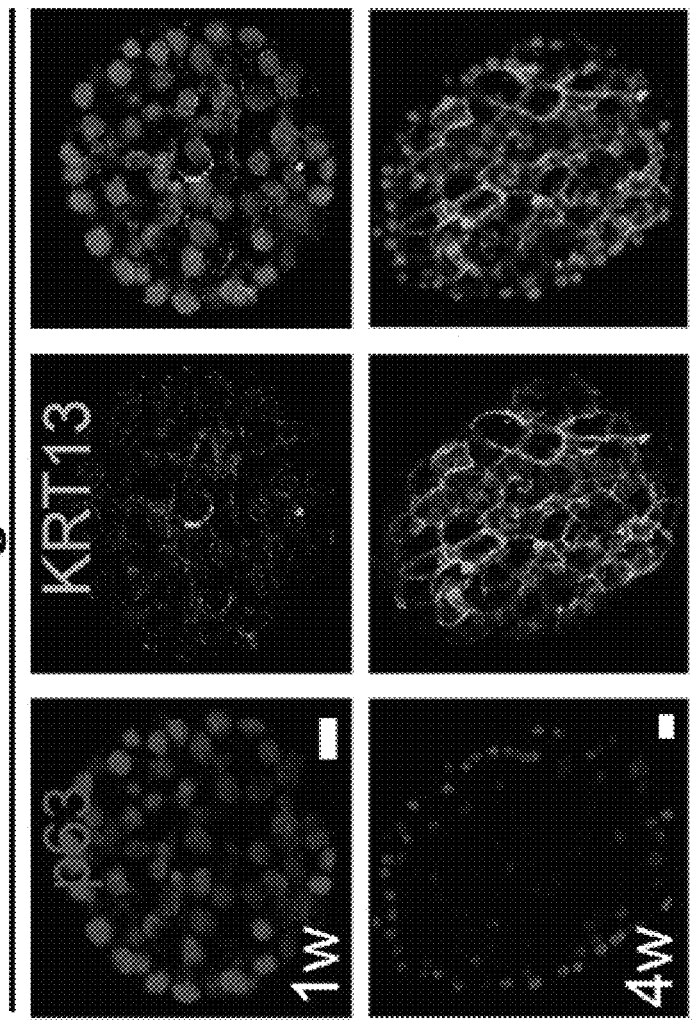
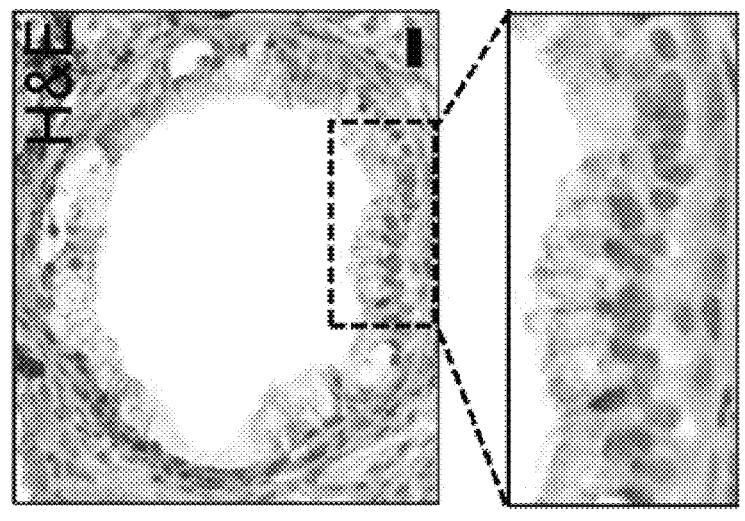
Figure 5D
Figure 5E

SEQUENCE LISTING

<160> NUMBER OF SEQ ID NOS: 68

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
ttcggacagt acaaagaacg g                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2
gcatttcata agtctcacgg c                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
caggacacca tgaggaacag                                                20

<210> SEQ ID NO 4
<211> LENGTH: 18
<212> TYPE: DNA
<213> ORGANISM: Artificial Sequence
<220> FEATURE:
<223> OTHER INFORMATION: Synthetic Primer

<400> SEQUENCE: 4
tcatgttcat gccgctcg                                                  18

<210> SEQ ID NO 5
<211> LENGTH: 17
<212> TYPE: DNA
<213> ORGANISM: Artificial Sequence
<220> FEATURE:
<223> OTHER INFORMATION: Synthetic Primer

<400> SEQUENCE: 5
cacactgccc ctctcac                                                   17

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
tccatgctgt ttcttactct cc                                             22

<210> SEQ ID NO 7
<211> LENGTH: 20
<212> TYPE: DNA
<213> ORGANISM: Artificial Sequence

```
<220> FEATURE:
<223> OTHER INFORMATION: Synthetic Primer

<400> SEQUENCE: 7 gaaataccte agcctccagc                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
gcgtcacacc attgctattc                                          20

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer

<400> SEQUENCE: 9
ctggtcgttt gttgtggc                                            18

<210> SEQ ID NO 10
<211> LENGTH: 19
<212> TYPE: DNA
<213> ORGANISM: Artificial Sequence
<220> FEATURE:
<223> OTHER INFORMATION: Synthetic Primer

<400> SEQUENCE: 10
ttcatgttgc tcacggagg                                           19

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
agggctggat ggttgtattg                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
tgagttcatg ttgctgaccg                                          20

<210> SEQ ID NO 13
<211> LENGTH: 17
<212> TYPE: DNA
<213> ORGANISM: Artificial Sequence
<220> FEATURE:
<223> OTHER INFORMATION: Synthetic Primer

<400> SEQUENCE: 13
acttgcacaa cgccgag                                             17
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic Primer

<400> SEQUENCE: 14
ctggtacttg taatccgggt g                                              21

<210> SEQ ID NO 15
<211> LENGTH: 19
<212> TYPE: DNA
<213> ORGANISM: Artificial Sequence
<220> FEATURE:
<223> OTHER INFORMATION: Synthetic Primer

<400> SEQUENCE: 15
ggtgaacggg ttggagaag                                                 19

<210> SEQ ID NO 16
<211> LENGTH: 19
<212> TYPE: DNA
<213> ORGANISM: Artificial Sequence
<220> FEATURE:
<223> OTHER INFORMATION: Synthetic Primer

<400> SEQUENCE: 16
ggtgaacggg ttggagaag                                                 19

<210> SEQ ID NO 17
<211> LENGTH: 21
<212> TYPE: DNA
<213> ORGANISM: Artificial Sequence
<220> FEATURE:
<223> OTHER INFORMATION: Synthetic Primer

<400> SEQUENCE: 17
agctagatac cttgggcaat g                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
cacaaagtca ttctcggctg                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
cacaaagtca ttctcggctg                                                20

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer
```

```
<400> SEQUENCE: 20
agctccacct tgttcatgta g                                              21

<210> SEQ ID NO 21
<211> LENGTH: 18
<212> TYPE: DNA
<213> ORGANISM: Artificial Sequence
<220> FEATURE:
<223> OTHER INFORMATION: Synthetic Primer

<400> SEQUENCE: 21
caggatatgg cacggcag                                                  18

<210> SEQ ID NO 22
<211> LENGTH: 21
<212> TYPE: DNA
<213> ORGANISM: Artificial Sequence
<220> FEATURE:
<223> OTHER INFORMATION: Synthetic Primer

<400> SEQUENCE: 22
cacagagata ttcacggctc c                                              21

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
aagaccattg aagagctccg                                                20

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
tggcattgtc aatctccagg                                                20

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer

<400> SEQUENCE: 25
gaagtgaaga tccgtgactg g                                              21

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
gcagaaggac attggcattg                                                20

<210> SEQ ID NO 27
```

<210> SEQ ID NO 27
<211> LENGTH: 19
<212> TYPE: DNA
<213> ORGANISM: Artificial Sequence
<220> FEATURE:
<223> OTHER INFORMATION: Synthetic Primer

<400> SEQUENCE: 27
ctgcctcagc cttactgtg                                            19

<210> SEQ ID NO 28
<211> LENGTH: 21
<212> TYPE: DNA
<213> ORGANISM: Artificial Sequence
<220> FEATURE:
<223> OTHER INFORMATION: Synthetic Primer

<400> SEQUENCE: 28
gctcctgatg ggtattgact g                                         21

<210> SEQ ID NO 29
<211> LENGTH: 18
<212> TYPE: DNA
<213> ORGANISM: Artificial Sequence
<220> FEATURE:
<223> OTHER INFORMATION: Synthetic Primer

<400> SEQUENCE: 29
gagcctgcta caaccctg                                             18

<210> SEQ ID NO 30
<211> LENGTH: 22
<212> TYPE: DNA
<213> ORGANISM: Artificial Sequence
<220> FEATURE:
<223> OTHER INFORMATION: Synthetic Primer

<400> SEQUENCE: 30
tgtgtctatg agttttcgtc cc                                        22

<210> SEQ ID NO 31
<211> LENGTH: 21
<212> TYPE: DNA
<213> ORGANISM: Artificial Sequence
<220> FEATURE:
<223> OTHER INFORMATION: Synthetic Primer

<400> SEQUENCE: 31
ggactatgag ggcaagaact g                                         21

<210> SEQ ID NO 32
<211> LENGTH: 21
<212> TYPE: DNA
<213> ORGANISM: Artificial Sequence
<220> FEATURE:
<223> OTHER INFORMATION: Synthetic Primer

<400> SEQUENCE: 32
aaatataccg caccccttca g                                         21

<210> SEQ ID NO 33
<211> LENGTH: 21
<212> TYPE: DNA
<213> ORGANISM: Artificial Sequence
<220> FEATURE:
<223> OTHER INFORMATION: Synthetic Primer

<400> SEQUENCE: 33

```
aaatataccg caccccttca g                                              21

<210> SEQ ID NO 34
<211> LENGTH: 19
<212> TYPE: DNA
<213> ORGANISM: Artificial Sequence
<220> FEATURE:
<223> OTHER INFORMATION: Synthetic Primer

<400> SEQUENCE: 34
cagacaaggc ttccatccg                                                 19

<210> SEQ ID NO 35
<211> LENGTH: 20
<212> TYPE: DNA
<213> ORGANISM: Artificial Sequence
<220> FEATURE:
<223> OTHER INFORMATION: Synthetic Primer

<400> SEQUENCE: 35
ctacctgaag cacagcaaag                                                20

<210> SEQ ID NO 36
<211> LENGTH: 18
<212> TYPE: DNA
<213> ORGANISM: Artificial Sequence
<220> FEATURE:
<223> OTHER INFORMATION: Synthetic Primer

<400> SEQUENCE: 36
agcttcatct gcgtgtcg                                                  18

<210> SEQ ID NO 37
<211> LENGTH: 20
<212> TYPE: DNA
<213> ORGANISM: Artificial Sequence
<220> FEATURE:
<223> OTHER INFORMATION: Synthetic Primer

<400> SEQUENCE: 37
tggtacccag tgcttttgag                                                20

<210> SEQ ID NO 38
<211> LENGTH: 21
<212> TYPE: DNA
<213> ORGANISM: Artificial Sequence
<220> FEATURE:
<223> OTHER INFORMATION: Synthetic Primer

<400> SEQUENCE: 38
ctccgatagt ccatagcaag g                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic Primer

<400> SEQUENCE: 39
ctccgatagt ccatagcaag g                                              21

<210> SEQ ID NO 40
<211> LENGTH: 23
<212> TYPE: DNA
```

```
<213> ORGANISM: Artificial Sequence
<220> FEATURE:
<223> OTHER INFORMATION: Synthetic Primer

<400> SEQUENCE: 40
gcatcttcaa atgatccact gtc                                          23

<210> SEQ ID NO 41
<211> LENGTH: 20
<212> TYPE: DNA
<213> ORGANISM: Artificial Sequence
<220> FEATURE:
<223> OTHER INFORMATION: Synthetic Primer

<400> SEQUENCE: 41
tgtccagcaa aactctgagg                                              20

<210> SEQ ID NO 42
<211> LENGTH: 23
<212> TYPE: DNA
<213> ORGANISM: Artificial Sequence
<220> FEATURE:
<223> OTHER INFORMATION: Synthetic Primer

<400> SEQUENCE: 42
gcatcttcaa atgatccact gtc                                          23

<210> SEQ ID NO 43
<211> LENGTH: 21
<212> TYPE: DNA
<213> ORGANISM: Artificial Sequence
<220> FEATURE:
<223> OTHER INFORMATION: Synthetic Primer

<400> SEQUENCE: 43
tgtcactgtc ttgtaccctt g                                            21

<210> SEQ ID NO 44
<211> LENGTH: 19
<212> TYPE: DNA
<213> ORGANISM: Artificial Sequence
<220> FEATURE:
<223> OTHER INFORMATION: Synthetic Primer

<400> SEQUENCE: 44
ggcgtttgga gtggtagaa                                               19

<210> SEQ ID NO 45
<211> LENGTH: 21
<212> TYPE: DNA
<213> ORGANISM: Artificial Sequence
<220> FEATURE:
<223> OTHER INFORMATION: Synthetic Primer

<400> SEQUENCE: 45
cccctggaaa gaatggagat g                                            21

<210> SEQ ID NO 46
<211> LENGTH: 21
<212> TYPE: DNA
<213> ORGANISM: Artificial Sequence
<220> FEATURE:
<223> OTHER INFORMATION: Synthetic Primer

<400> SEQUENCE: 46
tccaaaccac tgaaacctct g                                            21
```

<210> SEQ ID NO 47
<211> LENGTH: 19
<212> TYPE: DNA
<213> ORGANISM: Artificial Sequence
<220> FEATURE:
<223> OTHER INFORMATION: Synthetic Primer

<400> SEQUENCE: 47
gaggatgtgg aagtggctg                                                19

<210> SEQ ID NO 48
<211> LENGTH: 21
<212> TYPE: DNA
<213> ORGANISM: Artificial Sequence
<220> FEATURE:
<223> OTHER INFORMATION: Synthetic Primer

<400> SEQUENCE: 48
acatctgtga agaccaacct g                                             21

<210> SEQ ID NO 49
<211> LENGTH: 18
<212> TYPE: DNA
<213> ORGANISM: Artificial Sequence
<220> FEATURE:
<223> OTHER INFORMATION: Synthetic Primer

<400> SEQUENCE: 49
ggacacgcct tctgaacg                                                 18

<210> SEQ ID NO 50
<211> LENGTH: 21
<212> TYPE: DNA
<213> ORGANISM: Artificial Sequence
<220> FEATURE:
<223> OTHER INFORMATION: Synthetic Primer

<400> SEQUENCE: 50
agaagggaat tcagaagcct g                                             21

<210> SEQ ID NO 51
<211> LENGTH: 18
<212> TYPE: DNA
<213> ORGANISM: Artificial Sequence
<220> FEATURE:
<223> OTHER INFORMATION: Synthetic Primer

<400> SEQUENCE: 51
ggacacgcct tctgaacg                                                 18

<210> SEQ ID NO 52
<211> LENGTH: 19
<212> TYPE: DNA
<213> ORGANISM: Artificial Sequence
<220> FEATURE:
<223> OTHER INFORMATION: Synthetic Primer

<400> SEQUENCE: 52
cggagtccag tgtggtttg                                                19

<210> SEQ ID NO 53
<211> LENGTH: 22
<212> TYPE: DNA
<213> ORGANISM: Artificial Sequence
<220> FEATURE:

<223> OTHER INFORMATION: Synthetic Primer

<400> SEQUENCE: 53
acctacacaa agagttccca tc                                          22

<210> SEQ ID NO 54
<211> LENGTH: 20
<212> TYPE: DNA
<213> ORGANISM: Artificial Sequence
<220> FEATURE:
<223> OTHER INFORMATION: Synthetic Primer

<400> SEQUENCE: 54
tgtgtttacg gtagtgcctg                                             20

<210> SEQ ID NO 55
<211> LENGTH: 21
<212> TYPE: DNA
<213> ORGANISM: Artificial Sequence
<220> FEATURE:
<223> OTHER INFORMATION: Synthetic Primer

<400> SEQUENCE: 55
gaaggagtaa ccccgatttg g                                           21

<210> SEQ ID NO 56
<211> LENGTH: 22
<212> TYPE: DNA
<213> ORGANISM: Artificial Sequence
<220> FEATURE:
<223> OTHER INFORMATION: Synthetic Primer

<400> SEQUENCE: 56
cttcccaggt acacttgtat gg                                          22

<210> SEQ ID NO 57
<211> LENGTH: 21
<212> TYPE: DNA
<213> ORGANISM: Artificial Sequence
<220> FEATURE:
<223> OTHER INFORMATION: Synthetic Primer

<400> SEQUENCE: 57
agacaagcac aaacctctca g                                           21

<210> SEQ ID NO 58
<211> LENGTH: 24
<212> TYPE: DNA
<213> ORGANISM: Artificial Sequence
<220> FEATURE:
<223> OTHER INFORMATION: Synthetic Primer

<400> SEQUENCE: 58
tcattatgta cccggaataa ctcg                                        24

<210> SEQ ID NO 59
<211> LENGTH: 21
<212> TYPE: DNA
<213> ORGANISM: Artificial Sequence
<220> FEATURE:
<223> OTHER INFORMATION: Synthetic Primer

<400> SEQUENCE: 59
ctcgccggga tagaaaacta c                                           21

-continued

```
<210> SEQ ID NO 60
<211> LENGTH: 18
<212> TYPE: DNA
<213> ORGANISM: Artificial Sequence
<220> FEATURE:
<223> OTHER INFORMATION: Synthetic Primer

<400> SEQUENCE: 60
ggtgtgggat gtggatgg                                                 18

<210> SEQ ID NO 61
<211> LENGTH: 20
<212> TYPE: DNA
<213> ORGANISM: Artificial Sequence
<220> FEATURE:
<223> OTHER INFORMATION: Synthetic Primer

<400> SEQUENCE: 61
gttaagttta cggccaacgg                                               20

<210> SEQ ID NO 62
<211> LENGTH: 19
<212> TYPE: DNA
<213> ORGANISM: Artificial Sequence
<220> FEATURE:
<223> OTHER INFORMATION: Synthetic Primer

<400> SEQUENCE: 62
accttctcca ctagtcccc                                                19

<210> SEQ ID NO 63
<211> LENGTH: 23
<212> TYPE: DNA
<213> ORGANISM: Artificial Sequence
<220> FEATURE:
<223> OTHER INFORMATION: Synthetic Primer

<400> SEQUENCE: 63
ttttataccc gttatcccag ctc                                           23

<210> SEQ ID NO 64
<211> LENGTH: 22
<212> TYPE: DNA
<213> ORGANISM: Artificial Sequence
<220> FEATURE:
<223> OTHER INFORMATION: Synthetic Primer

<400> SEQUENCE: 64
tgcgtacttc tccatctgaa tg                                            22

<210> SEQ ID NO 65
<211> LENGTH: 21
<212> TYPE: DNA
<213> ORGANISM: Artificial Sequence
<220> FEATURE:
<223> OTHER INFORMATION: Synthetic Primer

<400> SEQUENCE: 65
gtctacacag tctttgctcc c                                             21

<210> SEQ ID NO 66
<211> LENGTH: 21
<212> TYPE: DNA
<213> ORGANISM: Artificial Sequence
<220> FEATURE:
<223> OTHER INFORMATION: Synthetic Primer
```

```
<400> SEQUENCE: 66
tccgctaacc aggatttcat c                                              21

<210> SEQ ID NO 67
<211> LENGTH: 21
<212> TYPE: DNA
<213> ORGANISM: Artificial Sequence
<220> FEATURE:
<223> OTHER INFORMATION: Synthetic Primer

<400> SEQUENCE: 67
tcgcccaggt tgtaattgaa g                                              21

<210> SEQ ID NO 68
<211> LENGTH: 20
<212> TYPE: DNA
<213> ORGANISM: Artificial Sequence
<220> FEATURE:
<223> OTHER INFORMATION: Synthetic Primer

<400> SEQUENCE: 68
tgagaaagtc ctgccagttg                                                20
```

METHODS OF PROMOTING ESOPHAGEAL DIFFERENTIATION OF PLURIPOTENT STEM CELLS

CROSS REFERENCE TO RELATED APPLICATION

The present application claims priority to U.S. patent application Ser. No. 62/571,555 filed Oct. 12, 2017, which is hereby incorporated by reference in its entirety.

STATEMENT OF GOVERNMENT SUPPORT

This invention was made with government support under grant numbers DK100342, HL132996, and DK113144 awarded by the National Institutes of Health. The government has certain rights in this invention.

FIELD OF THE INVENTION

The current invention provides for methods of promoting differentiation of pluripotent stem cells, including human, into esophageal progenitor cells as well as the cells obtained from the methods, solutions, compositions, and pharmaceutical compositions comprising such cells. The current invention also provides for methods of using the esophageal progenitor cells for treatment and prevention of disease, and kits.

BACKGROUND OF THE INVENTION

Differentiation of human pluripotent stem cells (hPSCs) including embryonic stem cells (ESCs) and induced pluripotent stem cells (iPSCs) has offered new approaches to directly study human organ development and disease mechanisms (Huang et al., 2014; Longmire et al., 2012; McCracken et al., 2014; Mou et al., 2012; Pagliuca et al., 2014). In addition, these hPSC-derived cells hold the potential to provide unlimited sources for clinical uses and pharmacological applications (Trounson and DeWitt, 2016). Generation of lineage-specific progenitor cells from hPSCs leverages the knowledge of signaling mechanisms obtained from studying other species mostly mice. Multiple signaling pathways such as WNT and BMP have been shown to play essential roles in the development of different organs including the lung and esophagus (Domyan et al., 2011; Goss et al., 2009; Harris-Johnson et al., 2009; Que et al., 2006). Much of this knowledge has now been utilized to successfully promote the differentiation of hPSCs into various cell lineages in tissues like the lung and thyroid where the same epithelial types are shared among rodents and humans (Huang et al., 2014; Longmire et al., 2012). By contrast, for the esophagus where the epithelial structure is distinct between rodents (keratinized) and humans (non-keratinized), it is unknown whether the developmental mechanisms are conserved. Consequently, thus far derivation of esophageal epithelium from hPSCs has not been successful.

The esophagus is established from the dorsal side of the anterior foregut endoderm (AFE) at around 4 weeks of development in humans and embryonic (E) 9.5 in mice. By contrast, the ventral foregut endoderm gives rise to the thyroid, lung and trachea (Jacobs et al., 2012; Que, 2015). Studies of mouse genetic models have shown that establishment of these foregut organs involves a dorsal-ventral patterning of transcription factors and signaling pathways (Que, 2015). For example, the transcription factors NKX2.1 and SOX2 are preferentially expressed in the ventral and dorsal side of the AFE, respectively (Que et al., 2006; Que et al., 2009; Que et al., 2007). Disruption of Nkx2.1 or Sox2 gene expression leads to abnormal formation of the lung and esophagus (Que et al., 2007). Furthermore, BMP and WNT signaling are preferentially activated in the ventral foregut, and disruption of the signaling pathways also leads to abnormal lung specification and agenesis (Domyan et al., 2011; Goss et al., 2009; Harris-Johnson et al., 2009; Que et al., 2006). Accordingly, activation of the WNT pathway using the GSK3β inhibitor CHIR99021 is instrumental for coaxing the differentiation of hPSCs towards lung epithelium (Huang et al., 2015; Huang et al., 2014). The inventors have previously shown that the BMP inhibitor Noggin is enriched in the dorsal side of the early foregut. Deletion of the Nog gene leads to failed separation of the esophagus from the foregut, resulting in birth defects, such as esophageal atresia with tracheoesophageal fistula (EA/TEF) (Que et al., 2006). Further studies showed that Noggin-mediated inhibition of BMP signaling continues to play important roles for epithelial morphogenesis in the developing esophagus. Nog deletion results in failed conversion of simple columnar cell into stratified squamous epithelium and the esophagus becomes lined by a mucin-producing glandular epithelium (Rodriguez et al., 2010). Moreover, recent studies suggested that BMP inhibition is required for the maintenance of basal cells, progenitor cells of the stratified squamous epithelium in the esophagus (Jiang et al., 2015).

As stated above, there are several distinct characteristics between the mouse and human esophagus. For example, similar to the skin, the mouse esophageal epithelium is keratinized in contrast to the non-keratinized human esophagus (Jacobs et al., 2012). Therefore, it remains unknown whether the activities of the relevant signaling pathways (e.g. BMP) is similarly involved in the specification of human esophageal epithelium. It is also unknown whether other signaling pathway(s) are required for epithelial morphogenesis.

Because of this, to date there is no efficient method for obtain esophageal progenitor cells from human pluripotent stem cells (hPSCs) or induced pluripotent stem cells (iPSCs).

SUMMARY OF THE INVENTION

Shown herein is an efficient method to induce differentiation of human pluripotent stem cells (hPSCs) including embryonic stem cells (ESCs) and induced pluripotent stem cells (iPSCs) towards esophageal progenitor cells (EPCs). These EPCs can be further purified with the cell surface markers EPCAM and ITGβ4. Also shown herein is that the hPSC-derived EPCs are able to recapitulate human esophageal developmental processes and reconstitute the stratified squamous epithelium in three-dimensional (3D) organoids and kidney capsule xenografts. Notably, using a combination of hPSC differentiation and mouse genetics a conserved role for NOTCH signaling in esophageal development in human and mice was identified.

One embodiment of the present invention is a method of inducing differentiation of human pluripotent stem cells (hPSCs) including embryonic stem cells (ESCs) and induced pluripotent stem cells (iPSCs) towards esophageal progenitor cells (EPCs) including the steps of:

1. differentiating stem cells into endoderm cells;
2. culturing the resulting endoderm cells and differentiating the endoderm cells into anterior foregut cells by contacting or incubating the endoderm cells with an agent which inhibits BMP and an agent which inhibits TGFβ signaling and optionally contacting or incubating the cells with an agent which inhibits TGFβ signaling and an agent which inhibits WNT/β-catenin;

3. further culturing the resulting anterior foregut cells and differentiating the resulting anterior foregut cells into esophageal progenitor cells by contacting or incubating the endoderm cells with an agent which inhibits BMP and an agent which inhibits TGFβ signaling; and 4. culturing the cells in serum-free differentiation medium to further allow differentiation into EPCs.

A further embodiment of the present invention is a method of obtaining esophageal progenitor cells (EPCs) from human pluripotent stem cells (hPSCs) including embryonic stem cells (ESCs) and induced pluripotent stem cells (iPSCs). The method includes the following steps:

1. differentiating stem cells into endoderm cells;

2. culturing the resulting endoderm cells and differentiating the endoderm cells into anterior foregut cells by contacting or incubating the endoderm cells with an agent which inhibits BMP and an agent which inhibits TGFβ signaling and optionally contacting or incubating the cells with an agent which inhibits TGFβ signaling and an agent which inhibits WNT/f3-catenin;

3. further culturing the resulting anterior foregut cells and differentiating the resulting anterior foregut cells into esophageal progenitor cells by contacting or incubating the endoderm cells with an agent which inhibits BMP and an agent which inhibits TGFβ signaling; and 4. culturing the cells in serum-free differentiation medium to further allow differentiation into EPCs.

In some embodiments, the contacting or incubating of the cells with the various agents is accomplished by culturing the cells in media comprising the agents.

The method of the invention further provides for purifying or isolating the EPCs obtained from the steps set forth above using novel cell surface markers found to be expressed by the EPCs. Thus, the invention provides for the method with the further step of purifying or isolating the EPCs obtained from steps above by using cell surface markers EPCAM+ and ITGb4+. This step can be done using any method known in the art to purify or isolate such cells.

The current invention also provides for cells obtained using the methods of the invention, solutions, compositions, and pharmaceutical compositions comprising the cells obtained using the methods of the invention.

All of the foregoing embodiments including cells, solutions, compositions, and pharmaceutical compositions comprising the cells can be used to treat and/or prevent disease.

In yet additional embodiments, the invention relates to kits for practicing the methods of the invention and to obtain the cells, solutions, compositions, and pharmaceutical compositions of the invention. The invention also includes kits comprising the cells. solutions, compositions, and pharmaceutical compositions of the invention.

As described herein, the methods, systems and kits are suitable for the large-scale, reproducible production of esophageal epithelial progenitor cells.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

The patent or application file contains at least one drawing executed in color. Copies of this patent or patent application publication with color drawing(s) will be provided by the Office upon request and payment of the necessary fee.

Abbreviations used in the Figure: Abbreviation: D, day; Eso, esophagus; Tra, trachea; NOG, Noggin; SB, SB431542; SFD, serum free medium; N.S., not significant.

Figures 1, 1A:
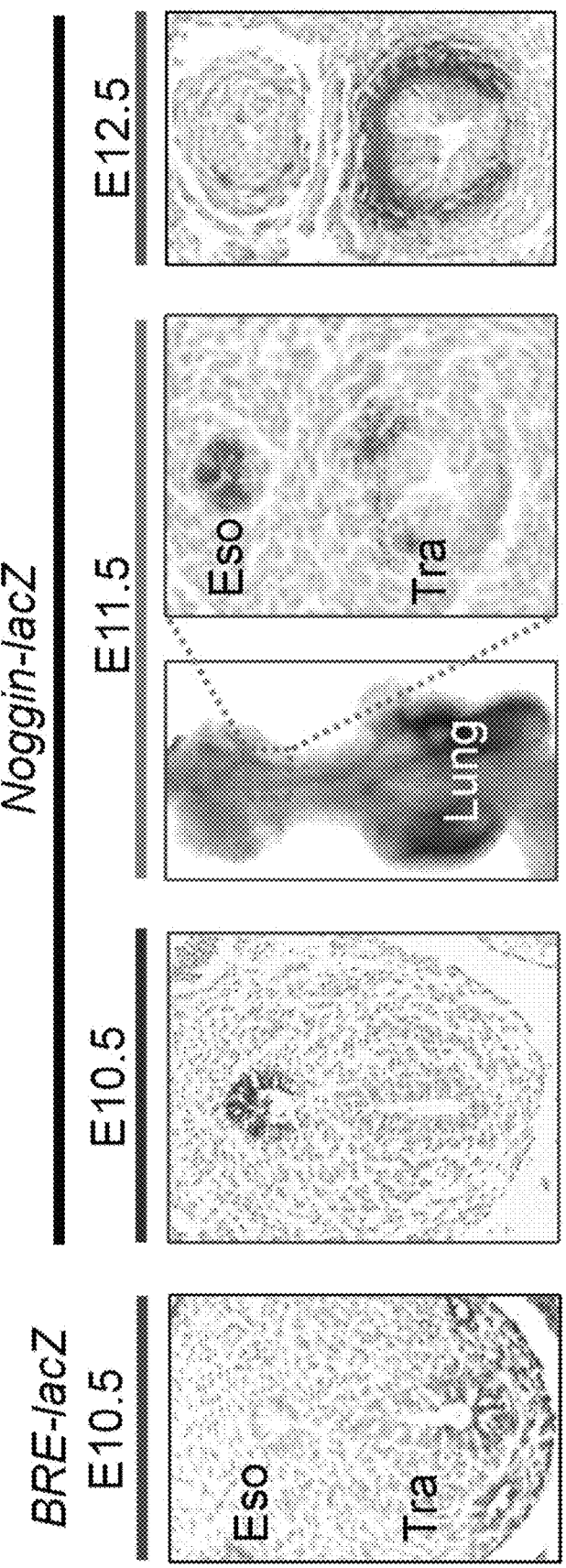
Figure 1B:
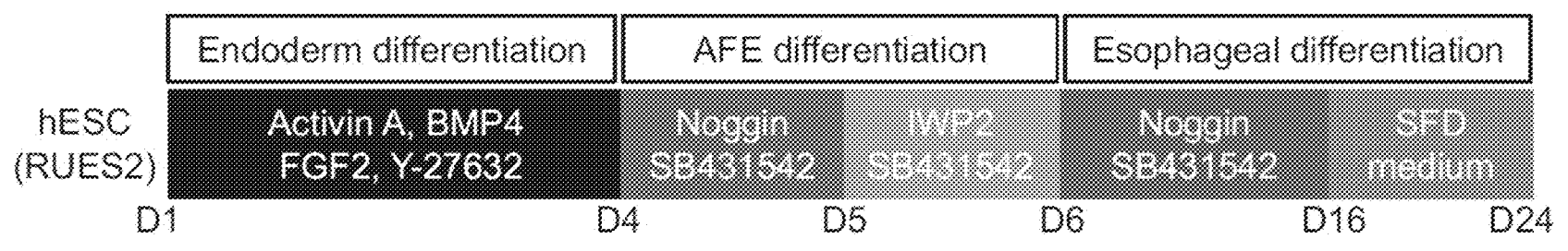
Figure 1C:
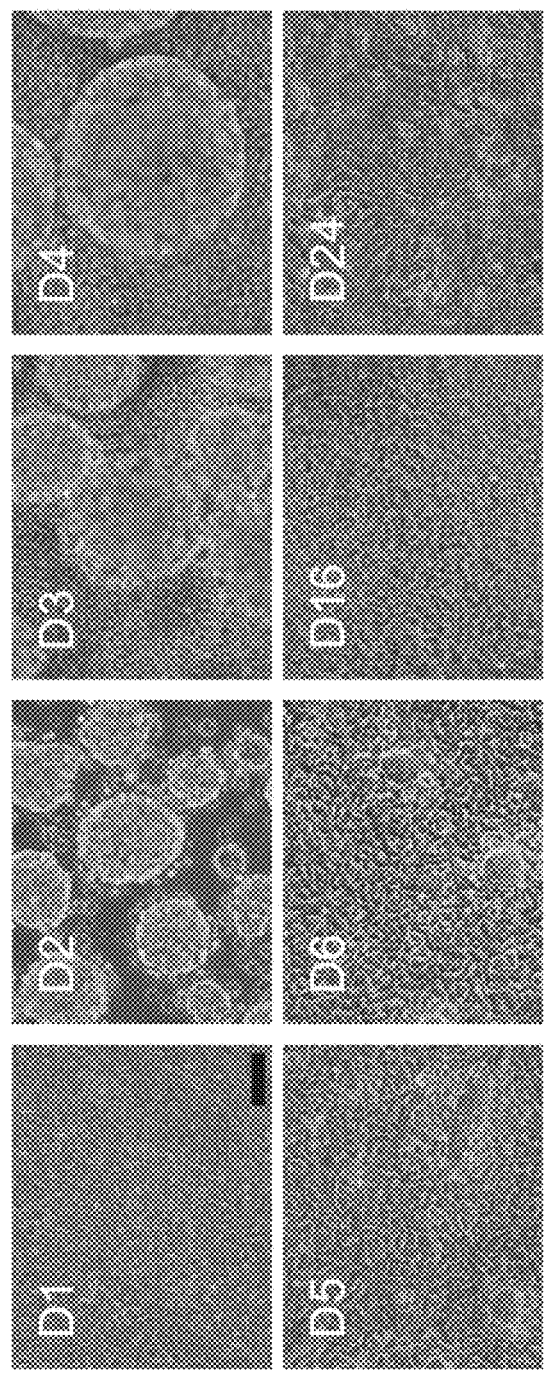
Figure 1D:
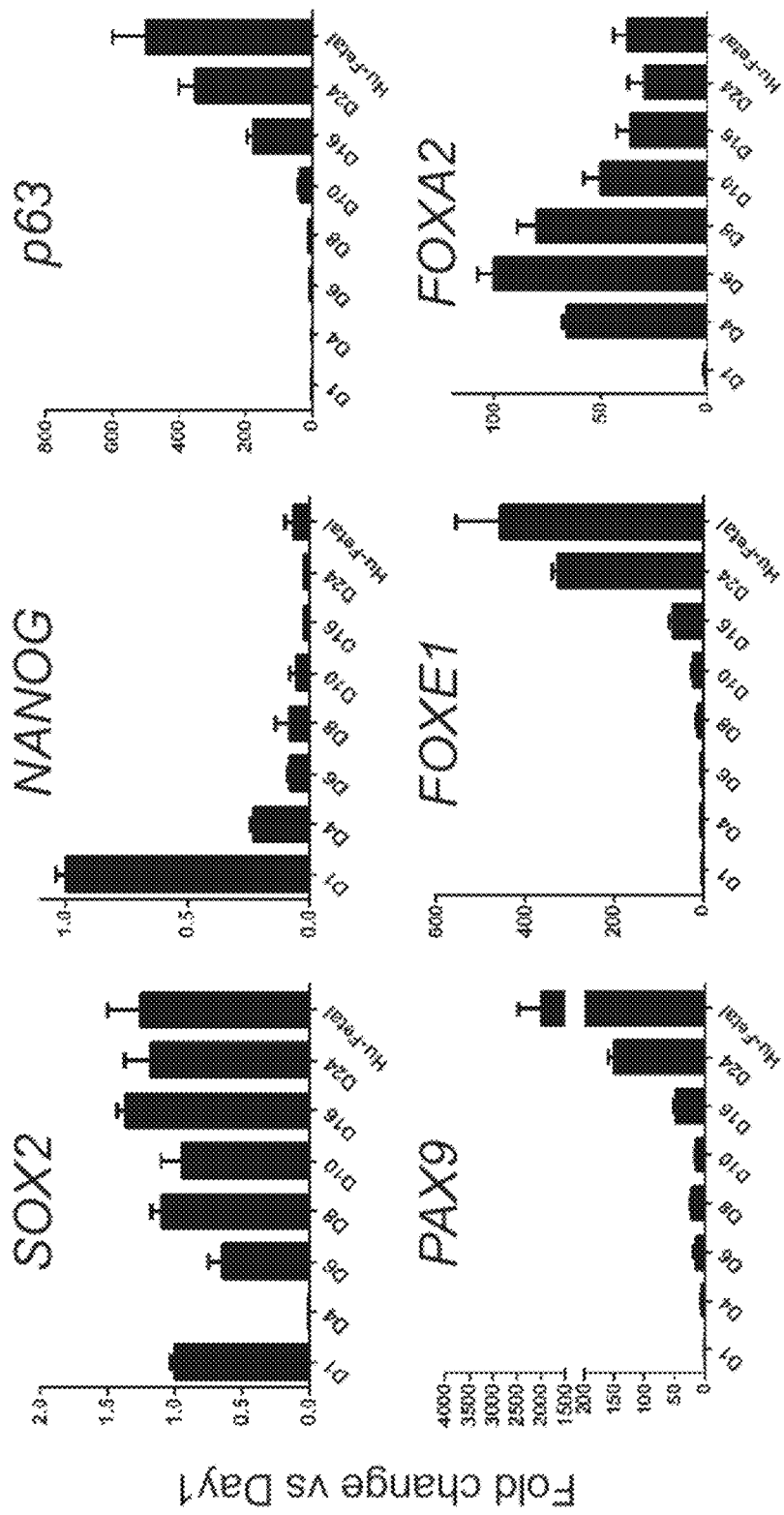
Figure 1E:
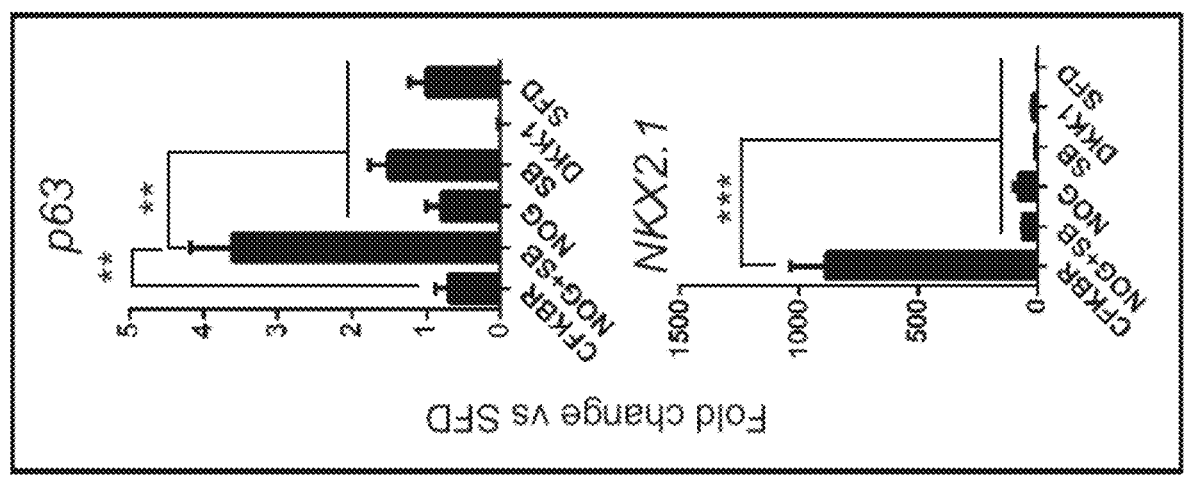
Figure 1F:
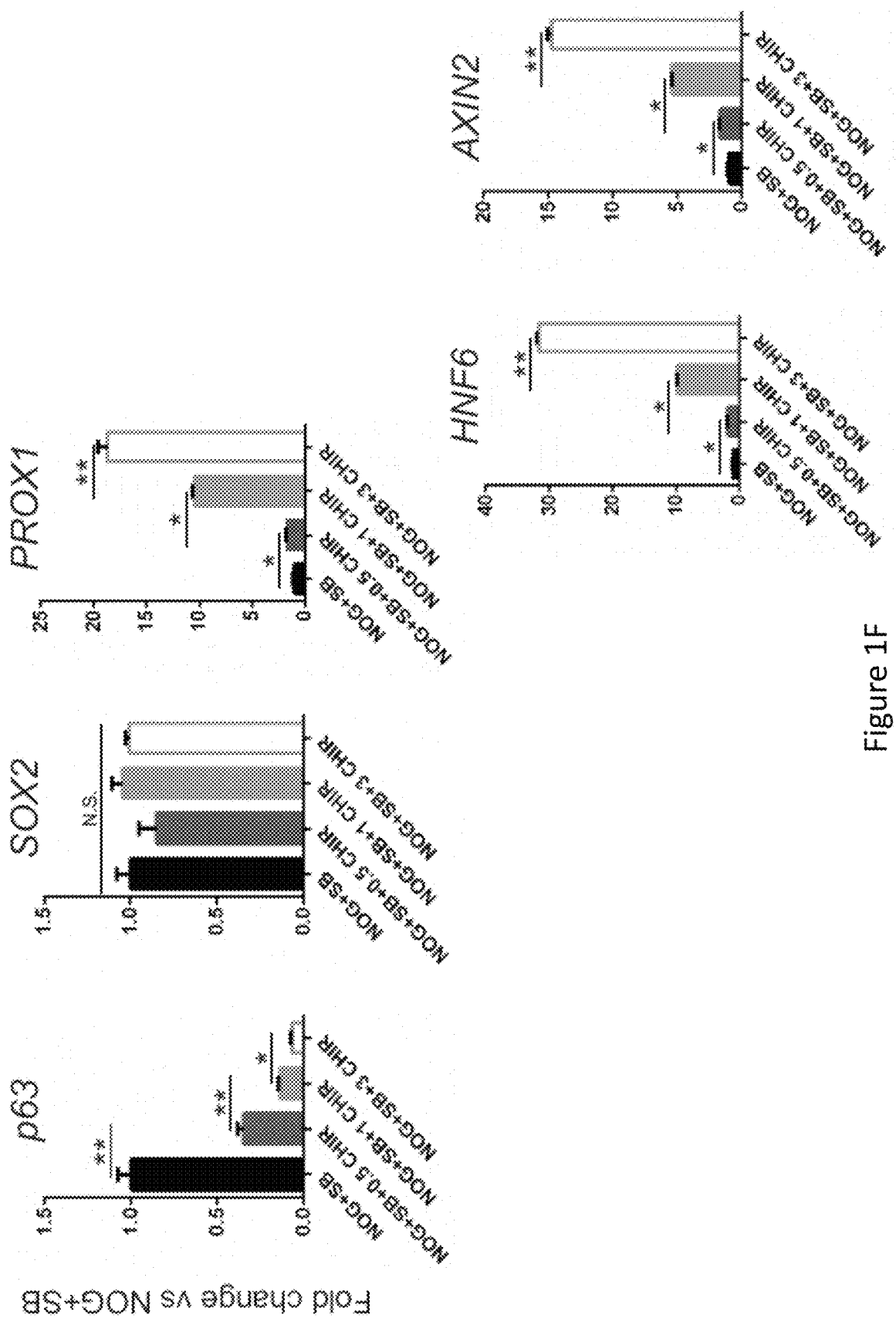
Figure 1G:
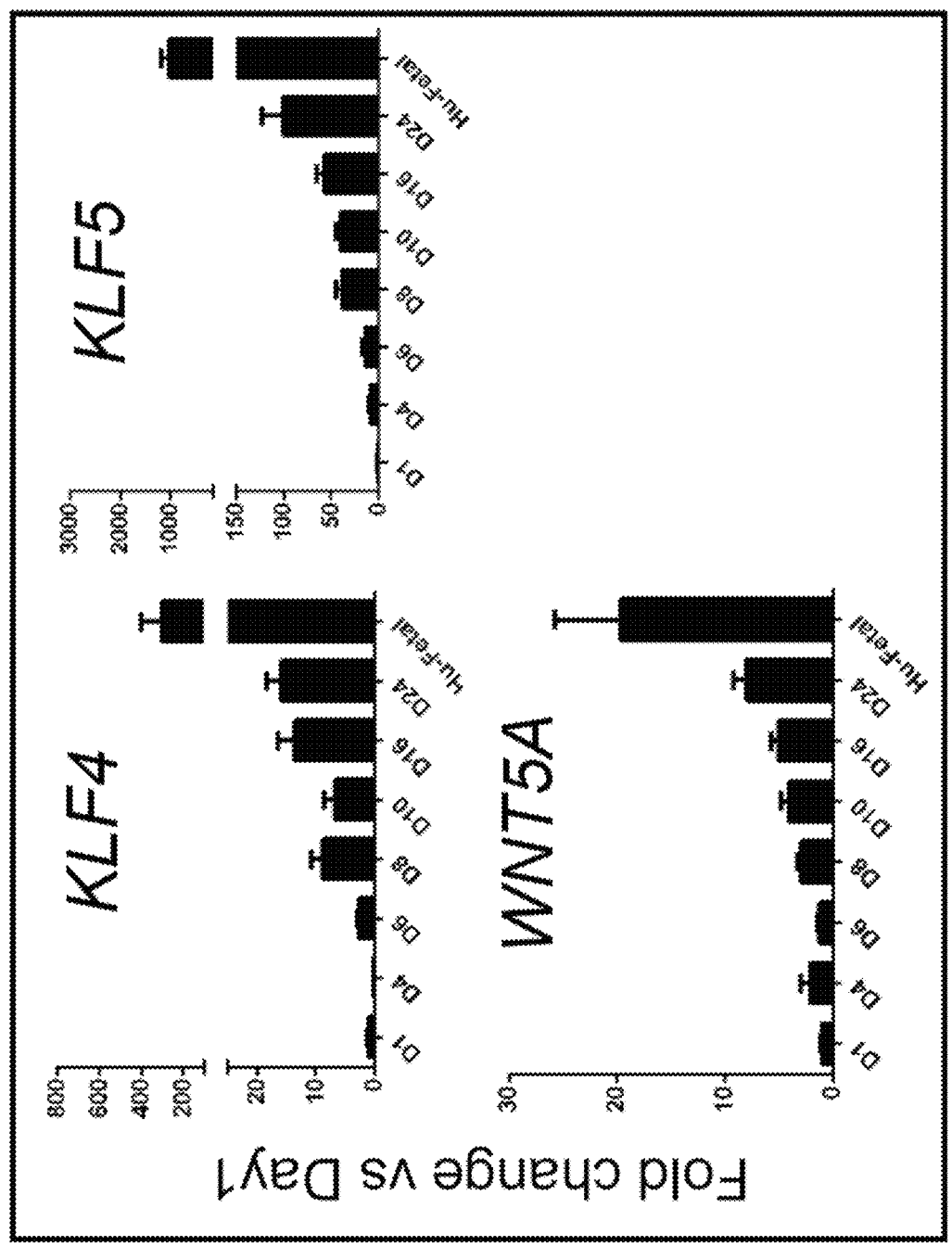
Figure 1I:
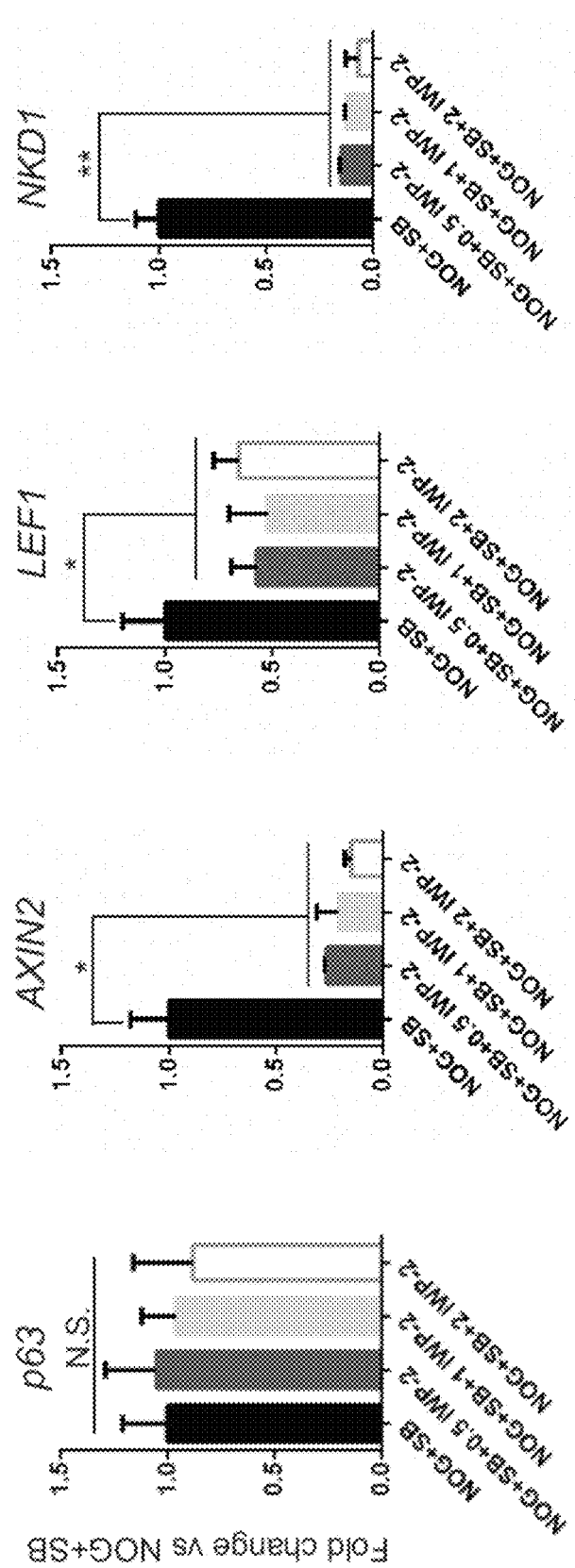

FIG. 1 shows the derivation of esophageal progenitor cells (EPCs) from human embryonic stem cells (hESCs) by inhibiting TGFβ and BMP signaling. FIG. 1A shows images of Noggin-mediated inhibition of BMP signaling in mouse esophageal progenitor cells from a BRE-lacZ transgenic reporter mouse line at E10.5, E11.5 and E12.5. BMP signaling is active in the E10.5 ventral foregut as indicated by the BMP signaling reporter BRE-lacZ. Nog-lacZ is expressed in the dorsal foregut epithelium (esophageal progenitors), and the expression is maintained at E11.5 but lost at E12.5. Note the expression of Nog-lacZ in the tracheal mesenchyme at E11.5 and E12.5. FIG. 1B shows an exemplified protocol for the generation of EPCs from the human ES cell line RUES2. FIG. 1C are images of the cells at D1, D2, D3, D4, D5, D6, D16, and D24 of differentiation from human ES cells to EPCs. FIG. 1D is a graph showing the gene expression of EPC proteins p63, PAX9, FOXE1, NANOG, SOX2 and FOXA2 during hESC differentiation. The transcript levels were normalized to the levels of corresponding genes at day 1. Human fetal esophagus (Hu-Fetal) was included as a control. FIG. 1E shows levels of p63 and NKX2.1 in cells treated with Noggin (NOG) and 10 mM SB431542 (SB) alone or with a GSK3 inhibitor CHIR99021 (3 mM) or with DKK. FIG. 1F are graphs of levels of p63, AXIN2, PROX1, HNF6 and SOX2 as determined by qPCR and reported as fold change compared to NOG+SB with various agents added to the culture. FIG. 1G are graphs of the expression of the esophageal markers KLF4, KLF5 and WNT5A during EPC differentiation. Human fetal esophagus (Hu-Fetal) was included as control. The transcript levels were represented by the fold change compared to day 1 (D1) hESC. FIG. 1H are graphs of the expression of the WNT signaling downstream targets AXIN2, LEF1 and NKD1 during EPC differentiation. Human fetal esophagus (Hu-Fetal) was included as control. hESC RUES2-derived AFE cells treated with 3 μM CHIR (day 6-16) was included as a positive control. The transcript levels were represented by the fold change compared to day 1 (D1) hESC. FIG. 1I are graphs showing WNT inhibition by IWP2 does not affect esophageal specification. RUES2-derived AFE cells were treated with Noggin (NOG) plus S9431542 (SB) in combination with 0.5, 1 or 2 μM IWP2 from day 6 to day 16. Gene expression was determined at day 16. The transcript levels of were represented by the fold change compared to NOG+SB. Data represent mean±SEM (n=3). *p<0.05, **p<0.01 by unpaired, two-tailed Student's t test.

FIG. 2 shows that human ESC-derived EPCs express embryonic esophageal markers. FIG. 2A are images of hESC RUES2-derived EPCs immunostained for p63, FOXA1 and SOX2. FIG. 2B are images of hESC RUES2-derived EPCs immunostained for p63 and FOXA2. FIG. 2C are images of hESC RUES2-derived EPCs immunostained for p63 and PAX9. FIG. 2D are images of hESC RUES2-derived EPCs immunostained for p63 and FOXE1. FIG. 2E are images of E11.5 mouse esophagus cells immunostained for p63, FOXA1, SOX2, and NKX2. FIG. 2F are images of images of 10-week human fetal esophagus cells immunostained for p63, FOXA1, FOXA2, SOX2, PAX9, and FOXE1. FIG. 2G are images of hESC RUES2-derived EPCs and lung progenitor cells immunostained for p63 and NKX2.1 FIG. 2H are images of hESC RUES2-derived EPCs, E11.5 mouse esophagus cell, 10-week human fetal esophagus cells, adult human esophagus cells, and adult mouse esophagus cells immunostained for p63 and SOX9 as well as a graph of the amount of SOX9 in EPCs at day 1 through day 24 and human fetal esophagus cells as control. FIG. 2I are images of hESC-derived EPCs immunostained for p63 and KRT7 and p63 and KRT5. FIG. 2J are E11.5 mouse esophagus cells and adult mouse esophagus cells immunostained for p63 and KRT7. FIG. 2K are images of 10-week human fetal esophagus cells, E18.5 mouse esophagus cells, and adult mouse esophagus cells immunostained for p63 and KRT5. FIG. 2L is a representative tile scan image of EPCs (p63+ SOX2+) derived from the hESC H9 cell line. The EPCs from hESC H9 co-express p63 and SOX2. EPCs were examined at day 24 of differentiation. Scale bars: 20 μm.

FIG. 3 shows the derivation of esophageal epithelial progenitor cells from induced human pluripotent stem cells (iPSCs). FIG. 3A is the schematic diagram depicting the differentiation of EPCs from a human iPS cell line sviPS. FIG. 3B are graphs of the expression of p63, SOX9, FOXE1, KRT5, KRT5, KRT13, INV, and NANOG during the commitment of iPSCs towards EPCs with human fetal esophagus (HU-Fetal) as control. The transcript levels are represented by fold change compared to day 1 (D1). FIG. 3C are images of iPSC-derived EPCs immunostained for p63 and FOXA2. FIG. 3D are images of iPSC-derived EPCs immunostained for p63 and SOX9. FIG. 3E are images of iPSC-derived EPCs immunostained for p63 and NKX2.1 and lung progenitor cells immunostained for NKX2.1. FIG. 3F is a representative tile image for SviPSC iPSC derived EPCs immunostained for p63 and SOX2. Scale bars: 20 μm. FIG. 3G is a representative tile image for mRNA iPSC-derived EPCs for immunostained p53 and SOX2 (scale bar: 100 μm).

FIG. 4 shows the purification of hESC-derived EPCs with the cell surface markers EPCAM and ITGβ4. FIG. 4A are images of day 24 culture containing a mixture of epithelium (EPCAM+) and non-epithelium (EPCAM−) cells. Note that most of the EPCAM+ cells are also p63+. FIG. 4B are human fetal esophagus epithelium stained for EPCAM and p63 and ITGβ4 and p63 at 10 weeks. FIG. 4C shows FACS analysis and graphical representation of RUES2 differentiated cells from day 6 to day 24 showing the gradual increase of p63+ EPCAM+ cells. Data represent mean±SEM (n=3). *p<0.05, **p<0.01 by unpaired, two-tailed Student's t test. Note that a minor population (3.9%) of p63+ cells began to appear at day 10. FIG. 4D shows immunostaining, FACS analysis and graphical representation of hESC-derived EPCs further purified with the combined use of EPCAM and ITGβ4. FIG. 4E is FACS of H9 hESC differentiation at day 24. FIG. 4F is FACS of sviPSC differentiation at day 24. FIG. 4G is FACS of mRNA iPSC at day 24. FIG. 4H are images of organoids formed from the gradual expansion from a single hESC-derived EPCs that were sorted with EPCAM and ITGβ4. Scale bars: 20 μm.

FIG. 5 shows that hPSC-derived EPCs reconstitute the stratified squamous epithelium, mimicking human esophageal development. FIG. 5A are images of differentiating EPCs immuonostained for KRT4 and KRT13 and Loricrin. FIG. 5B are images of reconstituted stratified squamous epithelium in air-liquid interface (ALI) culture of EPCAM+ ITGβ4+ EPCs. Note the conversion of simple layer of epithelium to stratified squamous epithelium with basal cells (p63+) and suprabasal cells (KRT13+). FIG. 5C are images of 10-week human fetal esophagus immunostained for p63 and KRT13. Note epithelial cells in the center of the sphere lose p63 expression while gaining KRT13. FIG. 5D are images showing that hPSC-derived EPCs in a 3D organoid culture. FIG. 5E are images of the hPSC-derived EPCs forming tubular structure lined by a mixture of simple columnar and stratified epithelium upon transplantation into the mouse kidney capsule for 30 days (n=3). FIG. 5F are images of the hPSC-derived EPCs forming tubular structure lined by a mixture of simple columnar and stratified epithelium upon transplantation into the mouse kidney capsule for 30 days (n=3). Note that basal cells (p63+, arrowheads) surround the tube. Scale bars: 20 μm.

Figure 6:
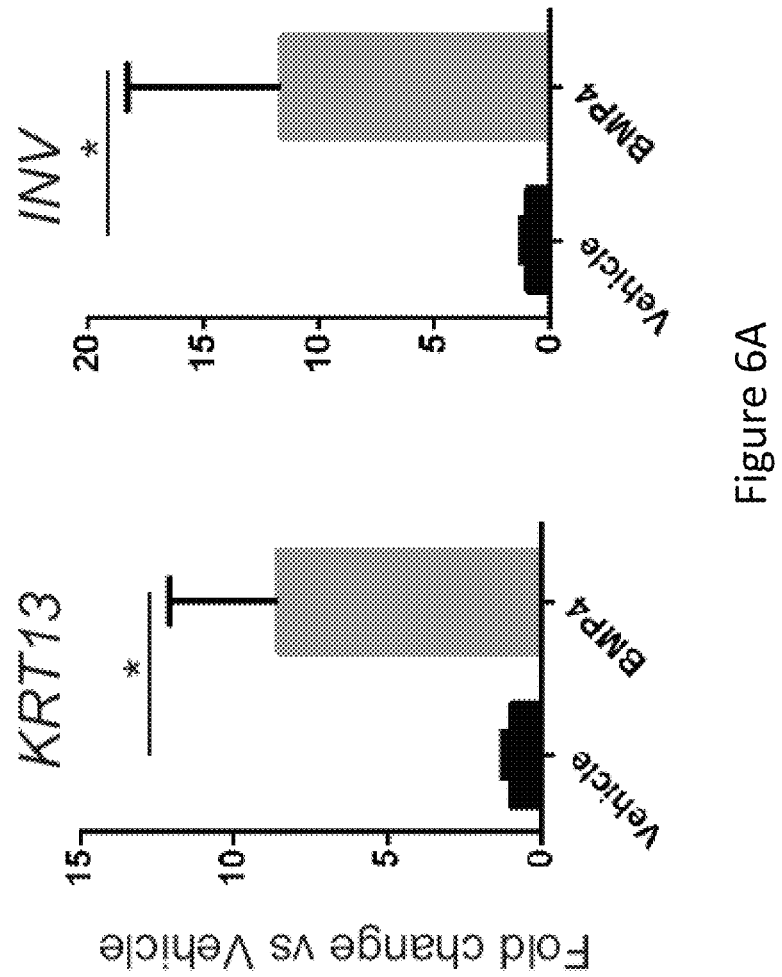
Figure 6B:
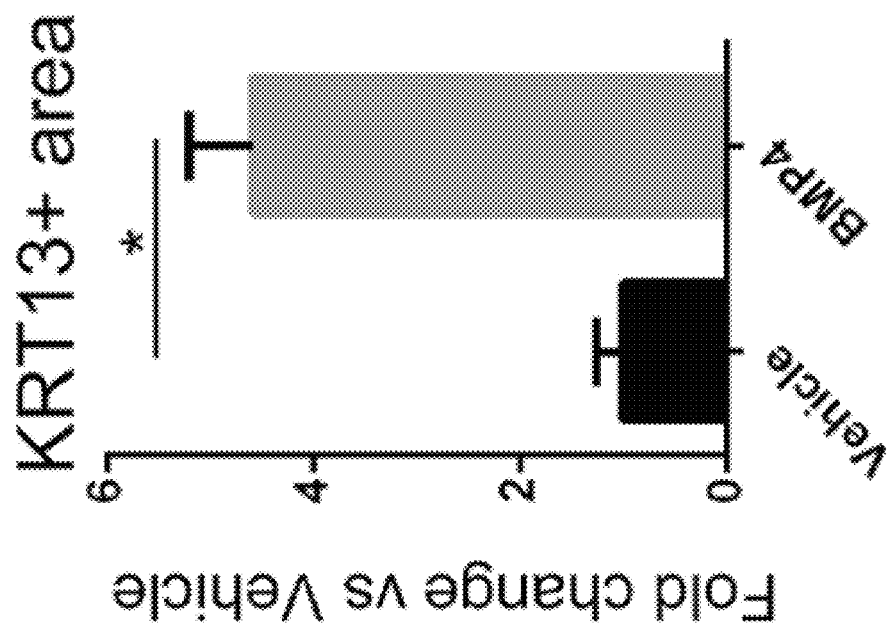
Figure 6B:
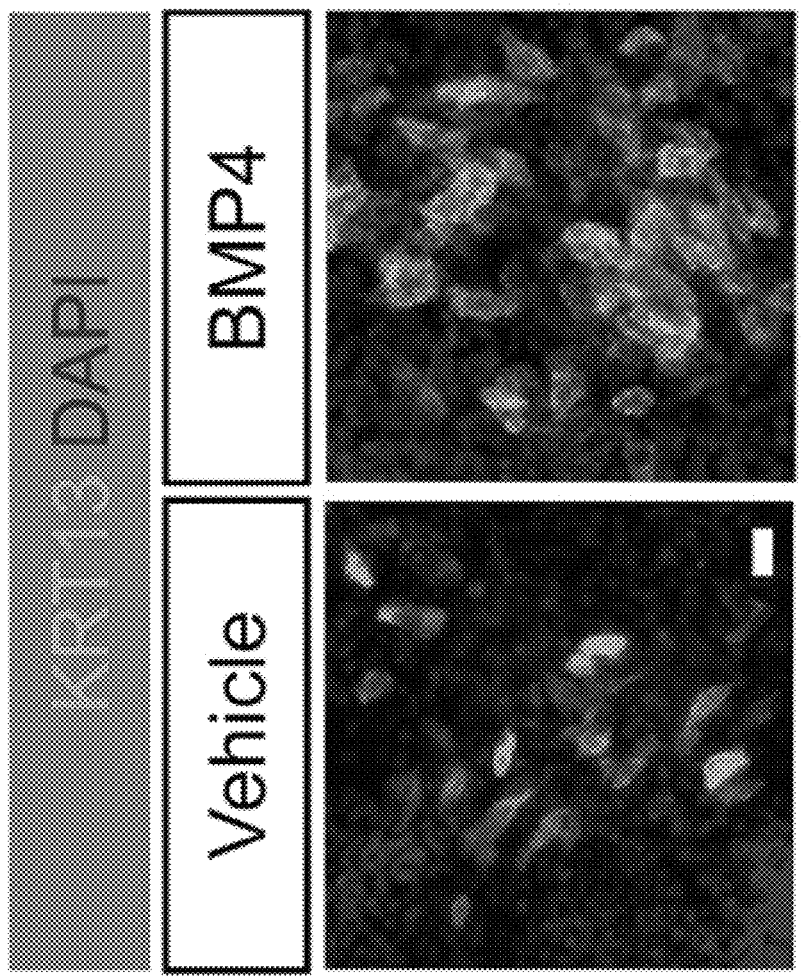
Figure 6C:
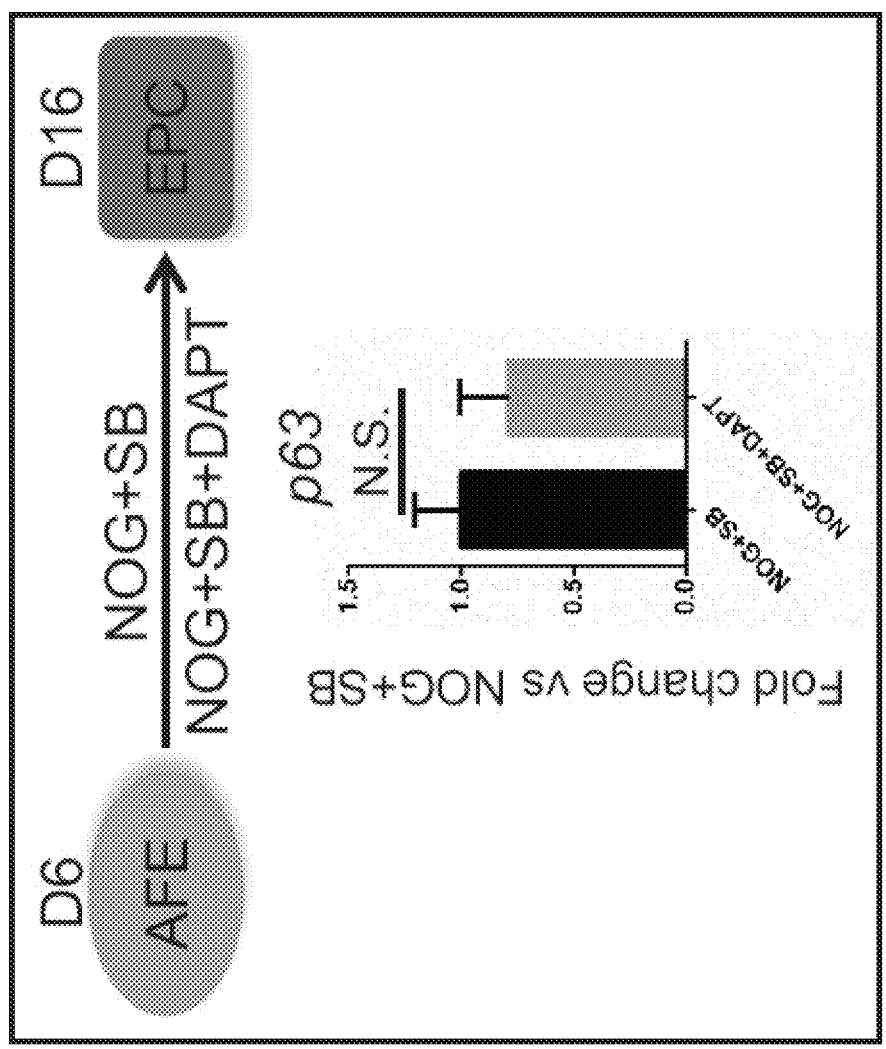
Figure 6D:
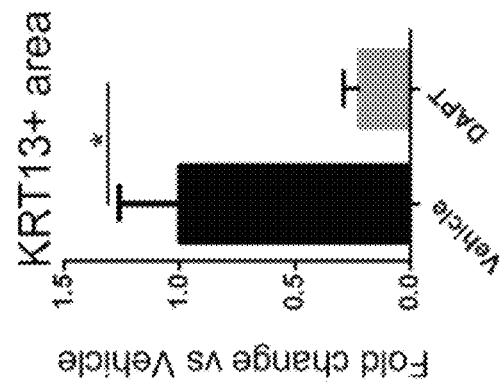
Figure 6D:
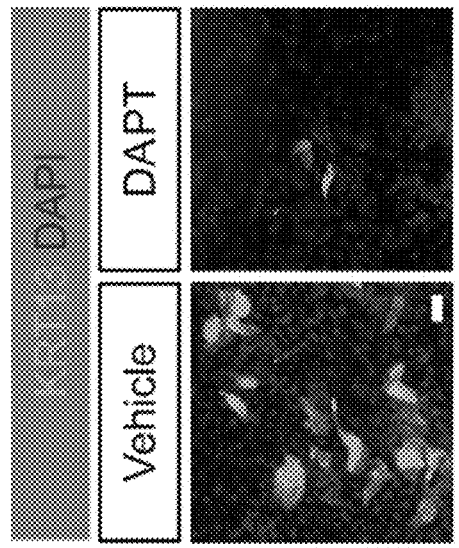
Figure 6D:
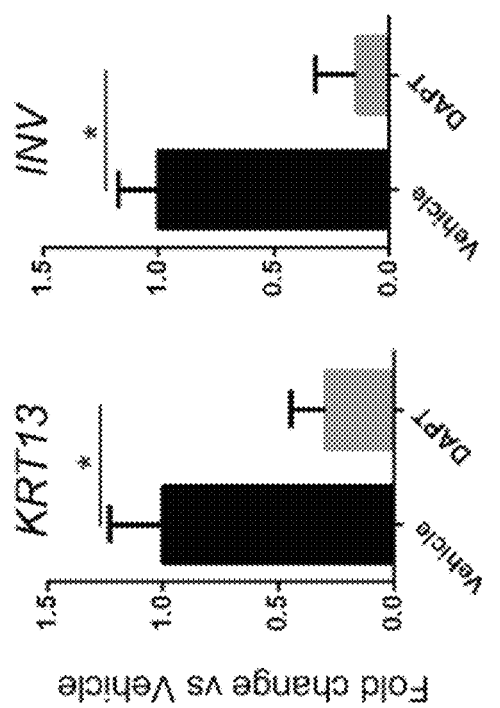
Figure 6E:
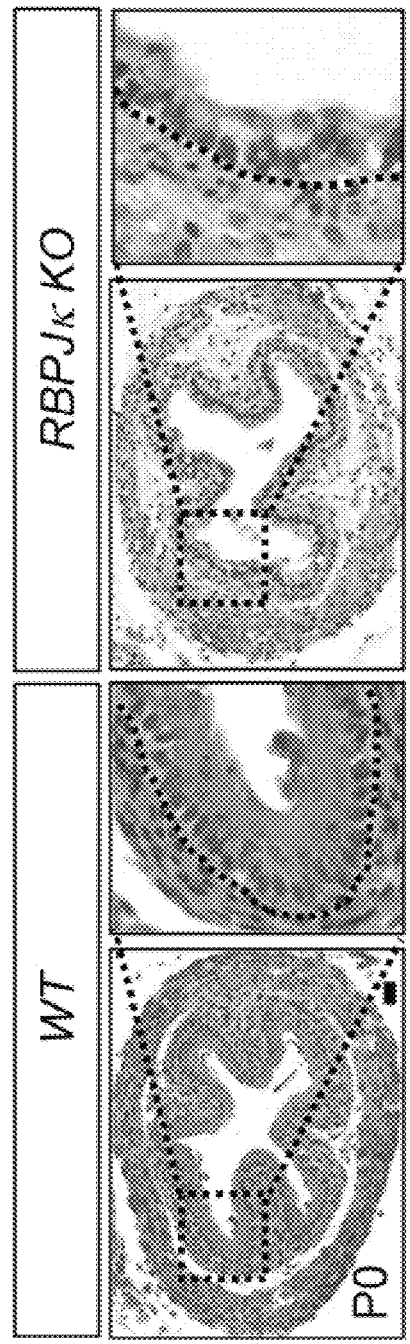
Figure 6F:
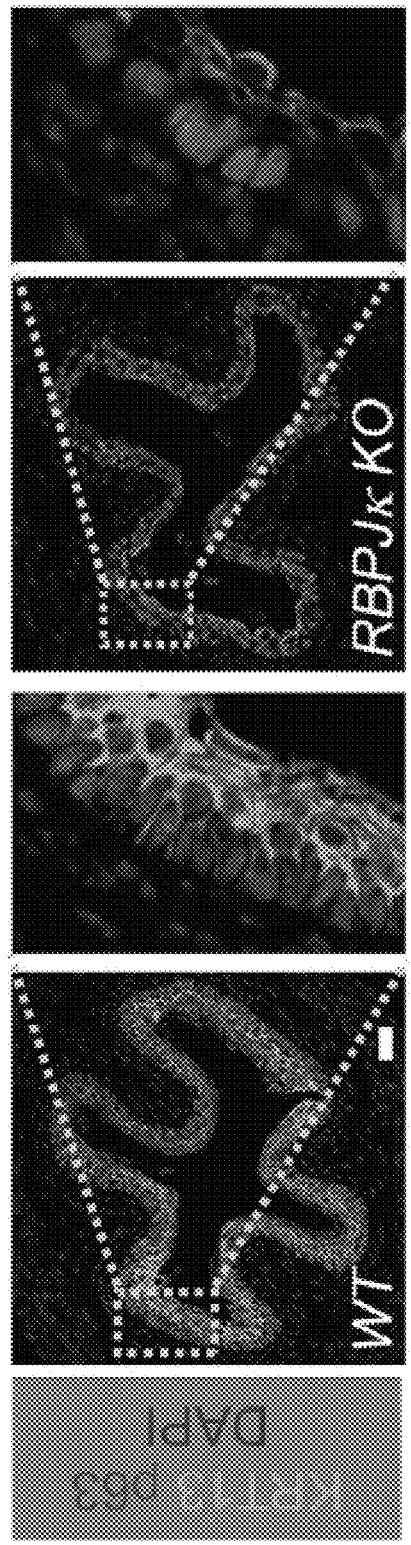
Figure 6G:
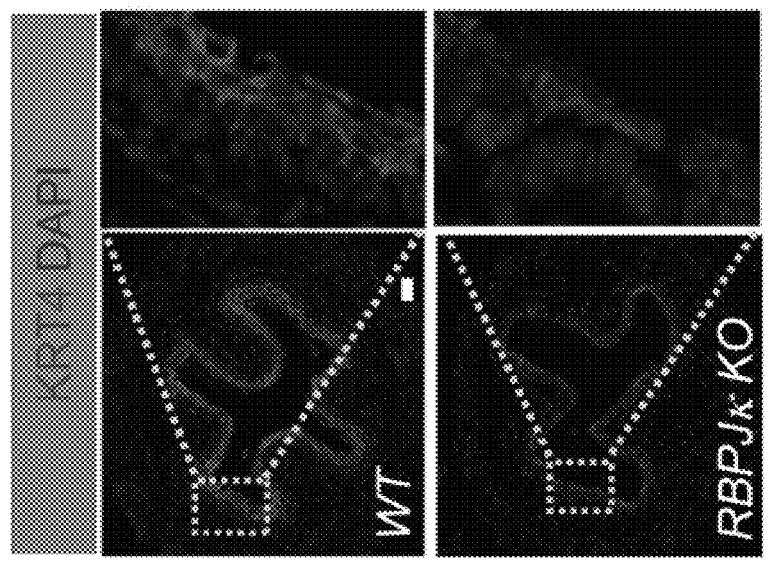

FIG. 6 shows the conserved roles for BMP and NOTCH signaling in the differentiation of hPSC-derived EPCs. FIG. 6A is graphs of the expression of KRT13 or INV in hPSC-derived EPCs treated with BMP4 or vehicle. FIG. 6B shows representative images and graphs that BMP4 treatment increased levels of KRT14. FIG. 6C is a graph of the fold change of cells differentiating from AFE to EPC when DAPT is added. FIG. 6D shows the expression of differentiation markers KRT13 and INV in hPSC-derived EPCs treated with the NOTCH inhibitor DAPT and vehicle. FIG. 6E are images of stratified squamous epithelium in the esophagus of wild-type and Shh-Cre; RBPJK$^{loxp/loxp}$ mutant mice. Note the reduced thickness of the suprabasal layers (KRT13+ KRT4+) in mutants. FIG. 6F show the same cells immunostained for KRT13 and p63. FIG. 6G are images of the same cells immunostained for KRT4. Scale bars: 20 μm.

Figures 7, 7A:
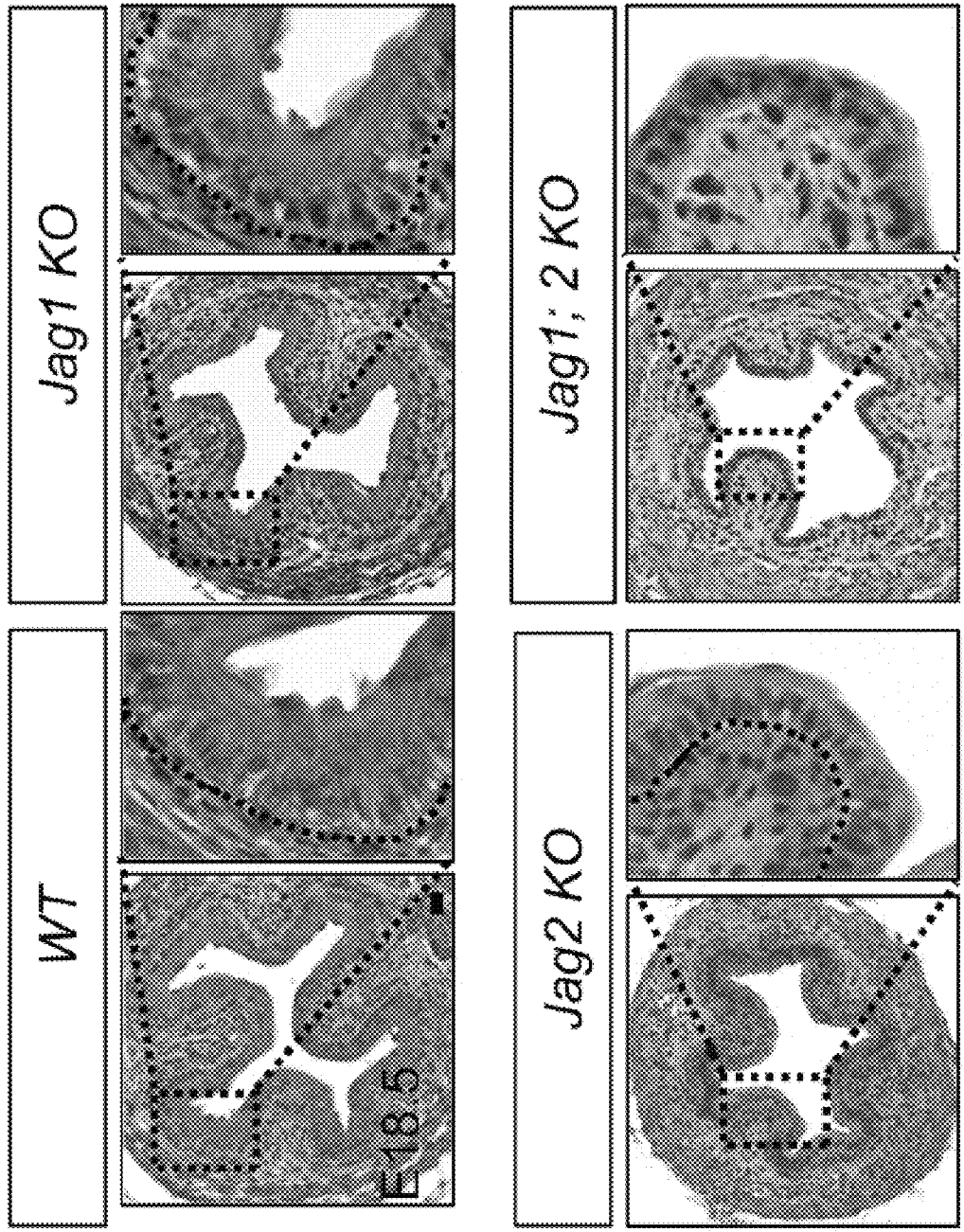
Figure 7B:
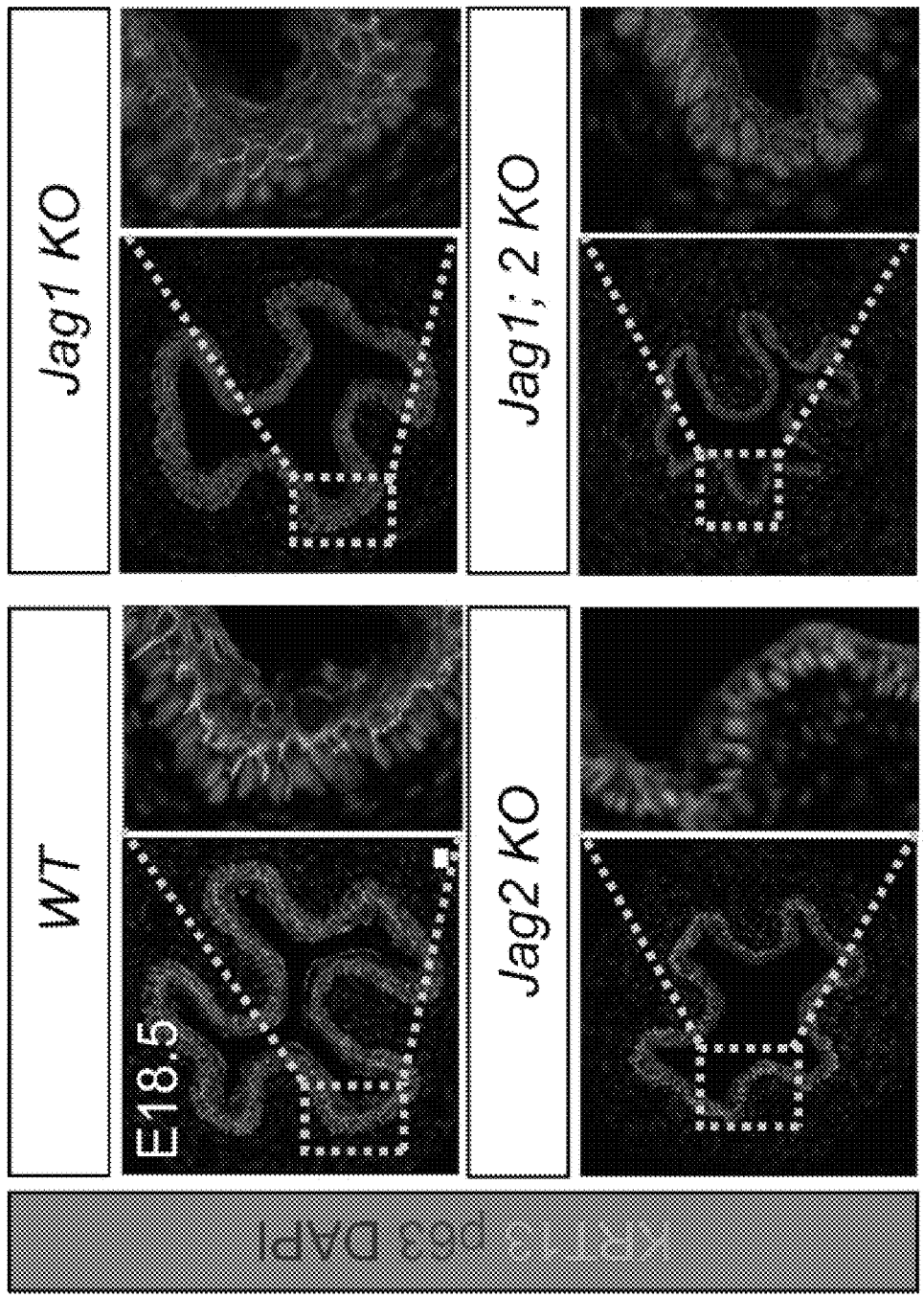
Figure 7C:
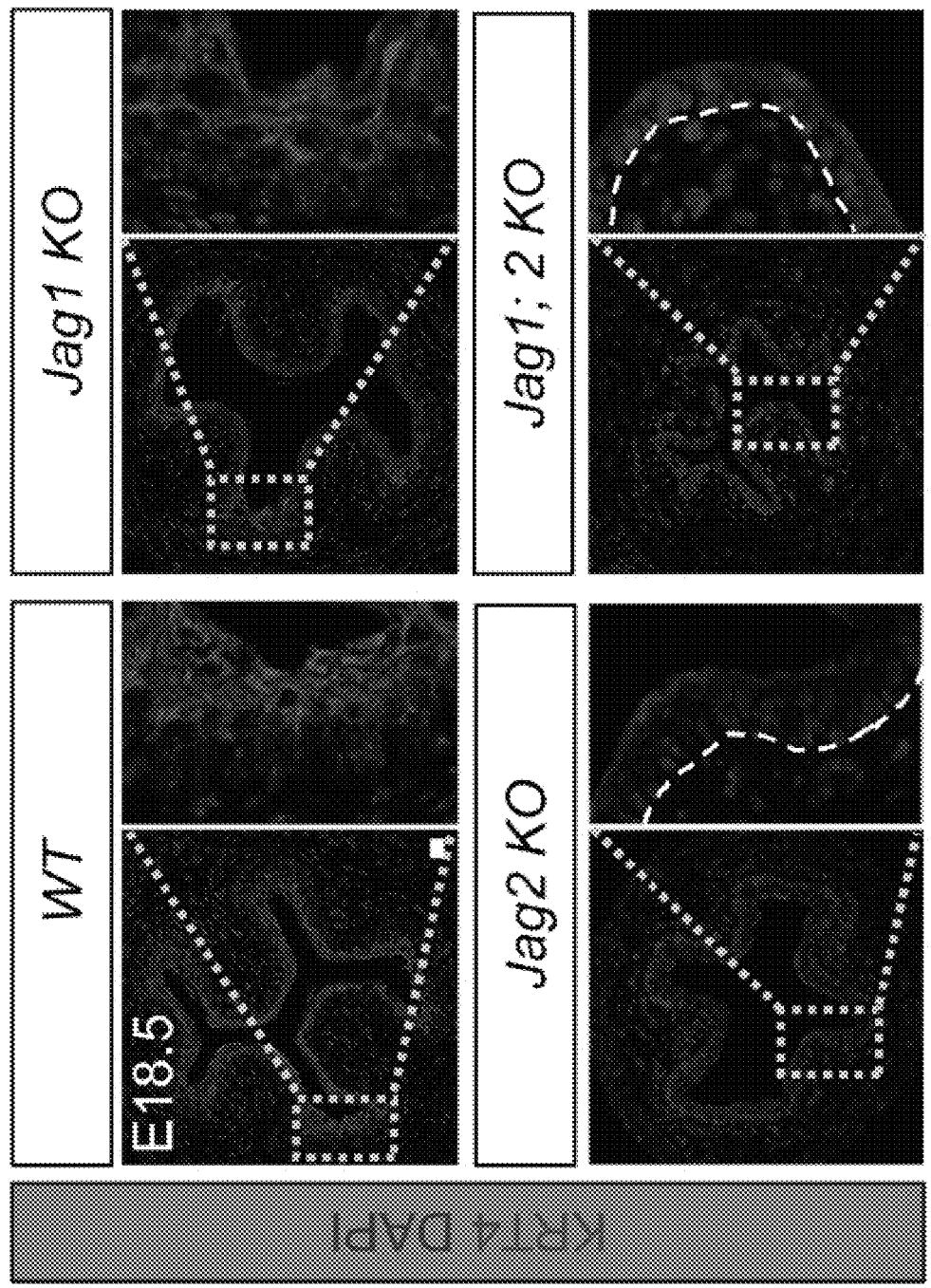

FIG. 7 shows the conditional deletion of the NOTCH ligands Jag1 and Jag2 impairs the squamous differentiation of esophageal progenitor cells. FIG. 7A are images of the stratified squamous epithelium of the esophagus of wild type, Jag1KO, Jag2 KO, and JAG1:2 KO compound mutant mice. Shh-Cre mediated deletion of Jag2 but not Jag1 blocks the formation of the stratified squamous epithelium. Note comparable phenotypes in mutants lacking Jag2 only and Jag1; Jag2. FIG. 7B show images of the same cells immunostained for KRT13 and p63. FIG. 7C are images of the same cells immunostained for KRT4. Note the significant loss of KRT4 and KRT13 expression in the mutant esophagus. Scale bars: 20 μm.

DETAILED DESCRIPTION OF THE INVENTION

Definitions

As used herein, the term "induced pluripotent stem cells" commonly abbreviated as iPS cells or iPSCs, refers to a type of pluripotent stem cell artificially generated from a non-pluripotent cell, typically an adult somatic cell, or terminally differentiated cell, such as fibroblast, a hematopoietic cell, a myocyte, a neuron, an epidermal cell, or the like.

As used herein, the terms "differentiation" and "cell differentiation" refer to a process by which a less specialized cell (i.e., stem cell) develops or matures or differentiates to possess a more distinct form and/or function into a more specialized cell or differentiated cell, (i.e., esophageal cell).

The term "agent" as used herein means a substance that produces or is capable of producing an effect and would include, but is not limited to, chemicals, pharmaceuticals, drugs, biologics, small molecules, antibodies, nucleic acids, peptides, and proteins.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

With respect to cells, the term "isolated" refers to a cell that has been isolated from its natural environment (e.g., from a tissue or subject). The term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject.

The term "in need thereof" would be a subject known or suspected of having or being at risk of developing a disease including but not limited to esophageal cancer.

A subject in need of treatment would be one that has already developed the disease. A subject in need of prevention would be one with risk factors of the disease.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

Many esophageal diseases including malignancy are associated with stem/progenitor cell abnormalities involving reactivation of developmental signaling pathways. However, anatomical and structural differences between species render mouse a suboptimal organism for studying esophageal development and disease mechanism. To address this issue an efficient protocol to generate esophageal epithelial progenitors (EPCs) from human pluripotent stem cells (hPSCs) including embryonic stem cells (ESCs) and induced pluripotent stem cells (iPSCs) has been established and reported herein. Specifically, inhibition of TGFß and BMP signaling is required for the sequential differentiation of hPSCs into EPCs which can be further purified with the cell surface markers EPCAM and Integrin ß4. The hPSC-derived EPCs recapitulate the normal development of the stratified squamous epithelium in the human esophagus. More importantly, a combination of hPSC differentiation and mouse genetics allows the elucidation of the critical role for NOTCH signaling in the formation of the stratified squamous epithelium. These studies therefore not only provide an efficient approach to generate human EPCs, but also offer a new model to study the regulatory mechanisms underlying the development of the human esophagus.

This method used the BMP inhibitor Noggin to promote the commitment of anterior foregut endoderm (AFE) towards esophageal progenitor cells (EPCs) (p63+ SOX2$^+$ NKX2.1$^-$). This is in contrast to the effect of WNTs which promote the differentiation of AFE into lung epithelial progenitors (NKX2.1$^+$) (McCauley et al., 2017). It has been consistently shown that WNT signaling promotes lung specification while BMP signaling needs to be inhibited by Noggin to allow generation of the esophagus in mice. Deletion of ß-catenin or Nog leads to abnormal formation of the lung and esophagus, respectively (Domyan et al., 2011; Goss et al., 2009; Harris-Johnson et al., 2009; Que et al., 2006). Furthermore, ectopic WNT activation in genetically engineered mice suppresses the formation of the squamous epithelium in both forestomach and esophagus (Goss et al., 2009; Harris-Johnson et al., 2009).

It is shown herein that there is low WNT signaling activities during the specification of EPCs. Ectopic WNT activation in combination with BMP and TGFß dual inhibition represses EPC specification accompanied by increased expression of PROX1 and HNF6, which are expressed in the posterior foregut-derived organs, e.g. liver and pancreas (Burke and Oliver, 2002), suggesting ectopic WNT signaling posteriorizes the foregut (Ober et al., 2006; Wells et al., 2007).

In line with this observation, inhibition or activation of canonical WNT signaling represses the differentiation of AFE towards EPCs. Following the establishment from the foregut, BMP signaling is required for the differentiation of epithelial progenitor cells in the developing mouse esophagus (Jiang et al., 2015; Rodriguez et al., 2010). The results herein are consistent in that BMP4 treatment promotes the differentiation of hPSC-derived EPCs. Therefore, the function of BMP signaling in esophageal morphogenesis seems conserved in mice and humans.

The hPSC differentiation system set forth herein offers a new avenue to study the mechanisms regulating the development of the esophagus. Here, studies using hPSCs and mouse genetic models identified the role of NOTCH signaling in the differentiation of epithelial progenitor cells in the developing esophagus. Notch ligands (Jag1 and Jag2) were found to be enriched in the esophageal epithelium and hPSC-derived EPCs. Consistently, blocking NOTCH signaling in both mouse genetic models and hPSC-derived EPCs leads to reduced squamous differentiation of esophageal progenitor cells. These studies prove that a combination of mouse genetics and hPSCs differentiation is powerful for elucidating the developmental mechanisms conserved between species.

Notably, through the differentiation of hPSCs it was found that SOX9 is expressed in the early esophageal progenitor cells. It was also further shown that SOX9 is expressed in the epithelium of the developing mouse esophagus but the expression is lost in adults. Interestingly, SOX9 is highly expressed in the lung epithelium at the early stage of development, but the expression falls to undetectable levels in the adult lung (Chang et al., 2013; Rockich et al., 2013). Conditional deletion of SOX9 disrupts lung branching morphogenesis and epithelial differentiation (Chang et al., 2013;

Rockich et al., 2013). Although the role of SOX9 in the developing esophagus remains unknown, re-expression of SOX9 accompanied by high levels of KRT7 has been found in Barrett's esophagus (also known as intestinal metaplasia) and esophageal adenocarcinoma (Jiang et al., 2017; Song et al., 2014; Wang et al., 2014). How SOX9 is involved in the pathogenesis of Barrett's esophagus and tumorigenesis remains unknown. Study of the hPSC-derived EPCs (SOX9$^+$) may provide new insights into this issue.

In summary, set forth herein is a robust protocol to derive EPCs from both hESCs and iPSCs. The hPSC-derived EPCs are capable of undergoing normal differentiation and generating the stratified squamous epithelium from simple columnar cells both in vitro and in vivo. This differentiation system combined with mouse genetic models allowed the identification of the conserved roles of the BMP and NOTCH pathways in the morphogenesis of the esophagus.

Methods and Systems of Obtaining Esophageal Epithelial Progenitor Cells

The methods and systems described herein not only provide a reproducible method to obtain esophageal epithelial progenitor cells by inducing differentiation of human pluripotent stem cells into esophageal progenitor cells (EPCs) but also provide an increase the purity and homogeneity of the esophageal progenitor cells (EPCs) cells, thus increasing function.

The methods and systems set forth herein generate a defined and reproducible cell population that is fully functional upon transplantation. Furthermore, the methods and systems set forth herein provide a substantially homogenous population of esophageal epithelial progenitor cells.

A human pluripotent stem cell is the starting material of the methods of the invention. The human pluripotent stem cell (hPSCs) can be an embryonic stem cells (ESCs) or an induced pluripotent stem cell (iPSCs).

The steps of the method and the timing are set forth in Table 1.

TABLE 1

Timeline of the Method of the Invention

| STEP | TIMING | GENERAL DESCRIPTION |
|---|---|---|
| 1 | Performed from about day 1 to about day 4 (about 72 hours) | Differentiate hPSCs to endoderm cells |
| 2 | Performed about 72 hours to about 96 hours after the start of step 1, thus starting from about day 4 to about day 5 and performed for about 48 to about 72 hours, ending at about day 6 to day 8 | Differentiate endoderm cells to anterior foregut endoderm cells by inhibiting BMP and TGFβ signaling only or by further inhibiting TGFβ signaling and WNT/β-catenin signaling |
| 3 | Performed about 48 hours to about 72 hours after the start of step 2, thus starting from about day 6 to about day 8 and performed for about 2 days to about 10 days ending at about day 8 to about day 18 | Differentiate anterior foregut endoderm cells to esophageal progenitor cells by inhibiting BMP and TGFβ signaling |
| 4 | Performed for about 2 days to about 10 days after step 3 ending at about day 10 to about day 28 | Culturing the cells in serum-free medium to further promote differentiation |

The first step of the method is differentiating the hPSCs to endoderm cells using any method known in the art. Exemplified here was the use of a previously published protocol using serum-free differentiation medium containing Activin A, BMP4, FGF2 and a ROCK inhibitor for 72 hours (day 1-4) (See Huang et al. 2015; Huang et al. 2014). See Examples 1 and 2. However, other protocols known in the art can be used. These protocols all generally use Activin A along with other growth factors and reagents. See Yiangou et al. 2018, Table 1.

The next step of the method is the culturing the resulting endoderm cells from the first step to further differentiate into anterior foregut endoderm. Any medium used for differentiation protocols can be used for culturing the cells at this step. A serum-free differentiation medium is preferred.

The endoderm cells are then contacted or incubated with an agent that inhibits BMP and an agent that inhibits TGFβ signaling to promote differentiation of the endoderm cells to anterior foregut progenitor cells. The most efficient method to accomplish this is by adding the agents to the medium in which the cells are being cultured. However, any other method known in the art that would contact or incubate the cells with the agents can be used. The cells can be contacted or incubated with the agents simultaneously or concurrently.

Agents that inhibit BMP include but are not limited to Noggin and Dorsomorphin. Agents that inhibit TGFβ signaling include but are not limited to SB431542.

Dorsomorphin can be used in an amount ranging from about 0.5 µM to about 2 µM.

A preferred agent for the inhibition of BMP is Noggin in an amount ranging from about 50 ng/ml to about 200 ng/ml with about 100 ng/ml being a preferred amount.

A preferred agent for the inhibition of TGFβ signaling is SB431542 in an amount ranging from about 1 µM to about 20 µM with 10 µM being a preferred amount.

Optionally, the cells are cultured and further contacted with an agent that inhibits TGFβ signaling and an agent that inhibits WNT/β-catenin. The most efficient method to accomplish this is by adding the agents to the medium in which the cells are being cultured. However, any other method known in the art that would contact or incubate the cells with the agents can be used. The cells can be contacted or incubated with the agents simultaneously or concurrently.

Again a preferred agent for the inhibition of TGFβ signaling is SB431542 in an amount ranging from about 1 µM to about 20 µM with 10 µM being a preferred amount.

However, other agents that inhibit TGFβ signaling can be used in the method of the invention.

Agents that inhibit WNT/β-catenin include but are not limited to IWP-2.

A preferred agent for inhibition of WNT/β-catenin is IWP-2 in an amount ranging from about 0.5 µM to about 2.0 µM with about 1.0 µM being preferred.

The cells continue to be cultured in any serum-free medium used for differentiation of cells. Additionally, growth factors such as EGF and FGF10 can be added to the medium to promote cellular growth. The next step promotes differentiation of the anterior foregut cells into esophageal progenitor cells.

In this step, the cells are then contacted or incubated with both an agent that inhibits BMP and an agent that inhibits TGFβ signaling. The most efficient method to accomplish this is by adding the agents to the medium in which the cells are being cultured. However, any other method known in the art that would contact or incubate the cells with the agents can be used. The cells can be contacted or incubated with the agents simultaneously or concurrently.

Agents that inhibit BMP include but are not limited to Noggin and Dorsomorphin. Agents that inhibit TGFβ signaling include but are not limited to SB431542.

Dorsomorphin can be used in an amount ranging from about 0.5 µM to about 2 µM.

A preferred agent for the inhibition of BMP is Noggin in an amount ranging from about 50 ng/ml to about 200 ng/ml with about 100 ng/ml being a preferred amount.

A preferred agent for the inhibition of TGFβ signaling is SB431542 in an amount ranging from about 1 µM to about 20 µM with 10 µM being a preferred amount.

In step four, the cells are continued to be cultured in any differentiation medium known in the art, preferably serum-free medium with growth factors such as EGF and FGF10.

While the method set forth above is a novel, reproducible and robust method to induce the differentiation of hPSCs to EPCs, the present invention also provides for further steps for purifying the EPCs obtained by the steps set forth above using novel cell surface markers found to be expressed by the EPCs, EPCAM+ and ITGβ4+. This step can be done using any method known in the art to purify or isolate such cells including flow cytometry, the use of antibodies and magnetic beads.

One method to separate or isolate the cells based on expression or surface expression of markers is the use of antibodies such as monoclonal antibodies to identify markers associated with particular cell lineages and/or stages of differentiation. The antibodies can be attached to a solid support to such that cells that express the markers are immobilized, thereby allowing the separation of cells that express that marker from cells that do not express the marker. The separation techniques used should maximize the retention of viable cells to be collected. Such separation techniques can result in sub-populations of cells where up to 10%, usually not more than about 5%, preferably not more than about 1%, of the selected cells do not express the marker in question. The particular technique employed will depend upon efficiency of separation, associated cytotoxicity, ease and speed of performance, and necessity for sophisticated equipment and/or technical skill. An "isolated" or "purified" population of cells is substantially free of cells and materials with which it is associated in nature, in particular, free of cells that lack the desired phenotype. Substantially free or substantially purified includes at least 50% EPCAM+ ITGβ4+ EPCs, preferably at least 70% EPCAM+ ITGβ4+ EPCs, more preferably at least 80% EPCAM+ ITGβ4+ EPCs, and even more preferably at least 90% EPCAM+ ITGβ4+ EPCs.

As noted, techniques providing accurate separation of cells further include flow cytometry, which can have varying degrees of sophistication, e.g., a plurality of color channels, low angle and obtuse light scattering detecting channels, impedance channels, etc. Cells also can be selected by flow cytometry based on light scatter characteristics, where stem cells are selected based on low side scatter and low to medium forward scatter profiles. Cytospin preparations show for example, that enriched stem cells to have a size between mature lymphoid cells and mature granulocytes.

The present invention also includes systems for practicing the methods of the invention for obtaining EPCAM+ ITGβ4+ EPCs from hPSCs. These systems can include subsystems wherein the subsystems include differentiation medium, agents which inhibit BMP, TGFβ signaling, and WNT/β-catenin, and a subsystem for further purifying cells using cell surface markers EPCAM+ and ITGβ4+.

Cells

A further embodiment of the present invention are the EPCs generated by the differentiation protocol set forth herein. These EPCs are SOX2+p63+ EPCAM+ ITGβ4+ NKX2.1-. These EPCs express squamous differentiation proteins KRT and KRT13 when cultured. Moreover, these cells are able to proliferate and form 3D organoids. Additionally these EPCs undergo normal squamous differentiation and reconstitute into stratified squamous epithelium both in vivo and in vitro.

Thus, one aspect of the present invention is SOX2+p63+ EPCAM+ ITGβ4+ NKX2.1-esophageal progenitor cells suitable for administration, transplantation and grafting into a subject produced by the methods of the invention as described herein.

In another aspect, provided herein is a composition comprising the SOX2+p63+ EPCAM+ ITGβ4+ NKX2.1- esophageal progenitor cells produced by the methods of the invention as described herein. In some embodiments, these cells are suitable for administration, transplantation and grafting into a subject. In some embodiments, the composition is a pharmaceutical composition further comprising any pharmaceutically acceptable carrier or excipient.

In certain embodiments, the composition or pharmaceutical composition comprises at least 10,000, at least 50,000, at least 100,000, at least 500,000, at least $1 \times 10^6$, at least $5 \times 10^6$, at least $1 \times 10^7$, at least $5 \times 10^7$, at least $1 \times 10^8$, at least $5 \times 10^8$, at least $1 \times 10^9$, at least $5 \times 10^9$, or at least $1 \times 10^{10}$ SOX2+p63+ EPCAM+ ITGβ4+ NKX2.1- esophageal progenitor cells produced by the methods of the invention as described herein. In some embodiments, these cells are suitable for administration, transplantation and grafting into a subject.

In certain embodiments, the invention provides a cryopreserved composition or solution of the SOX2+p63+ EPCAM+ ITGβ4+ NKX2.1- esophageal progenitor cells produced by the methods of the invention as described herein. In some embodiments, these cells are suitable for administration, transplantation and grafting into a subject.

In certain embodiments, the cryopreserved composition or solution comprises at least 10,000, at least 50,000, at least 100,000, at least 500,000, at least $1 \times 10^6$, at least $5 \times 10^6$, at least $1 \times 10^7$, at least $5 \times 10^7$, at least $1 \times 10^8$, at least $5 \times 10^8$, at least $1 \times 10^9$, at least $5 \times 10^9$, or at least $1 \times 10^{10}$ SOX2+p63+ EPCAM+ ITGβ4+ NKX2.1- esophageal progenitor cells produced by the methods of the invention as described herein. In some embodiments, these cells are suitable for administration, transplantation and grafting into a subject.

In certain embodiments, the invention provides for cell culture comprising SOX2+p63+ EPCAM+ ITGβ4+ NKX2.1- esophageal progenitor cells produced by the invention as described herein. In certain embodiments, the cell culture comprises at least $1 \times 10^7$, at least $5 \times 10^7$, at least $1 \times 10^8$, at least $5 \times 10^8$, at least $1 \times 10^9$, at least $5 \times 10^9$, or at least $1 \times 10^{10}$ SOX2+p63+ EPCAM+ ITGβ4+ NKX2.1- esophageal progenitor cells produced by the methods of the invention as described herein. In some embodiments, these cells are suitable for administration, transplantation and grafting into a subject.

In certain embodiments, the invention provides the therapeutic use of the SOX2+p63+ EPCAM+ ITGβ4+ NKX2.1- esophageal progenitor cells suitable for administration, transplantation and grafting into a subject produced by the methods of the invention as described herein, and compositions, solutions and cell cultures comprising such cells.

In other embodiments, the invention provides for a population of substantially homogenous SOX2+p63+ EPCAM+ ITGβ4+ NKX2.1- esophageal progenitor cells produced by the methods of the invention as described herein. In some embodiments, these cells are suitable for administration, transplantation and grafting into a subject. In some embodiments, the population of cells comprises at least about 90%, 91%, 92%, 93%, 94%, 95%, 96%, 97%, 98%, or 99% SOX2+p63+ EPCAM+ ITGβ4+ NKX2.1− esophageal progenitor cells.

In another aspect, provided herein is a composition comprising the population of substantially homogenous SOX2+ p63+ EPCAM+ ITGβ4+ NKX2.1− esophageal progenitor cells produced by the methods of the invention as described herein. In some embodiments, these cells are suitable for administration, transplantation and grafting into a subject. In some embodiments, the composition is a pharmaceutical composition further comprising any pharmaceutically acceptable carrier or excipient.

In certain embodiments, the population or composition or pharmaceutical composition comprises at least 10,000, at least 50,000, at least 100,000, at least 500,000, at least $1\times10^6$, at least $5\times10^6$, at least $1\times10^7$, at least $5\times10^7$, at least $1\times10^8$, at least $5\times10^8$, at least $1\times10^9$, at least $5\times10^9$, or at least $1\times10^{10}$ SOX2+p63+ EPCAM+ ITGβ4+ NKX2.1− esophageal progenitor cells produced by the methods of the invention as described herein. In some embodiments, these cells are suitable for administration, transplantation and grafting into a subject.

In certain embodiments, the invention provides a cryopreserved composition or solution of the population of substantially homogenous SOX2+p63+ EPCAM+ ITGβ4+ NKX2.1-esophageal progenitor cells produced by the methods of the invention as described herein. In certain embodiments, the cryopreserved composition or solution comprises at least 10,000, at least 50,000, at least 100,000, at least 500,000, at least $1\times10^6$, at least $5\times10^6$, at least $1\times10^7$, at least $5\times10^7$, at least $1\times10^8$, at least $5\times10^8$, at least $1\times10^9$, at least $5\times10^9$, or at least $1\times10^{10}$ SOX2+p63+ EPCAM+ ITGβ4+ NKX2.1− esophageal progenitor cells produced by the methods of the invention as described herein. In some embodiments, these cells are suitable for administration, transplantation and grafting into a subject.

In certain embodiments, the invention provides for cell culture comprising population of substantially homogenous SOX2+p63+ EPCAM+ ITGβ4+ NKX2.1− esophageal progenitor cells produced by the invention as described herein. In certain embodiments, the cell culture comprises at least $1\times10^7$, at least $5\times10^7$, at least $1\times10^8$, at least $5\times10^8$, at least $1\times10^9$, at least $5\times10^9$, or at least $1\times10^{10}$ SOX2+p63+ EPCAM+ ITGβ4+ NKX2.1− esophageal produced by the methods of the invention as described herein. In some embodiments, these cells are suitable for administration, transplantation and grafting into a subject.

In certain embodiments, the invention provides the therapeutic use of the population of substantially homogenous SOX2+p63+ EPCAM+ ITGβ4+ NKX2.1− esophageal progenitor cells suitable for transplantation and grafting into a subject produced by the methods of the invention as described herein, and compositions, solutions and cell cultures comprising such cells.

Therapeutic Uses

The novel method described herein for the generation of SOX2+p63+ EPCAM+ ITGβ4+ NKX2.1− esophageal progenitor cells from stem cells and the cells and substantially homogenous population of cells generated from this method, provide new therapies for diseases of the esophagus including but not limited to esophagitis, Barrett's Esophagus, and esophageal cancer.

Thus, one embodiment of the present invention is a method of treating or preventing a disease of the esophagus comprising the steps of administering, transplanting or grafting a therapeutically effective amount of the cells of the present invention, a solution comprising the cells of the invention, a composition comprising the cells of the invention, or a pharmaceutical composition comprising the cells of the invention as described herein, to the subject in need thereof. The subject is preferably a mammal, and most preferably human.

Kits

The present invention also provides kits comprising the components of the combinations of the invention in kit form.

In one embodiment, the kit includes one or more components including human pluripotent stem cells, medium for culturing and differentiation the hPSCs, such medium including growth factors and agents which inhibit BMP, TGFβ signaling and WNT/β-catenin, containers for culturing the cells, and instructions. In a further embodiment, the kit includes components for further purifying the cells after culturing using cell surface markers EPCAM+ ITGβ4+. Such components include antibodies to EPCAM+ and ITGβ4+ including monoclonal antibodies. The antibodies can be attached to solid surface for use. Other components for purification include magnetic beads.

In further embodiments, a kit can include the SOX2+p63+ EPCAM+ ITGβ4+ NKX2.1-esophageal progenitor cells obtained by the current methods and systems of the invention. The kit can also comprise reagents for culturing the cells.

In further embodiments, a kit can include a pharmaceutical composition comprising the esophageal progenitor cells obtained by the current methods and systems of the invention.

In further embodiments, a kit can include a cryopreserved composition comprising the esophageal progenitor cells obtained by the current methods and systems of the invention.

The kits can further include a package insert including information concerning the pharmaceutical compositions and dosage forms in the kit. For example, the following information regarding a combination of the invention may be supplied in the insert: how supplied, proper storage conditions, references, manufacturer/distributor information and patent information.

EXAMPLES

The present invention may be better understood by reference to the following non-limiting examples, which are presented in order to more fully illustrate the preferred embodiments of the invention. They should in no way be construed to limit the broad scope of the invention.

Example 1—Materials and Method for Examples 2-6

Mice

Shh-Cre (Harfe et al., 2004), RBPj$^{loxp/loxp}$ (Han et al., 2002), Jag1$^{loxp/loxp}$ (Brooker et al., 2006); Jag2$^{loxp/loxp}$ (Xu et al., 2010), BRE-lacZ (Blank et al., 2008), Noggin-lacZ (McMahon et al., 1998), NOD.Cg-Prkd$^{cscid}$.Il2rg$^{tm1Wjlnlw}$/SzJ (NSG) mice (The Jackson Laboratory) were maintained on a C57BL/6 and 129SvEv mixed background, 8 to 24 weeks of age, and of both sexes. All animals were genotyped by PCR of tail DNA. Mice were housed in a specific pathogen free mouse facility with 12-hour light/dark cycle and provided with food and water ad libitum according to Columbia University IACUC. Mice used had no known health/immune concerns, were not involved in previous procedures, and were drug or test naive. Experimental procedures and animal care were performed in accordance with the protocols approved by The Columbia University Institutional Animal Care and Use Committee.

Human Fetal Esophagus

This study was approved by the Medical Ethical Committee of the Leiden Medical University Center (P08.087). Informed consent was obtained and the study was conducted in accordance with the Declaration of Helsinki by the World Medical Association. 10-week-old human fetal esophagi were obtained from abortion material (vacuum aspiration) without medical indication (Roost et al., 2015). De-identified human fetal esophagi between 14-18 weeks of gestation were obtained under IRB approvals at CHLA and USC (USC-HS-13-0399 and CHLA-14-2211) after signed informed consent was granted. Tissues were collected in cold HBSS and processed in the lab within an hour of collection. Tissues from samples with known structural or chromosomal anomalies were excluded from this study.

Maintenance of hPSCs

RUES2 and Sendai virus and modified mRNA generated human dermal fibroblasts iPSC lines (sviPS) and mRNA iPSC were kindly provided by the Mount Sinai Stem Cell Core facility and were cultured as previously described (Huang et al., 2015; Huang et al., 2014). hPSCs lines were maintained on mouse embryonic fibroblasts (MEFs) feeder cells. Briefly, CF-1 MEF (MTI-GlobalStem) mitotically-arrested by irradiation were plated at a density of approximately 25,000 cells/cm2. hPSCs were plated on the fibroblasts and cultured in the maintenance medium: 400 ml of DMEM/F12 (ThermoFisher Scientific), 100 ml of Knock-Out serum replacement (ThermoFisher Scientific), 5 ml of GlutaMAX (ThermoFisher Scientific), 5 ml of MEM-non-essential amino acids (ThermoFisher Scientific), 3.5 µl of 2-mercaptoethanol (Sigma-Aldrich), 1 ml of primocin (ThermoFisher Scientific), and FGF2 (R&D Systems) with a final concentration of 20 ng/ml to make a total of approximately 500 ml of medium. For passaging, cells were detached with Accutase/EDTA (Innovative Cell Technologies) and replated at a ratio of 1:24. Cells were maintained in an incubator with 95% humidity, 95% air and 5% CO2 at 37° C. Human ES/iPS cell research was conducted under the approval of the Columbia University Human Embryonic and Human Embryonic Stem Cell Research Committee.

Endoderm and Anterior Foregut Endoderm (APE) Differentiation hPSCs were differentiated into endodermal and anterior foregut using a previously described protocol (Huang et al., 2015; Huang et al., 2014). Serum-Free Differentiation (SFD) medium was prepared as follows: 750 ml of reconstituted IMDM (ThermoFisher Scientific), 250 ml of F-12 (Corning), 7.5 ml of BSA (ThermoFisher Scientific), 10 ml of Glutamax (ThermoFisher Scientific), 5 ml of N2 (ThermoFisher Scientific), 10 ml of B27 (ThermoFisher Scientific) and 10 ml of Penicillin/Streptomycin (ThermoFisher Scientific), and adding L-Ascorbic acid (Sigma-Aldrich) and MTG (Sigma-Aldrich) on the day of use to obtain a final concentration of 50 µg/ml and 0.04 µl/ml, respectively. To generate endoderm, hPSCs were detached by Accutase/EDTA and cultured in SFD medium plus 10 µM Rock inhibitor 100 ng/ml Activin A, Y-27632 (Tocris), 2.5 ng FGF2 and 0.5 ng/ml BMP4 (R&D Systems) in 6-well Ultra-Low-Attachment plates (Corning) for 72 hours (day 1-4). At day 4, anterior foregut progenitor cells were further induced by culturing endoderm in SFD medium plus 10 µM SB431542 (Tocris) and 100 ng/ml Noggin (R&D Systems) for 24 hours (day 4-5) and SFD medium plus 10 µM SB431542 and 1 µM IWP-2 (Tocris) for another 24 hours (day 5-6). Cells were maintained at 5% O2/95% N2/5% CO2 from day 1-6.

Esophageal and Lung Progenitor Cell Differentiation

To induce esophageal progenitor cell differentiation, anterior foregut progenitor cells were cultured from day 6 to day 16 in SFD medium plus 10 µM SB431542 and 50 ng/ml Noggin. From day 16 to day 24, cells were maintained at SFD medium. A previously described protocol was followed to generate lung progenitor cells from AFE (Huang et al., 2015; Huang et al., 2014) in which AFE cells were cultured in 3 µM CHIR99021 (Tocris), 10 ng/ml human FGF10 (R&D Systems), 10 ng/ml human KGF (R&D Systems), 10 ng/ml human BMP4 and 50 nM retinoid acid (RA, Sigma). Cells were cultured at 5% $O_2$/95% $N_2$/5% $CO_2$ at day 6-7 and maintained at 95% air/5% $CO_2$ from day 7 onwards.

3D Organoid Culture and Air-Liquid Interface (ALI) Culture 20,000 sorted hPSC-derived EPCs (ITGß4$^+$ EPCAM$^+$) were suspended in 75 µl medium and mixed with 75 µl Matrigel (Corning). The mixture was plated in 24-well cell culture inserts (Falcon), and the medium was added to the bottom and top chambers after Matrigel solidified. The organoid culture medium including SFD culture medium supplemented with 10 µM Y27632, 100 ng/ml Noggin, 10 µM SB431542, 3 µM CHIR99021, 20 ng/ml FGF2, 200 ng/ml EGF was modified from previous studies (DeWard et al., 2014; Giroux et al., 2017; Liu et al., 2013). For ALI culture, 20,000 sorted EPCs (ITGß4+ EPCAM+) were cultured in Matrigel-coated 24-well inserts (Falcon) in the SFD medium supplemented with 5% FBS, 20 ng/ml EGF, 20 ng/ml FGF2 and 10 µM Y27632. When cells were confluent, medium was removed from the upper chamber to create air liquid interface, and the culture was further maintained for one month.

Kidney Capsule Implantation

For the kidney transplantation assay, one million RUES2-derived esophageal progenitor cells (day 24 differentiation) were mixed with Matrigel (Coring) at 1:1 ratio and implanted under the kidney capsule as previously described (Chen et al., 2017). Grafts harvested from the kidney capsules at indicated time points were embedded in paraffin and subjected to histological analysis.

Immunofluorescence, X-Gal Staining and Microscopy Imaging

For immunofluorescence staining, cells were fixed in 4% paraformaldehyde (PFA) for 15 minutes at room temperature and washed with 1×PBS for three times. Cells were permeabilized with 0.3% Triton X-100 in 1×PBS for 15 minutes. Then cells were incubated in blocking solution (0.3% Triton X-100 plus 2% donkey serum in 1×PBS) for 1 hour. Primary antibodies were added into blocking solution and incubated at 4° C. overnight. The next day, cells were washed with 1×PBS for three times. Secondary antibodies conjugated to Alexa Fluor 488, Cy3, or Alexa Fluor 647 (Jackson Immunoresearch) were incubated for 1 hour. Images were taken using Leica DMI6000 B (Leica Microsystems) or DMi8 (Leica Microsystems) and a Zeiss LSM700 confocal laser scanning microscope. Bright field images were acquired using a Nikon Labophot 2 microscope equipped with a Nikon Digital Sight DS-Ri1 charge-coupled device camera. The thickness and areas composed of KRT13$^+$ cells were calculated by ImageJ (National Institutes of Health). Primary antibodies are listed in Table 2. For X-gal staining, tissues were fixed in 4% paraformaldehyde for 30 minutes and incubated in X-gal solution overnight at 37° C. as previously described (Que et al., 2006).

Mouse and Human Fetal Esophageal Epithelium Isolation

Muscle layers were stripped off the esophagi using forceps and the remaining tissue (epithelium and mesenchyme) was incubated in 50 Um' Dispase (Corning) in 1×PBS for 10 minutes at room temperature for mouse esophagi and 16 U/ml Dispase for 8 minutes at room temperature for human fetal esophagi. Epithelium was peeled off from mesenchyme with forceps and subjected to RNA purification.

TABLE 2

Antibody list

| Antibodies | Host species | Source | Identifier |
|---|---|---|---|
| APC-conjugated CXCR4 | Mouse | Biolegend | 306510 |
| PE-conjugated CXCR4 | Mouse | Biolegend | 306505 |
| PE-conjugated EpCAM | Mouse | Biolegend | 324208 |
| PE-conjugated c-Kit | Mouse | Biolegend | 313204 |
| PE-conjugated ITGB4 | Mouse | Biolegend | 327807 |
| P63 | Rabbit | Santa Cruz | sc-8343(Clone H-173) |
| P63 | Mouse | Biolegend | 687202 |
| P63-α | Rabbit | Cell Signaling | 13109 |
| NKX2.1 | Mouse | ThermoFisher Scientific | MA5-13961 (8G7G3/1) |
| NKX2.1 | Rabbit | abcam | ab76013 (EP1584Y) |
| SOX2 | Rat | eBiosciences | 14-9811 |
| FOXA2 | Goat | Santa Cruz | sc-6554 (Clone M-20) |
| FOXA1 | Mouse | Santa Cruz | sc-101058 (Q-6) |
| SOX9 | Goat | R&D Systems | AF3075 |
| PAX9 | Mouse | Biolegend | 658202 |
| KRT4 | Mouse | abcam | ab9004 |
| KRT5 | Chicken | Biolegend | 905901 |
| KRT7 | Mouse | abcam | ab9021 |
| KRT13 | Rabbit | abcam | ab92551 |
| KRT14 | Mouse | abcam | ab7800 |
| Loricrin | Rabbit | Biolegend | 9051011 |
| ITGA6 | Mouse | abcam | Ab20142 |
| NOTCH3 | Rabbit | Cell Signaling | 5276S |
| NICD1/Cleaved NOTCH1 (Val1744) | Rabbit | Cell signaling | 4147S |
| RBPJκ | Rabbit | Cell Signaling | 5313S |

RNA in situ Hybridization

RNA in situ hybridization was performed as previously described (Que et al., 2006). Briefly, embryos were fixed in 4% PFA overnight and embedded in OCT. Cryo-sections were hybridized with specific digoxigenin-labeled riboprobe at 65° C. in a moist chamber, overnight. Sections were then washed in high-stringency conditions and incubated with alkaline phosphatase-conjugated anti-digoxigenin antibody overnight at 4° C. Following a chromogenic reaction with nitro blue tetrazolium/5-bromo-4-chloro-3-indolyl phosphate, in situ gene expression was indicated by the blue color of specific tissue regions. Jag1 and Jag2 probes were kindly provided by Dr. Doris K. Wu (National Institute on Deafness and Other Communicative Disorders) and Dr. Thomas Gridley (Maine Medical Center Research Institute), respectively.

Flow Cytometric Analysis and Cell Sorting

To perform cell surface marker staining, cells were disassociated with 0.05% Trypsin-EDTA (ThermoFisher Scientific) and stained with fluorophore conjugated antibodies in FACS buffer (1×PBS, 2% FBS, 0.2 mM EDTA) for 30 min with live/dead staining dye (LIVE/DEAD™ Fixable Violet Dead Cell Stain Kit, ThermoFisher Scientific) to exclude dead cells. Cell surface marker antibodies are listed in Table 2. Intracellular staining cells were performed according to the manufacturer's instructions in eBioscience™ Foxp3/Transcription Factor Staining Buffer Set (ThermoFisher Scientific). Fixation and permeabilization was performed at room temperature for 1 hour followed by incubation of primary antibody for 1 hour. Cells were washed with 1×PBS and fluorophore-conjugated secondary antibodies were incubated for 1 hour. Stained cells were analyzed BD FACSCanto (BD Biosciences) data were analyzed with FlowJo software (Ashland, Oregon). Sorted EPCAM$^+$ ITGß4$^+$ cells were maintained in the medium containing 5% FBS, 20 ng/ml EGF, 20 ng/ml FGF2 and 10 µM Rock inhibitor Y27632.

RNA Sequencing

RNA was extracted from RUES2-derived esophageal progenitor cells, human fetal (14-18 weeks) and E12.5 mouse esophageal epithelium and skin using the PicoPure™ RNA Isolation Kit (ThermoFisher Scientific). RNA concentration was measured by 2100 Bioanalyzer (Agilent Technologies). Libraries were prepared using Illumina TruSeq RNA prep kit (Illumina) and sequenced by the Illumina HiSeq4000 (Illumina) at the Columbia Genome Center. Samples were multiplexed in each lane, which yields targeted number of single-end/paired-end 100 bp reads for each sample, as a fraction of 180 million reads for the whole lane. RTA (Illumina) was used for base calling and bcl2fastq (version 1.8.4) for converting BCL to fastq format, coupled with adaptor trimming. The reads were mapped to a reference genome (Mouse: UCSC/mm9 and Human: NCBI/build37.2) using Tophat (version 2.1.0) with 4 mismatches and 10 maximum multiple hits. To tackle the mapping issue of reads that are from exon-exon junctions, Tophat inferred novel exon-exon junctions ab initio, and combined them with junctions from known mRNA sequences as the reference annotation. The relative abundance/expression level of genes was estimated and splice isoforms using Cufflinks (version 2.0.2) with default settings. Estimated normalized expression level Fragments Per Kilobase of transcript per Million (FPKM) of known genes and transcripts were presented.

Quantitative Real-Time Polymerase Chain Reaction (qRT-PCR)

Cells were lysed with TRIzol (Invitrogen) and RNA was purified using the RNeasy Mini Kit (QIAGEN). RNA was reversely transcribed to cDNA by the SuperScript III First-Strand SuperMix (Invitrogen). cDNA was quantified by real-time PCR using the iQ SYBR Green Supermix (Bio-Rad) and StepOnePlus™ Real-Time PCR System (Applied Biosystems). The transcript level of each gene was normalized to the ß-actin control using 2(−ΔΔCT) method. Relative gene expression was calculated and reported as fold change compared to the indicated samples using ß-actin normalized transcript level. All qRT-PCR experiments were performed at least triplicate. PCR primers were designed and produced by Integrated DNA Technologies and primer sequences were summarized in Table 3.

Statistical Analysis

Data are presented as the mean±SEM using GraphPad Software Prism 6. Statistical significance was determined by Student's t tests. When more than two groups are compared, multiple comparisons were performed using one-way ANOVA followed by Bonferroni correction. For each analysis, at least 3 biological replicates were included. Representative pictures shown are indicated in the legends. P-values of 0.05 or less were considered to be statistically significant.

TABLE 3 qRT-PCR primer sequences

| Gene | Forward primers | Reverse primers |
|---|---|---|
| p63 | TTCGGACAGTACAAAGAACGG (SEQ ID NO: 1) | GCATTTCATAAGTCTCACGGC (SEQ ID NO: 2) |
| NKX2.1 | CAGGACACCATGAGGAACAG (SEQ ID NO: 3) | TCATGTTCATGCCGCTCG (SEQ ID NO: 4) |
| SOX2 | CACACTGCCCCTCTCAC (SEQ ID NO: 5) | TCCATGCTGTTTCTTACTCTCC (SEQ ID NO: 6) |
| NANOG | GAAATACCTCAGCCTCCAGC (SEQ ID NO: 7) | GCGTCACACCATTGCTATTC (SEQ ID NO: 8) |
| FOXA2 | CTGGTCGTTTGTTGTGGC (SEQ ID NO: 9) | TTCATGTTGCTCACGGAGG (SEQ ID NO: 10) |
| FOXA1 | AGGGCTGGATGGTTGTATTG (SEQ ID NO: 11) | TGAGTTCATGTTGCTGACCG (SEQ ID NO: 12) |
| SOX9 | ACTTGCACAACGCCGAG (SEQ ID NO: 13) | CTGGTACTTGTAATCCGGGTG (SEQ ID NO: 14) |
| PAX9 | GGTGAACGGGTTGGAGAAG (SEQ ID NO: 15) | CTGTAGGTCATGTAAGGCGAC (SEQ ID NO: 16) |
| KRT4 | AGCTAGATACCTTGGGCAATG (SEQ ID NO: 17) | CACAAAGTCATTCTCGGCTG (SEQ ID NO: 18) |
| KRT5 | AGAGCTGAGAAACATGCAGG (SEQ ID NO: 19) | AGCTCCACCTTGTTCATGTAG (SEQ ID NO: 20) |
| KRT7 | CAGGATATGGCACGGCAG (SEQ ID NO: 21) | CACAGAGATATTCACGCTCC (SEQ ID NO: 22) |
| KRT13 | AAGACCATTGAAGAGCTCCG (SEQ ID NO: 23) | TGGCATTGTCAATCTCCAGG (SEQ ID NO: 24) |
| KRT14 | GAAGTGAAGATCCGTGACTGG (SEQ ID NO: 25) | GCAGAAGGACATTGGCATTG (SEQ ID NO: 26) |
| INVOLUCRIN | CTGCCTCAGCCTTACTGTG (SEQ ID NO: 27) | GCTCCTGATGGGTATTGACTG (SEQ ID NO: 28) |
| FOXE1 | GAGCCTGCTACAACCCTG (SEQ ID NO: 29) | TGTGTCTATGAGTTTTCGTCCC (SEQ ID NO: 30) |
| JAG1 | GGACTATGAGGGCAAGAACTG (SEQ ID NO: 31) | AAATATACCGCACCCCTTCAG (SEQ ID NO: 32) |
| JAG2 | CAGGAAGTGATCGGGTTCG (SEQ ID NO: 33) | CAGACAAGGCTTCCATCCG (SEQ ID NO: 34) |
| HES5 | CTACCTGAAGCACAGCAAAG (SEQ ID NO: 35) | AGCTTCATCTGCGTGTCG (SEQ ID NO: 36) |
| HEY1 | TGGTACCCAGTGCTTTTGAG (SEQ ID NO: 37) | CTCCGATAGTCCATAGCAAGG (SEQ ID NO: 38) |
| HEY2 | ATTATAGAGAAAAGGCGTCGGG (SEQ ID NO: 39) | GCATCTTCAAATGATCCACTGTC (SEQ ID NO: 40) |
| AXIN2 | TGTCCAGCAAAACTCTGAGG (SEQ ID NO: 41) | GTGCAAAGACATAGCCAGAAC (SEQ ID NO: 42) |
| p21 | TGTCACTGTCTTGTACCCTTG (SEQ ID NO: 43) | GGCGTTTGGAGTGGTAGAA (SEQ ID NO: 44) |
| COL1A1 | CCCCTGGAAAGAATGGAGATG (SEQ ID NO: 45) | TCCAAACCACTGAAACCTCTG (SEQ ID NO: 46) |
| HNF6A | GAGGATGTGGAAGTGGCTG (SEQ ID NO: 47) | ACATCTGTGAAGACCAACCTG (SEQ ID NO: 48) |
| ID2 | CATCCCACTATTGTCAGCCTG (SEQ ID NO: 49) | AGAAGGGAATTCAGAAGCCTG (SEQ ID NO: 50) |
| JUNB | GGACACGCCTTCTGAACG (SEQ ID NO: 51) | CGGAGTCCAGTGTGGTTTG (SEQ ID NO: 52) |
| KLF4 | ACCTACACAAAGAGTTCCCATC (SEQ ID NO: 53) | TGTGTTTACGGTAGTGCCTG (SEQ ID NO: 54) |
| KLF5 | GAAGGAGTAACCCCGATTTGG (SEQ ID NO: 55) | CTTCCCAGGTACACTTGTATGG (SEQ ID NO: 56) |
| LEF1 | AGACAAGCACAAACCTCTCAG (SEQ ID NO: 57) | TCATTATGTACCCGGAATAACTCG (SEQ ID NO: 58) |
| NKD1 | CTCGCCGGGATAGAAAACTAC (SEQ ID NO: 59) | GGTGTGGGATGTGGATGG (SEQ ID NO: 60) |
| P15 | GTTAAGTTTACGGCCAACGG (SEQ ID NO: 61) | ACCTTCTCCACTAGTCCCC (SEQ ID NO: 62) |
| PROX1 | TTTTATACCCGTTATCCCAGCTC (SEQ ID NO: 63) | TGCGTACTTCTCCATCTGAATG (SEQ ID NO: 64) |
| TNFB1 | GTCTACACAGTCTTTGCTCCC (SEQ ID NO: 65) | TCCGCTAACCAGGATTTCATC (SEQ ID NO: 66) |
| WNT5A | TCGCCCAGGTTGTAATTGAAG (SEQ ID NO: 67) | TGAGAAAGTCCTGCCAGTTG (SEQ ID NO: 68) |

Example 2—Sequential Differentiation of hPSCs Towards Esophageal Progenitor Cells Requires the Inhibition of TGFß and BMP Signaling The inventors have previously demonstrated that Noggin expression is localized in the dorsal foregut endoderm where progenitor cells for the esophageal epithelium arise (Que et al., 2006). The unique expression of Noggin in the dorsal foregut was maintained at E10.5 and E11.5, but it is absent at E12.5 (FIG. 1A). A BRE-lacZ transgenic reporter mouse line in which ß-gal expression is regulated by BMP response elements (BREs) from the human ID1 gene was also used to determine BMP activity (Blank et al., 2008). Consistently, BMP activation was limited to the ventral side of the anterior foregut where lung and trachea arise (FIG. 1A). These findings suggested that inhibition of BMP signaling was required for the specification of EPCs from the AFE.

In addition, previous studies have shown that inhibition of TGFß signaling is required for esophageal development and EPC maintenance in adults (DeWard et al., 2014; Mou et al., 2016; Wang et al., 2006). These findings prompted the testing of whether inhibition of BMP and TGFß signaling promotes the specification of AFE towards EPCs.

A previous protocol was used to differentiate the ES cell line RUES2 cells into the endoderm with a combination of Activin A, BMP4, FGF2 and the ROCK inhibitor Y-27632 (day 1-4) (FIGS. 1B-C) (Huang et al., 2015; Huang et al., 2014). Noggin and SB431542 was used to block BMP and TGFß signaling, respectively (day 4-5), followed by a one-day treatment of SB431542 and the WNT/ß-catenin inhibitor IWP2 to promote the formation of AFE (Huang et al., 2015; Huang et al., 2014). From day 6 to day 16, Noggin and SB431542 were re-applied to the culture to block BMP and TGFß signaling. Cells were then maintained in the serum-free differentiation medium (SFD) to allow full commitment until day 24 (FIGS. 1B-C). During the initial differentiation the transcript levels of the pluripotent markers NANOG and SOX2 decreased concomitantly with increased levels of the endodermal marker FOXA2 (FIG. 1D). However, the levels of SOX2 increased at day 16, indicating specification towards the dorsal foregut endoderm which serves as progenitor cells for the esophagus (FIG. 1D). Consistently, increased levels of p63, PAX9 and FOXE1 were observed (FIG. 1D), genes expressed in the developing mouse embryonic esophageal epithelium (Dathan et al., 2002; Peters et al., 1998), suggesting that inhibition of BMP and TGFß signaling drives the differentiation of AFE towards the esophageal lineage. Of note is that the transcripts of these genes are all similarly enriched in the epithelium of human fetal esophagus (FIG. 1D). p63+ cells were first detected by immunostaining at day 10 of differentiation, co-expressing FOXA2, PAX9 and FOXE1 (results not shown). The transcript levels of KLF4, KLF5 and WNT5A, critical factors in regulating esophageal epithelial proliferation and differentiation (Goldstein et al., 2007; Okano et al., 2000; Tetreault et al., 2016), also increased upon differentiation (FIG. 1G).

Also noted was that the levels of SOX2 were reduced at day 4 along with NANOG but increased at day 16 during commitment to EPCs. FOXA2 expression indicates hESC differentiation into the endodermal lineage. Notably, Noggin treatment alone at day 6-16 was insufficient to promote AFE differentiation into p63$^+$ NKX2.1$^-$ EPCs (FIG. 1E). Taken together, these results emphasized the importance of BMP and TGFß inhibition for the commitment of AFE towards EPCs.

WNT has been shown to play an important role in the foregut patterning into different organs including thyroid, lung, stomach, liver and pancreas in mouse development and hPSC differentiation (Goss et al., 2009; Harris-Johnson et al., 2009; Longmire et al., 2012; McCracken et al., 2017; Ober et al., 2006; Wells et al., 2007). Previous studies revealed that WNT signaling is inactive during dorsal foregut commitment to the esophagus at E9.5 (Jacobs et al., 2012). Consistently, the transcript levels of the WNT downstream targets AXIN2, LEF1 and NKD1 were low (FIG. 1H), suggesting low WNT signaling activities during the specification of EPCs. In addition, treatment with the WNT inhibitor DKK1 alone was insufficient to promote p63 expression in hPSCs (FIG. 1E), and the presence of WNT inhibitor IWP2 in culture treated with Noggin and SB431542 at day 6-16 did not further promote p63 expression (FIG. 1I).

These data are consistent with the finding that WNT loss of function does not affect esophageal development in mice (Goss et al., 2009; Harris-Johnson et al., 2009). By contrast, activation of WNT signaling by a GSK inhibitor reduced p63 expression in a dose-dependent manner (FIG. 1F), which is consistent with the finding that ectopic WNT activation inhibits squamous cell specification in the mouse esophagus and forestomach which is also lined by the stratified squamous epithelium (Goss et al., 2009; Harris-Johnson et al., 2009). Notably, while the levels of the general foregut marker SOX2 remained unchanged, the levels of the posterior foregut markers PROX1 and HNF6 increased upon WNT activation (FIG. 1F) (Burke and Oliver, 2002; Rausa et al., 1997), indicating that ectopic WNT activation in the presence of Noggin and SB431542 posteriorizes the foregut reminiscent of the role of WNT signaling in promoting the development of posterior foregut organs such as liver and pancreas (Ober et al., 2006; Wells et al., 2007).

Together these data suggested that maintaining WNT at low activities facilitates the specification of AFE towards the EPC lineage.

Figure 2A:
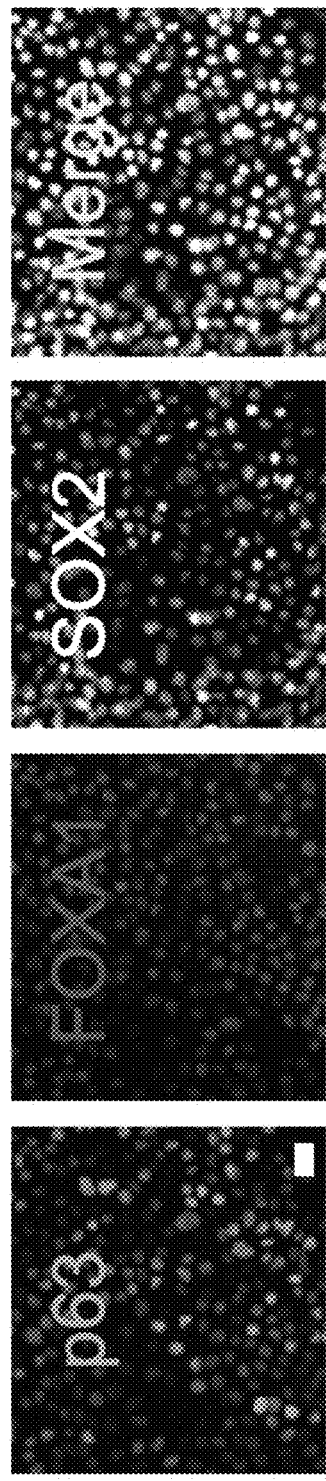
Figure 2B:
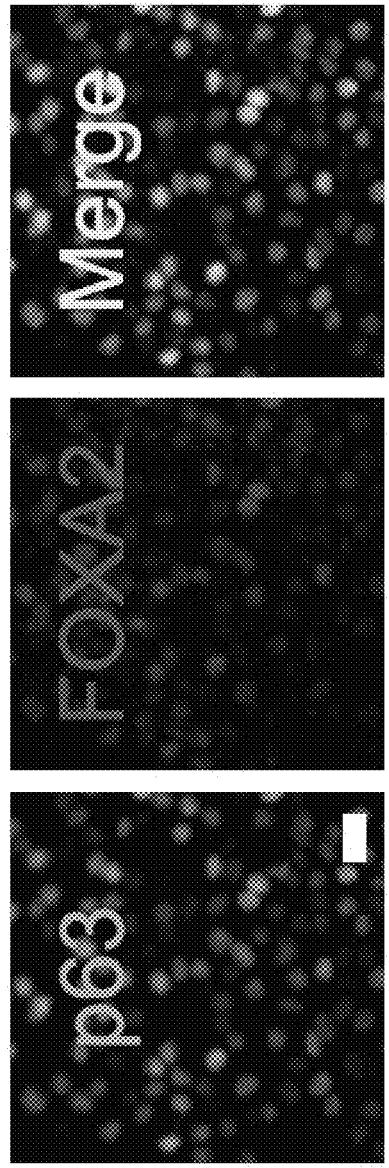
Figure 2C:
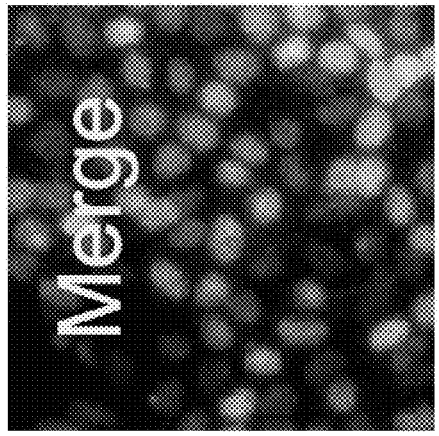
Figure 2C:
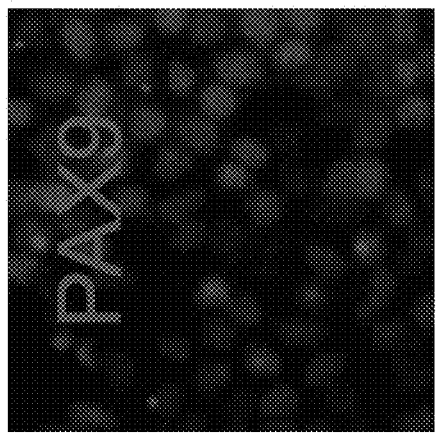
Figure 2C:
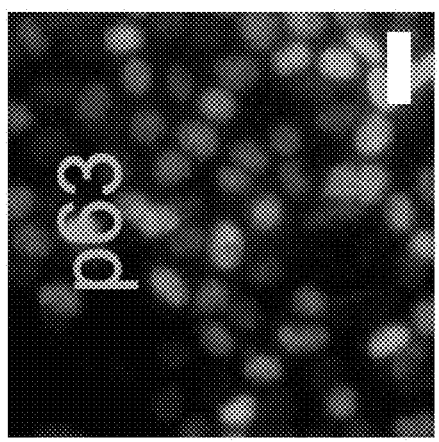
Figure 2D:
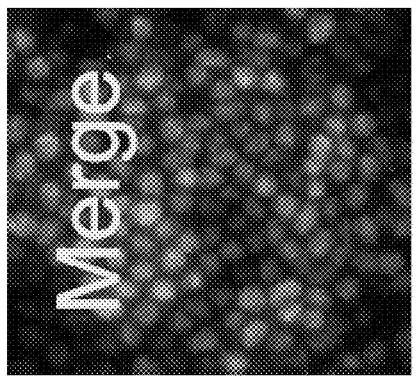
Figure 2D:
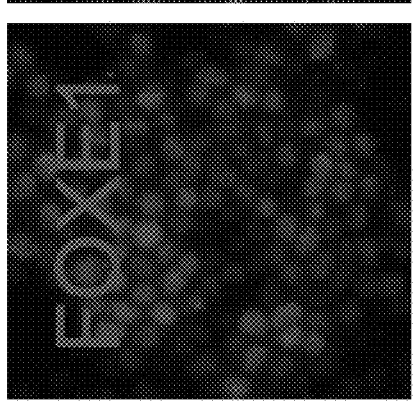
Figure 2D:
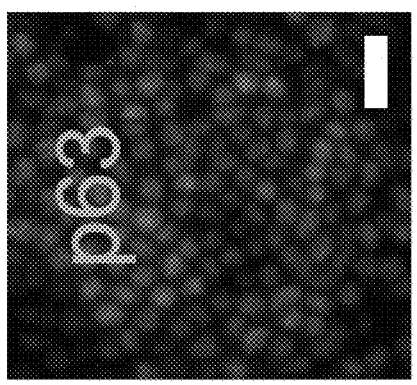
Figure 2E:
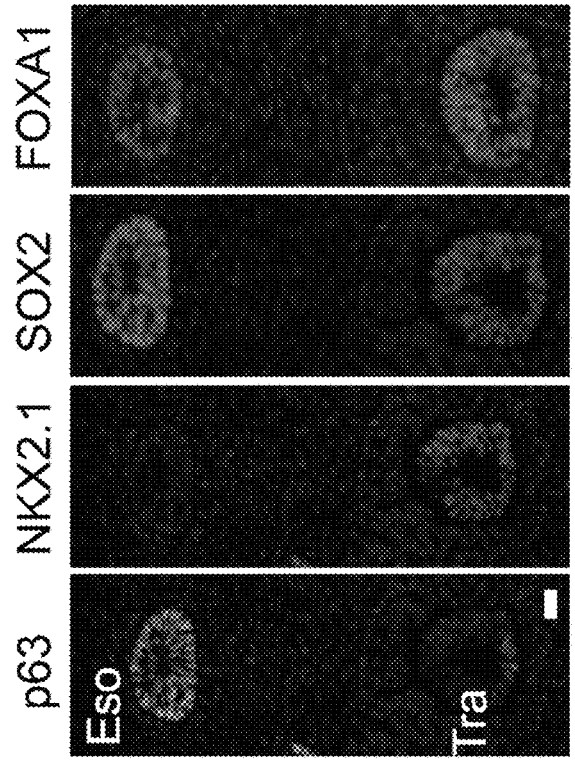
Figure 2F:
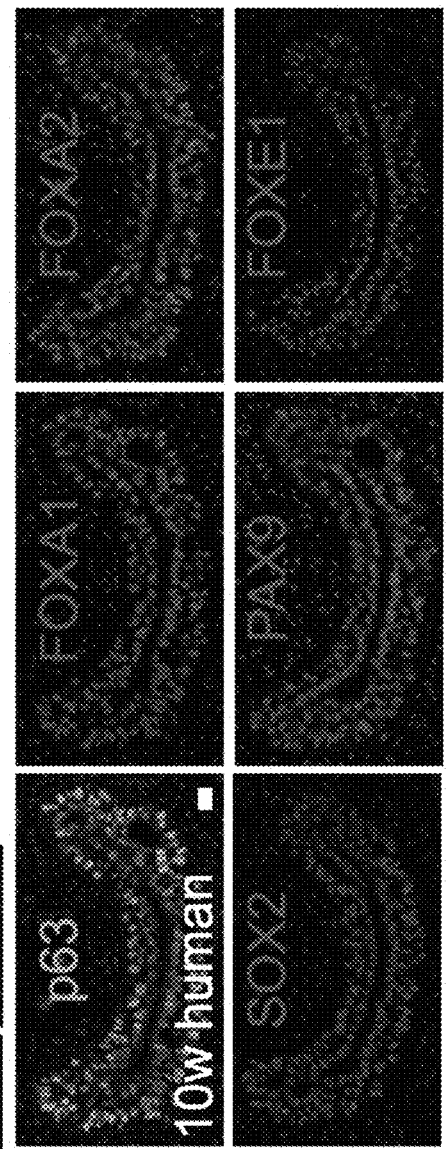
Figure 2G:
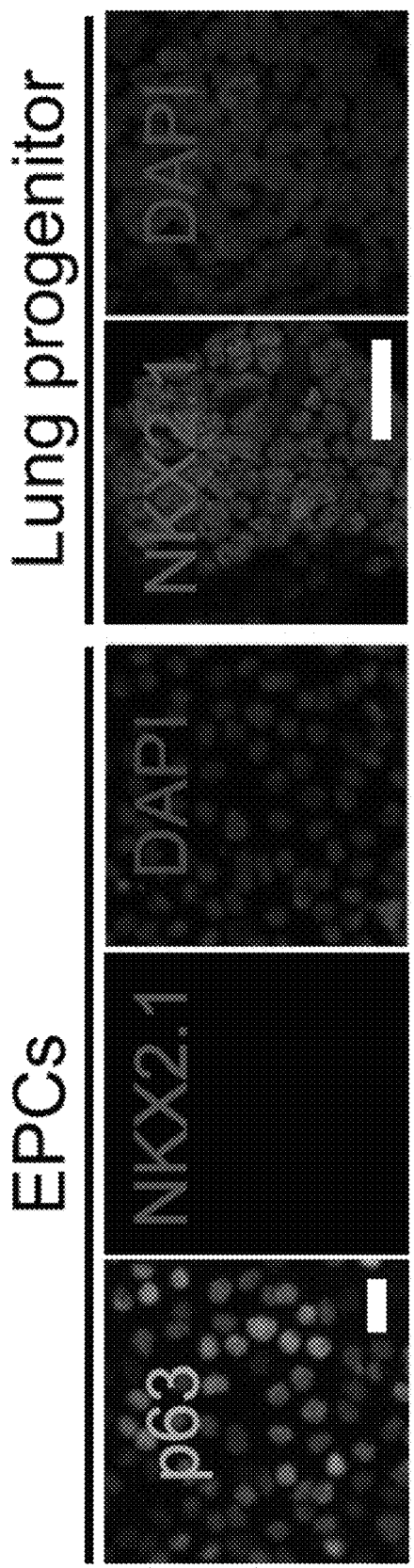
Figure 2H:
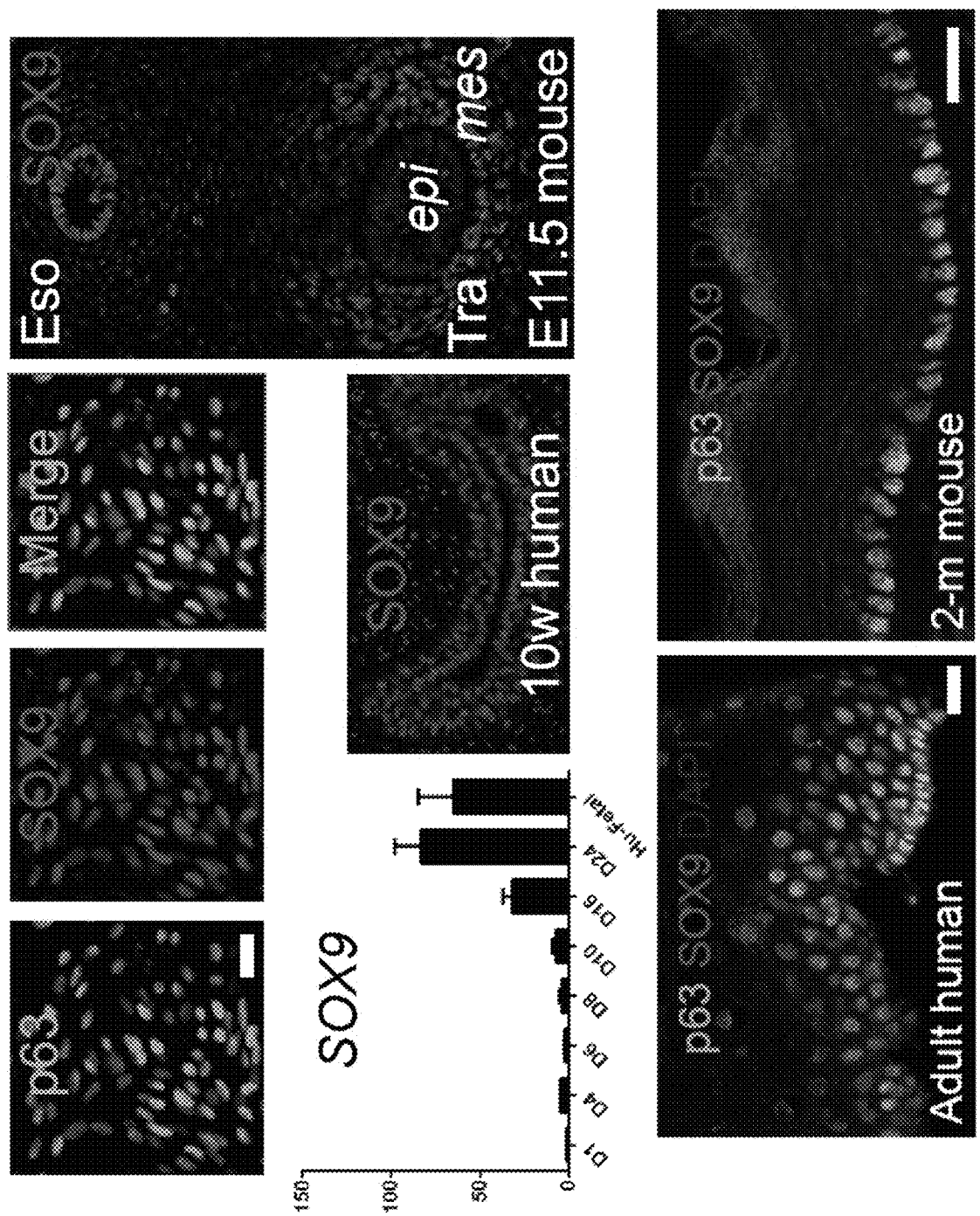
Figure 2I:
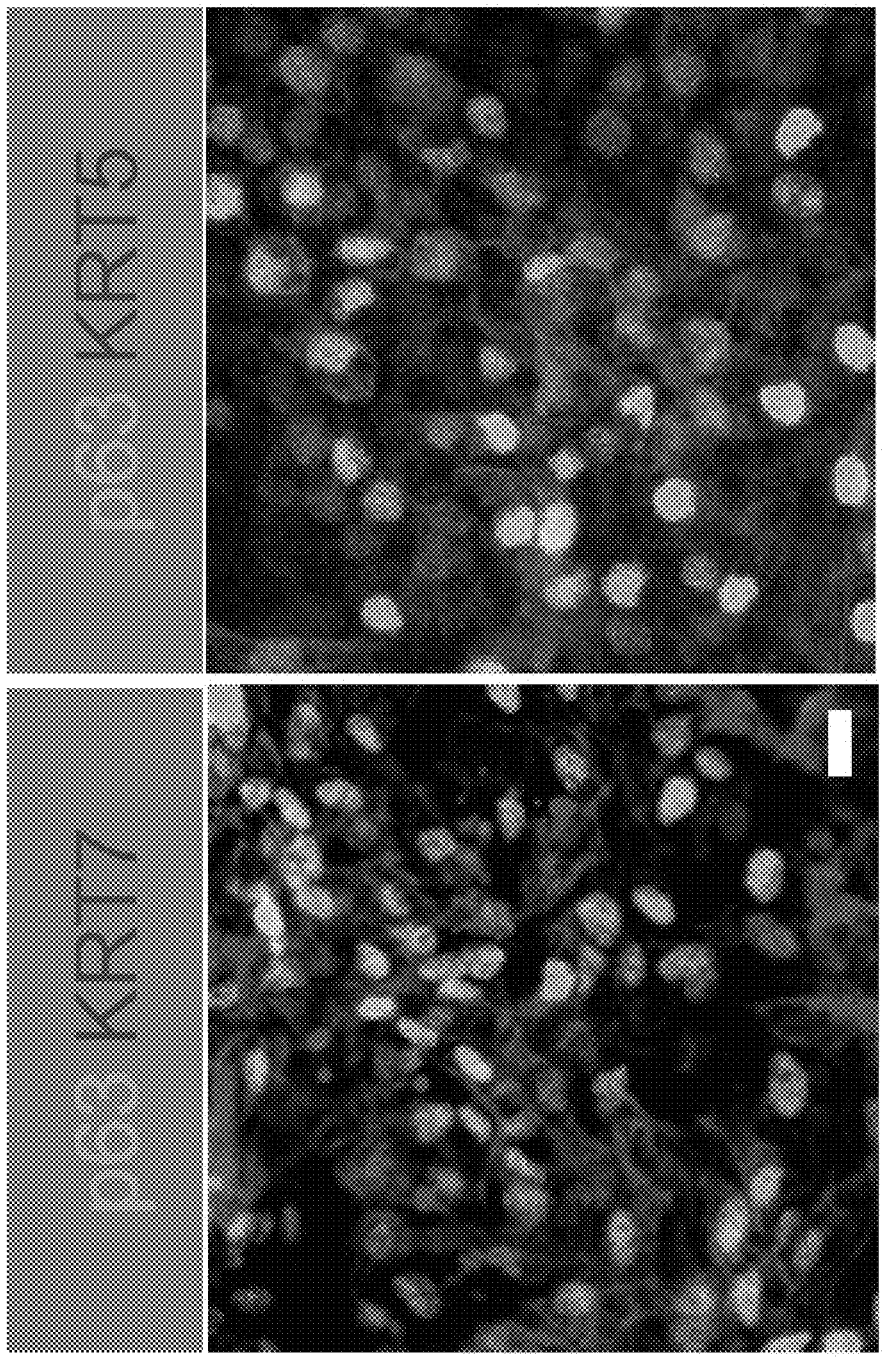
Figure 2J:
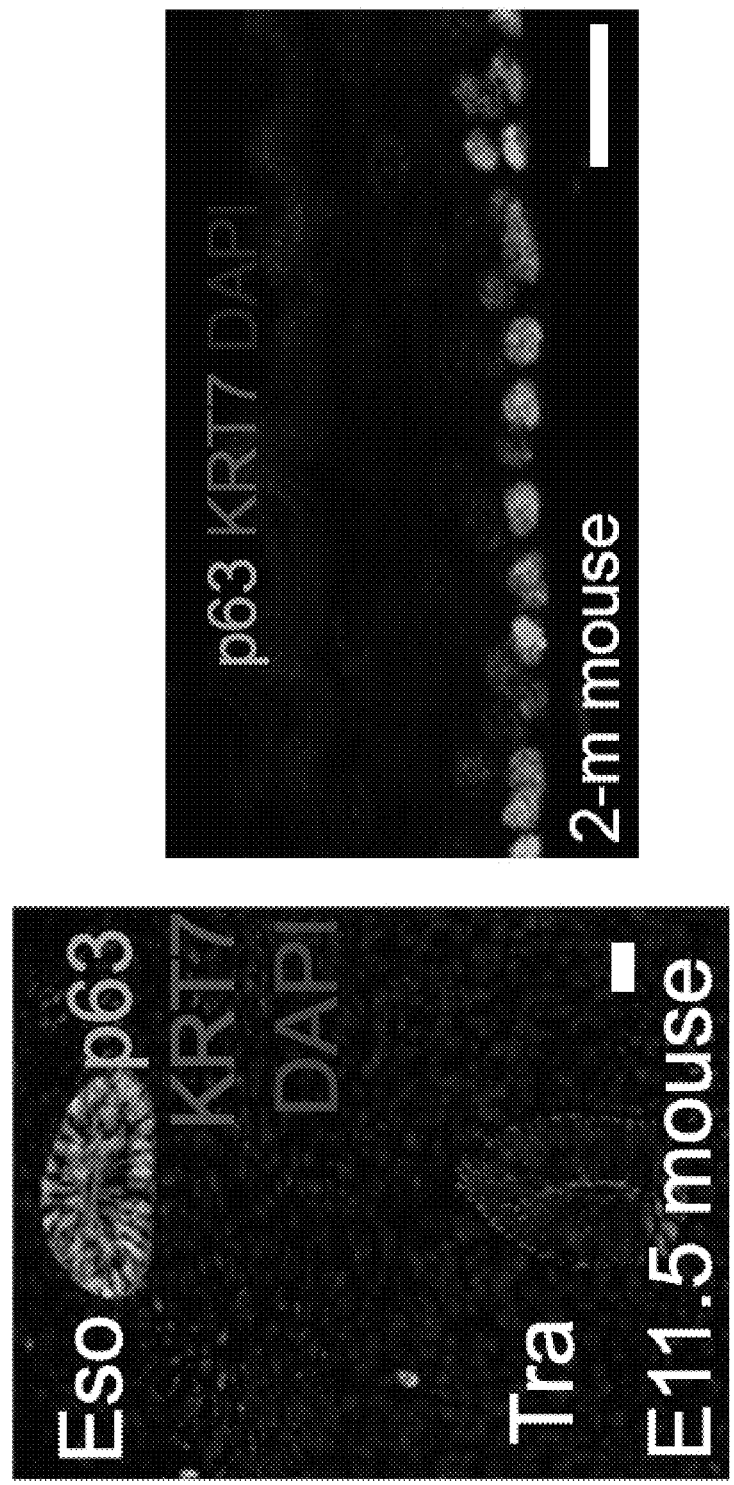
Figure 2K:
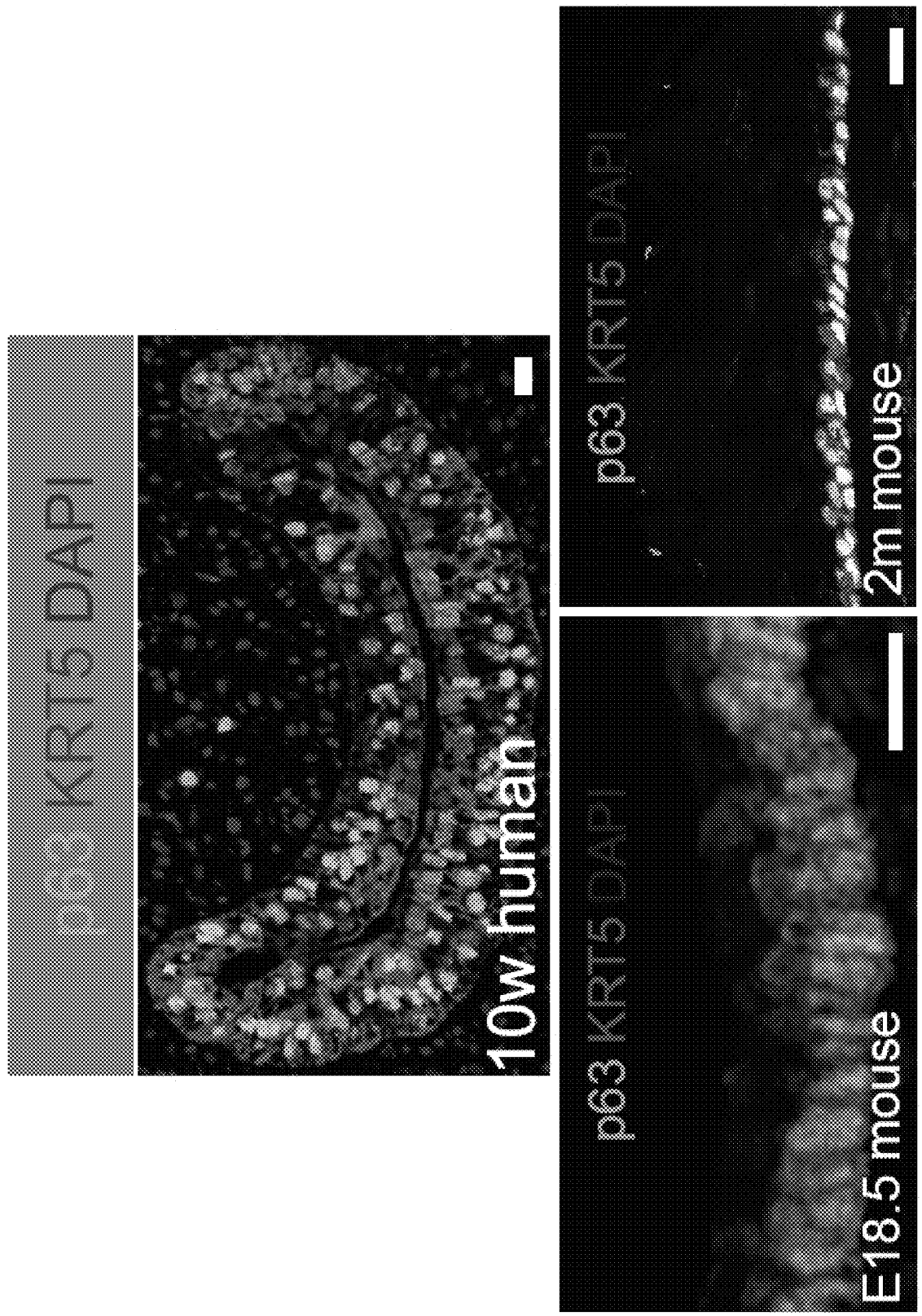

Example 3—hPSC-Derived EPCs Expressed SOX9 and KRT7, Characteristics of the Developing Human and Mouse Esophagus Transcript analysis showed that hESC-derived EPCs express endodermal and esophageal progenitor markers such as FOXE1, FOXA2, SOX2 and p63 (FIG. 1D). Immunostaining confirmed strong expression of these transcription factors at day 24 (FIGS. 2A-D). These transcription factors were also present in the epithelium of the developing human fetal esophagus (FIG. 2F). Intriguingly, immunostaining analysis indicated that the hESC-derived EPCs also expressed SOX9 (FIG. 2H), a transcription factor considered as a specific marker for the distal lung epithelium and tracheal cartilage cells (Chang et al., 2013; Rockich et al., 2013). These findings prompted the examination of whether SOX9 was also expressed in the embryonic esophagus. SOX9 proteins were found to also be present in the developing human fetal (10 weeks) and mouse (E11.5) esophagus, but not in their adult counterpart (FIG. 2H). In addition, the transcription factors PAX9 and FOXE1 that are present in the mouse embryonic esophageal epithelium (Dathan et al., 2002; Peters et al., 1998), were also expressed by hPSC-derived EPCs (FIGS. 2C and 2D) and human fetal esophagus (FIG. 2F). In addition, hESC-derived EPCs also expressed high levels of the intermediate filament protein KRT7 and KRT5 (FIGS. 2I and 2J). While KRT7 was specifically expressed in the embryonic mouse but not adult esophagus (FIG. 2J), KRT5 was expressed in both the fetal and adult mouse esophagus (FIG. 2K). Of note, NKX2.1 was not detected in EPCs (FIG. 2G), excluding the lung and thyroid lineages and confirming that these progenitor cells were esophageal lineage. A previous study showed that NANOG is expressed in the basal cells of the adult mouse esophagus (Piazzolla et al., 2014). However, NANOG expression was not seen in EPCs (results not shown).

These findings suggested that the hESC-derived EPCs mimic human esophageal progenitor cells at the embryonic stage.

Figure 2L:
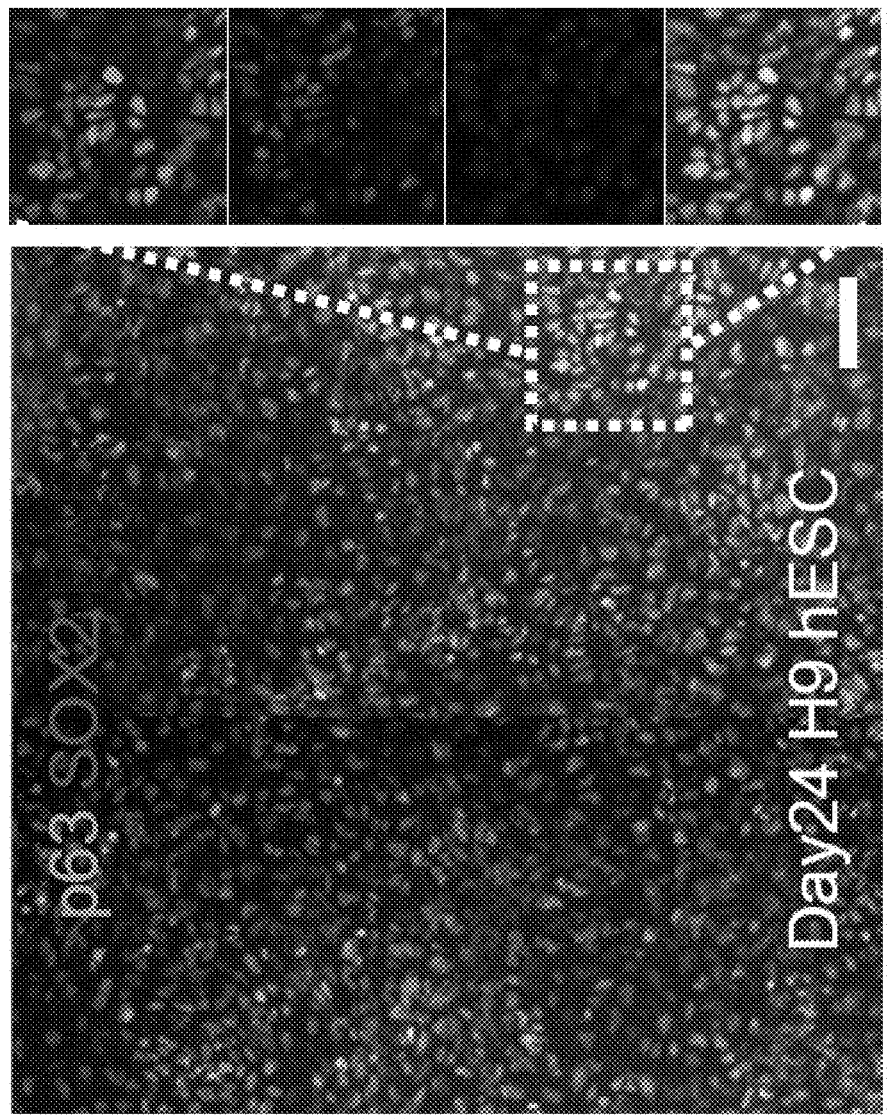

Furthermore, EPCs can also be reproducibly generated from the hESC cell line H9 using the same protocol (FIG. 2L).

Figure 3A:
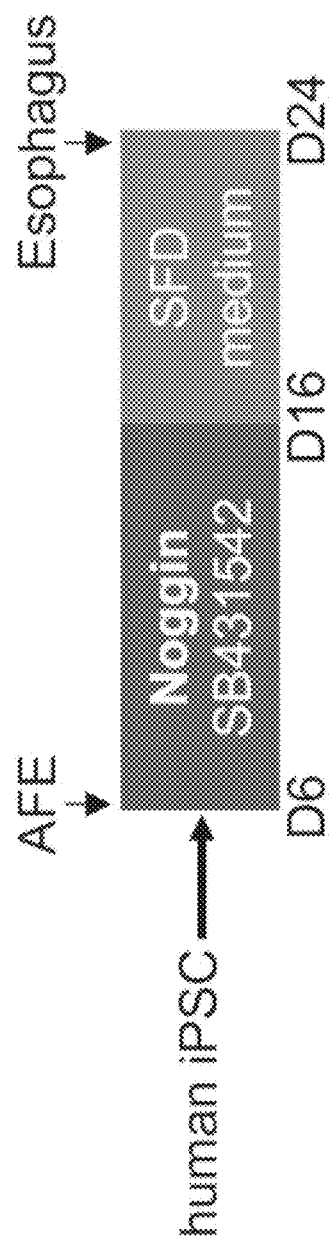
Figure 3B:
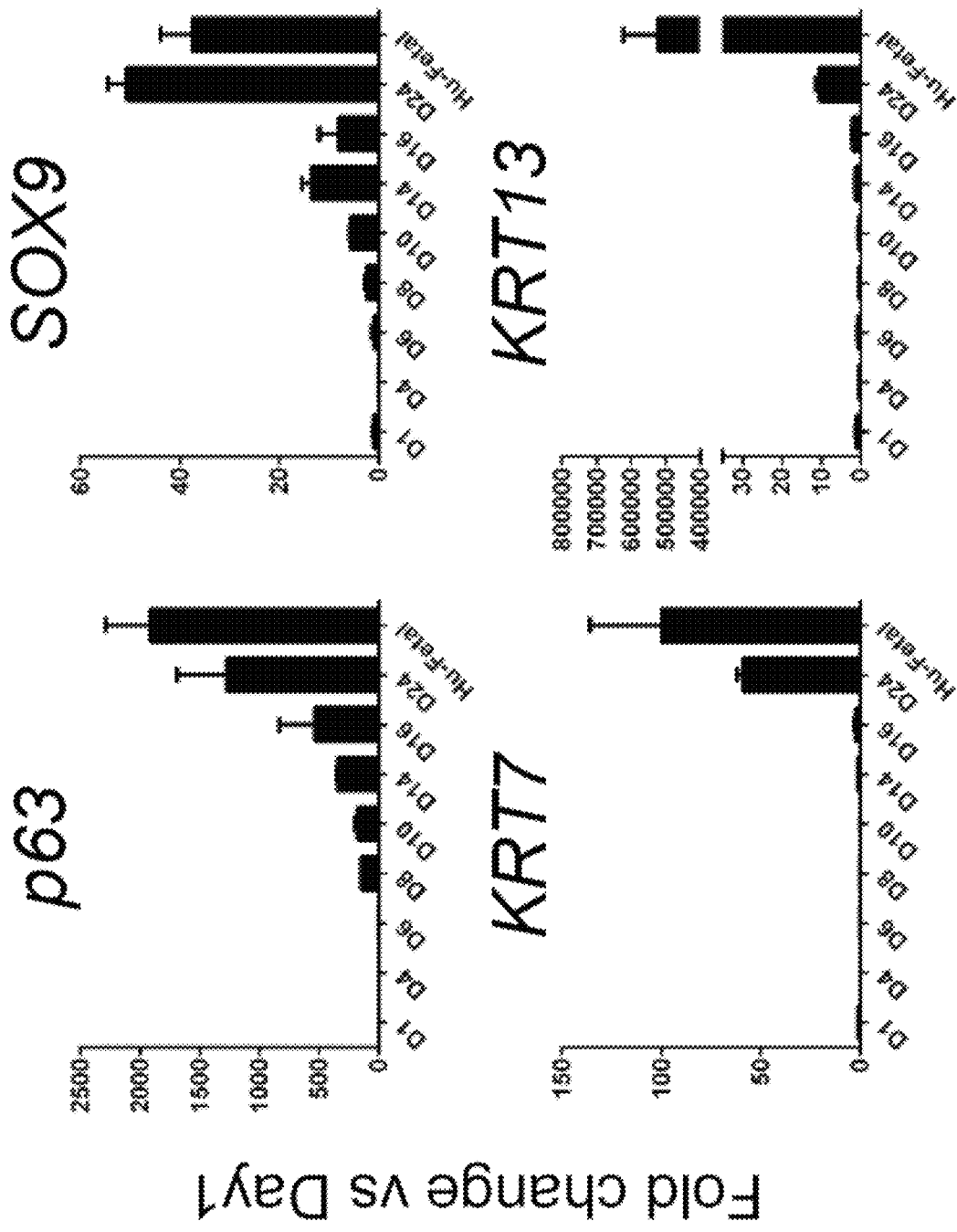
Figure 3B:
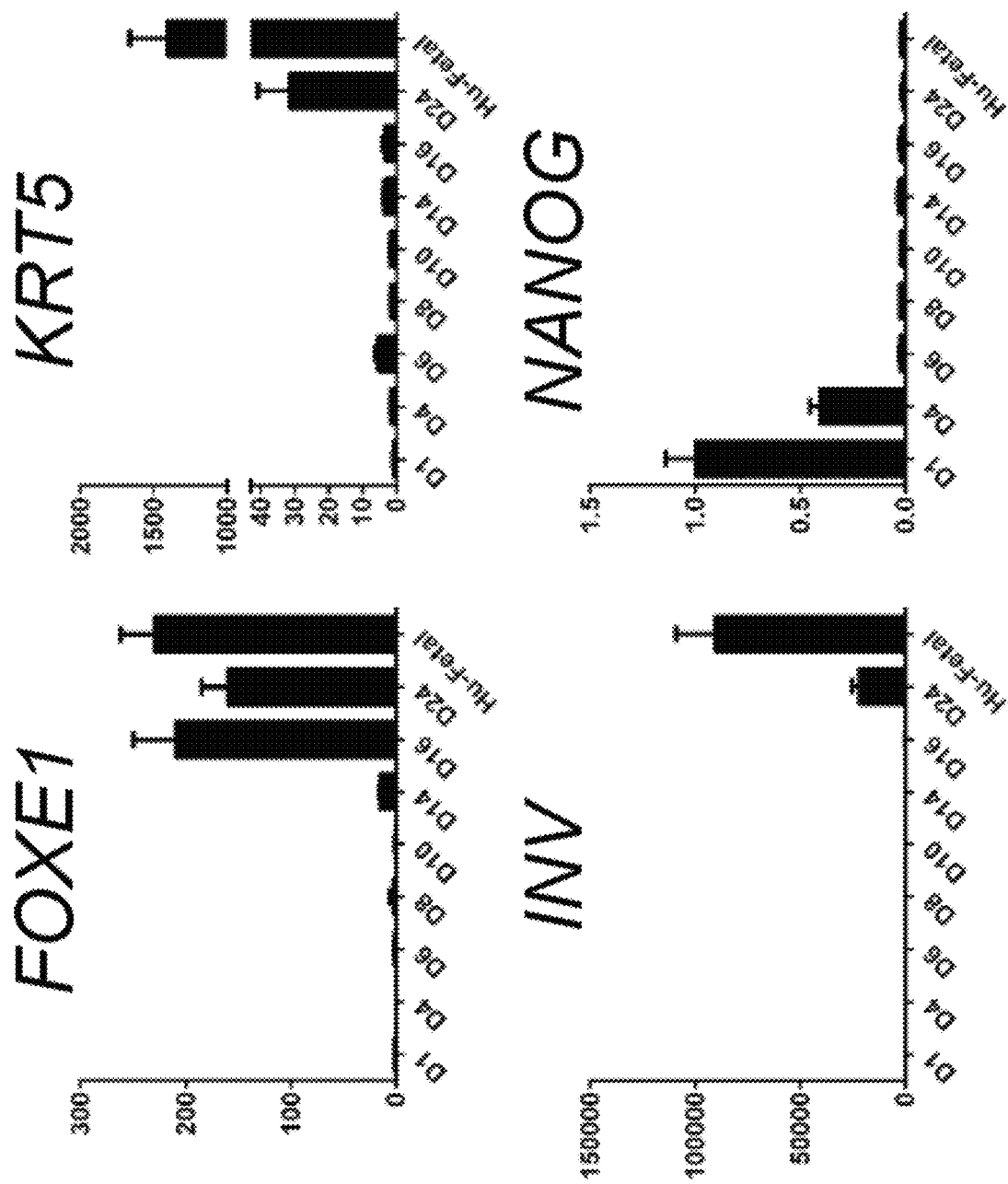
Figure 3E:
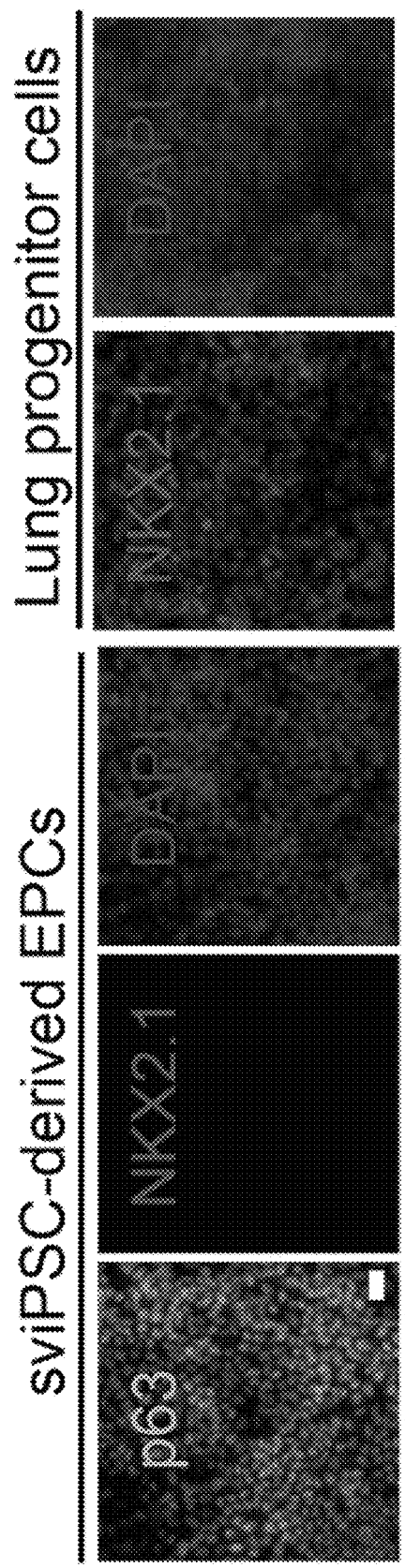
Figure 3G:
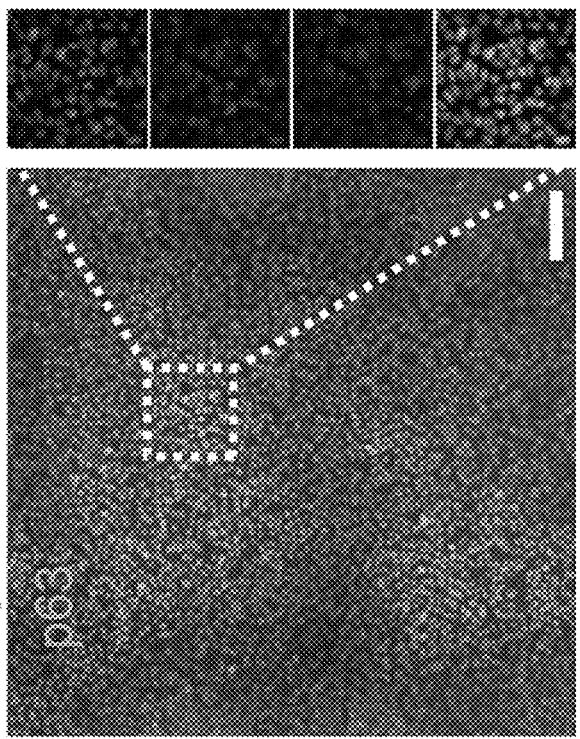
Figure 3F:
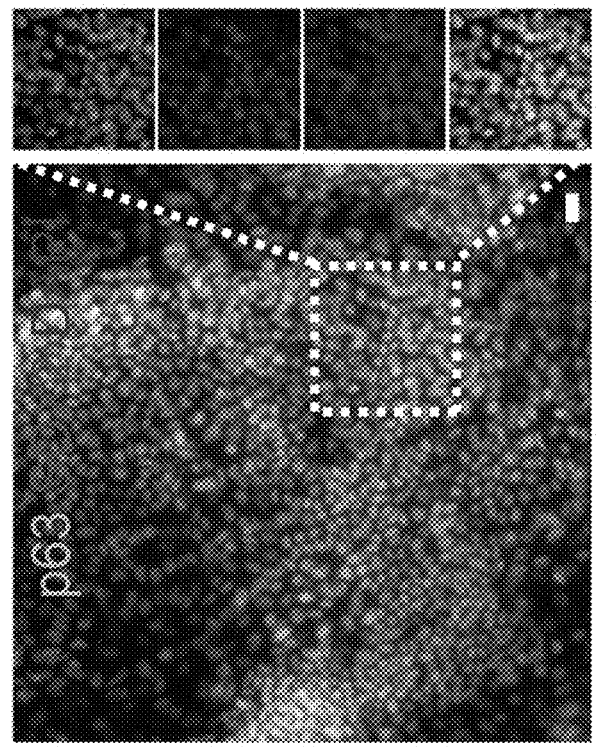

Next it was asked whether iPSC-derived EPCs also exhibit similar characteristics. The iPSC line sviPS efficiently gave rise to EPCs using the same protocol above (FIG. 3A). Importantly, iPSC-derived EPCs also expressed transcripts and proteins of p63, SOX2, FOXA2, SOX9, KRT7 and KRT5 (FIGS. 3B-F) as seen in hESC-derived EPCs. Similarly, NKX2.1 expression was not detected in the progenitor cells (FIG. 3E), confirming that they are not respiratory cells.

Example 4—Purification of hESC-Derived EPCs with the Cell Surface Markers EPCAM and ITGß4

Figure 4B:
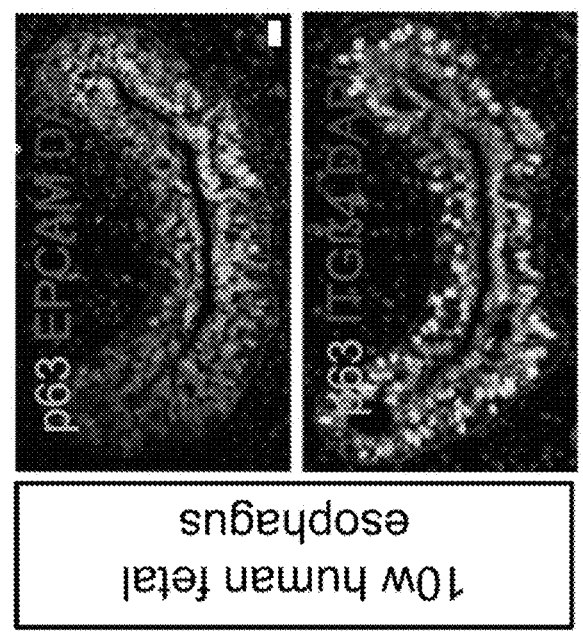
Figure 4A:
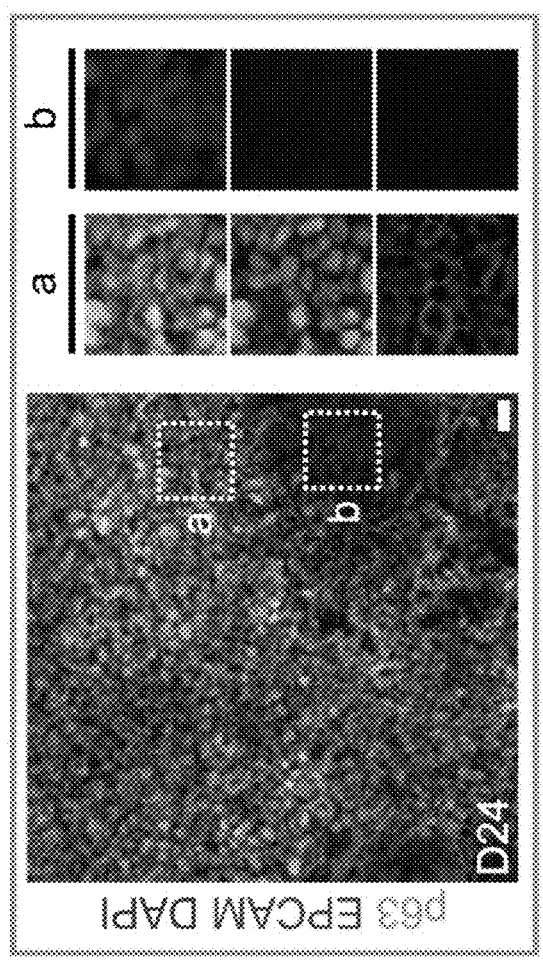
Figure 4C:
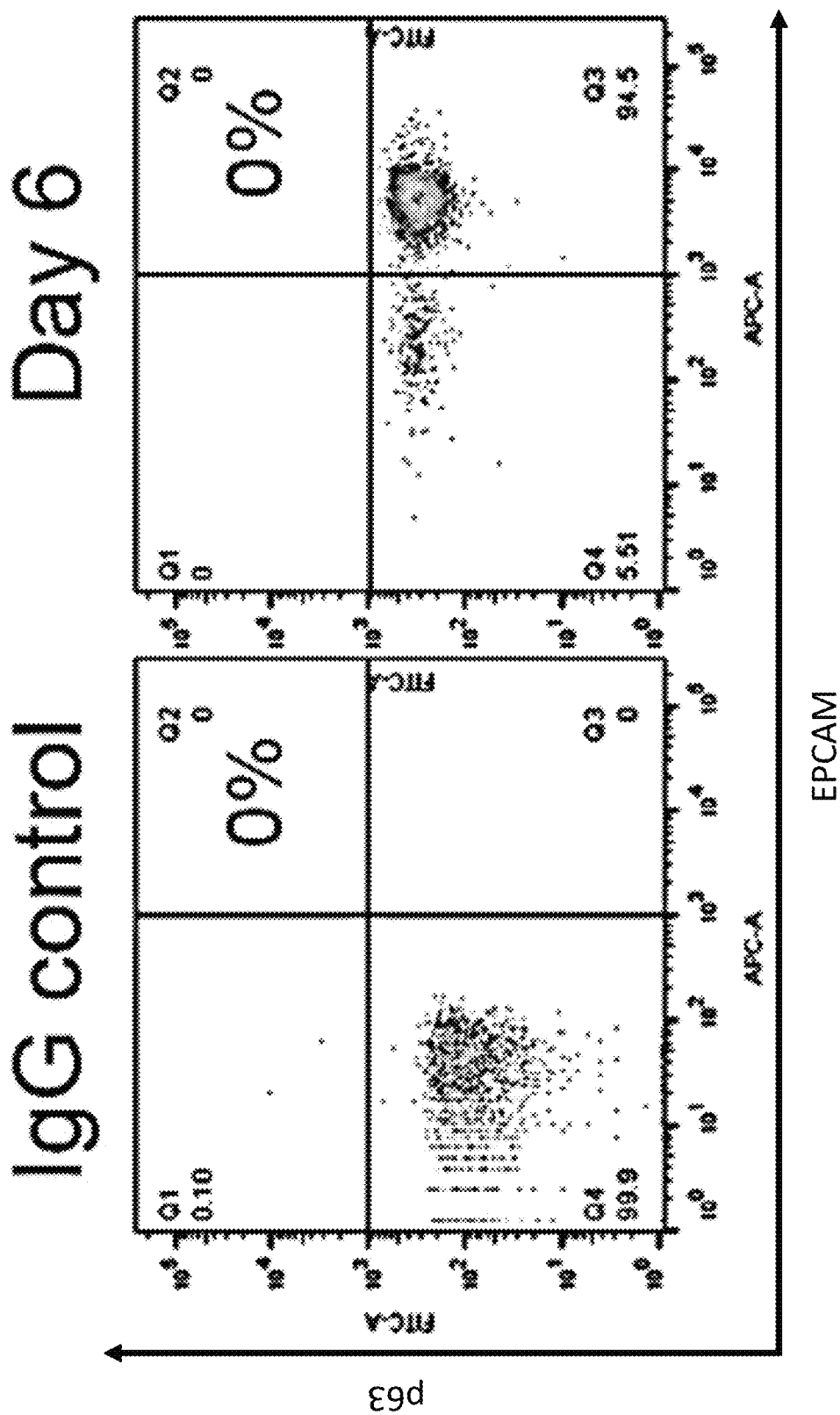
Figure 4C:
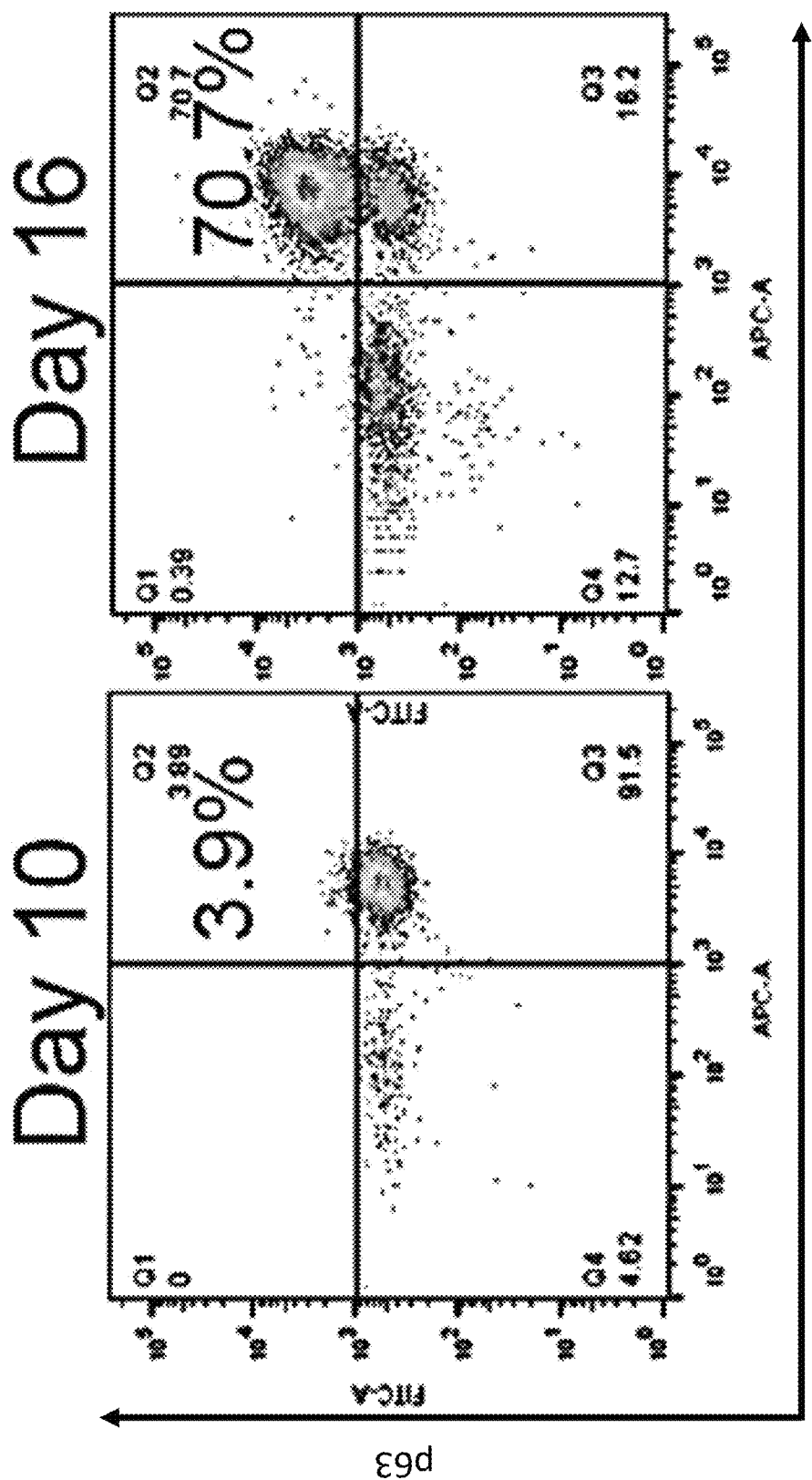
Figure 4C:
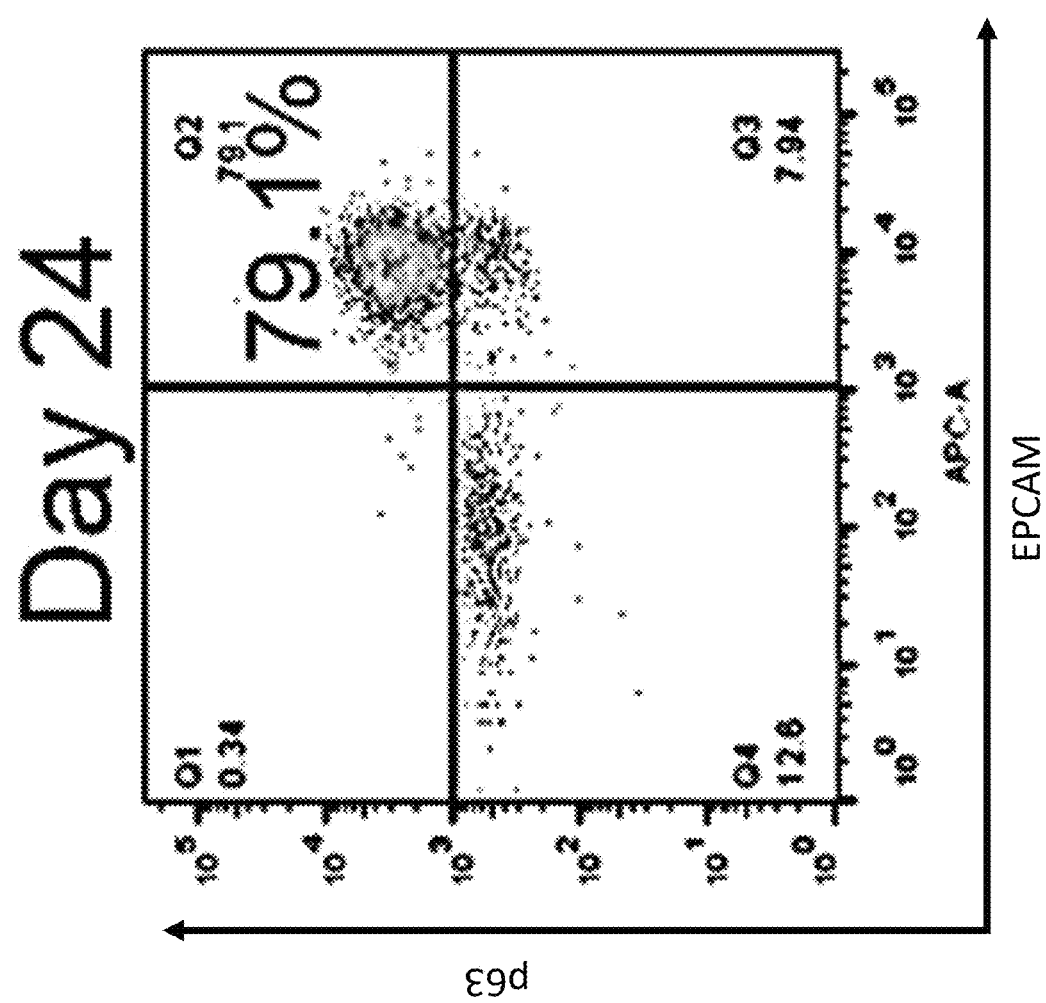
Figure 4C:
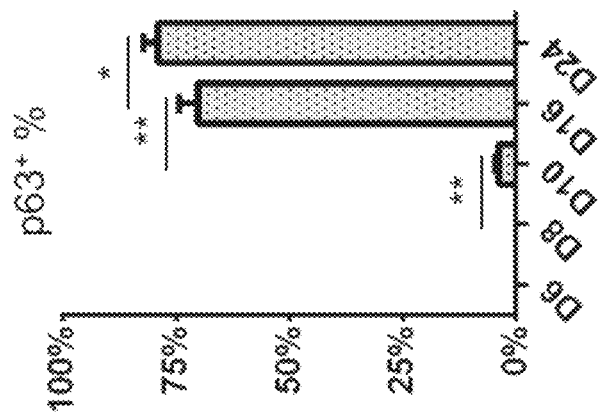

A mixture of epithelial (EPCAM+) and non-epithelial (EPCAM−) cells in the culture differentiated for 24 days was observed (FIG. 4A). If the epithelial cells were not isolated, the highly proliferative non-epithelial cells quickly overgrew and occupied the whole culture dish (data not shown). Previously the cell surface markers CD47 and CD26 were used for the prospective isolation of iPSC-derived thyroid progenitor cells during differentiation (Hawkins et al., 2017). It was asked whether hESC-derived EPCs can also be isolated with cell surface proteins. Multiple markers including p75, integrin a6, 131 and 134, CD34 and CD73 have been used to enrich stem/progenitor cells in the adult mouse and human esophagus (Barbera et al., 2015; DeWard et al., 2014; Kalabis et al., 2008). Some of these markers including p75 are also expressed in other cell lineages (e.g. neural) which introduced contamination in FACS analysis (data not shown).

Interestingly, the epithelial cells (EPCAM+) in the human fetal esophagus expressed integrin 134 (ITGß4) (FIG. 4B). EPCAM is also co-expressed with p63 in the E11.5 mouse esophageal epithelium. EPCAM magnetic beads were used to isolate epithelial cells from the ESC culture at day 24 of differentiation. In an initial experiment, it was found that the EPCAM− isolated cells increased to 79+3.2% p63+ cells from day 10 to day 24 (FIG. 4C), suggesting that the EPC derivation protocol is highly efficient. Similarly, the yield of EPCAM+p63+ cells in H9 hESC culture was 80.6±4.2% (FIG. 4E). The EPC derivation efficiency for iPSC lines was also high although the efficiency for mRNA iPSC was relatively lower (FIGS. 4F and 4G). At day 24 of differentiation the yield of p63+ EPCAM+ cells for sviPSC and mRNA iPSC was 80.2±6.5% and 50.1±3.5%, respectively (FIGS. 4F and 4G).

Figure 4D:
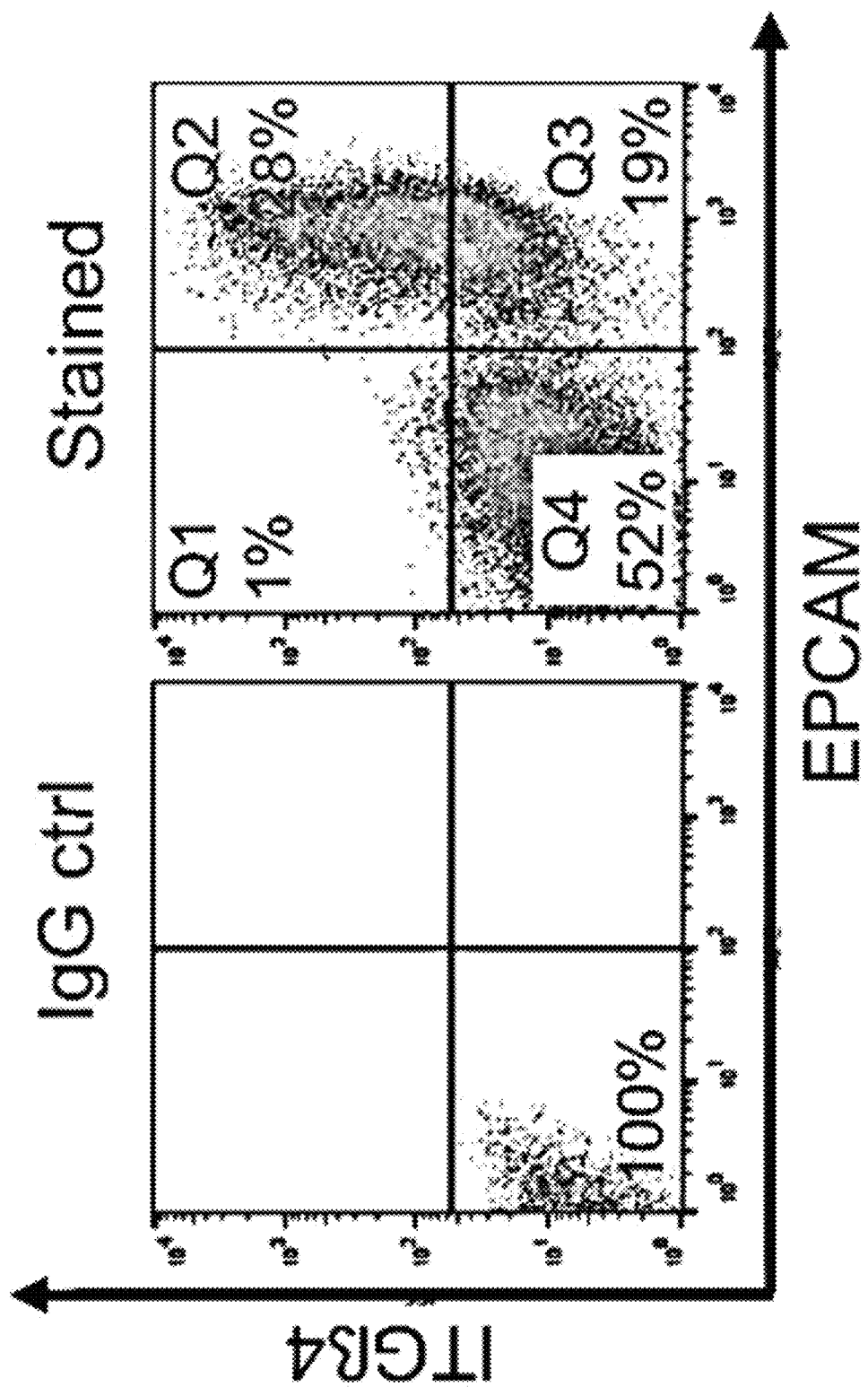
Figure 4D:
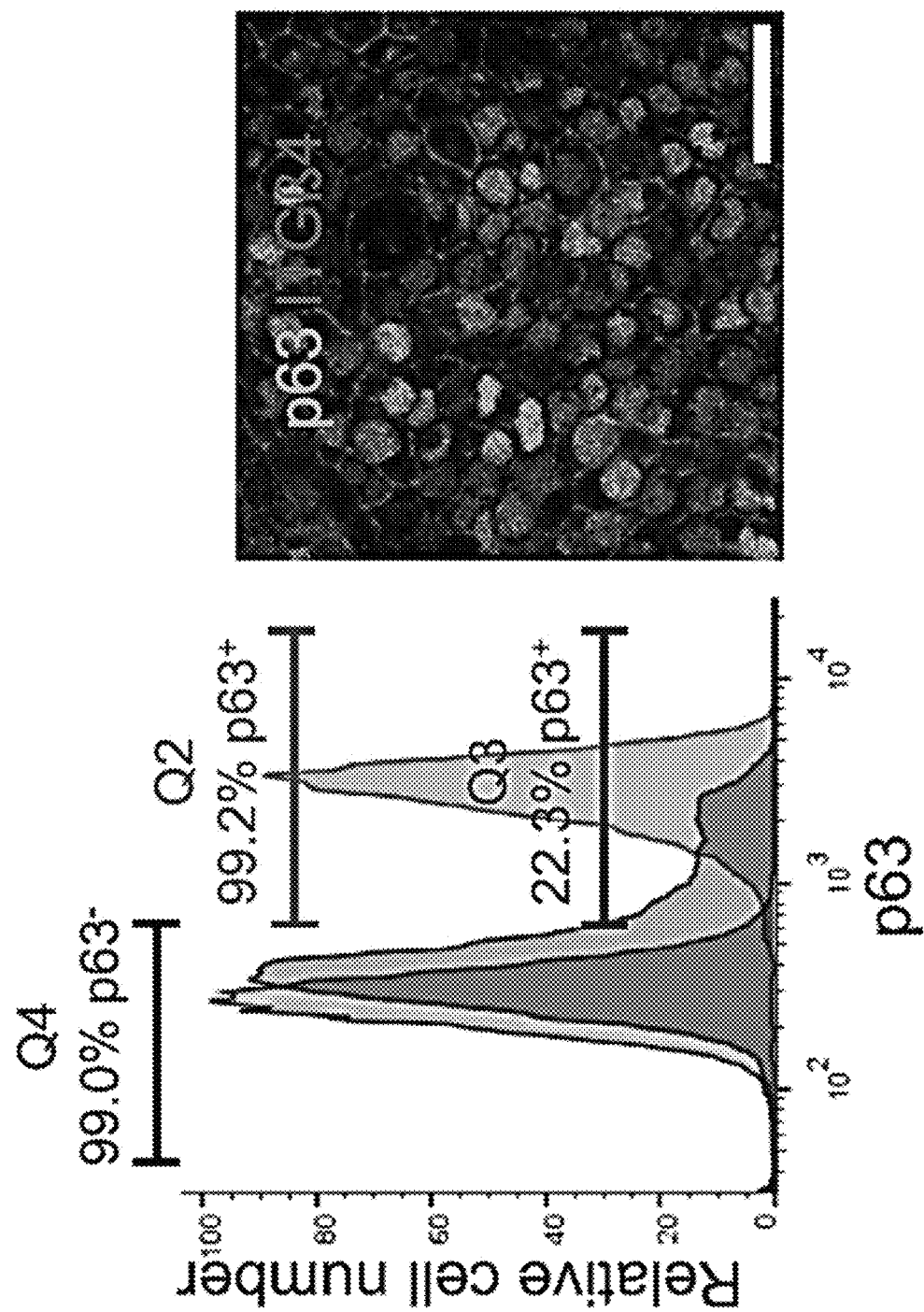
Figure 4E:
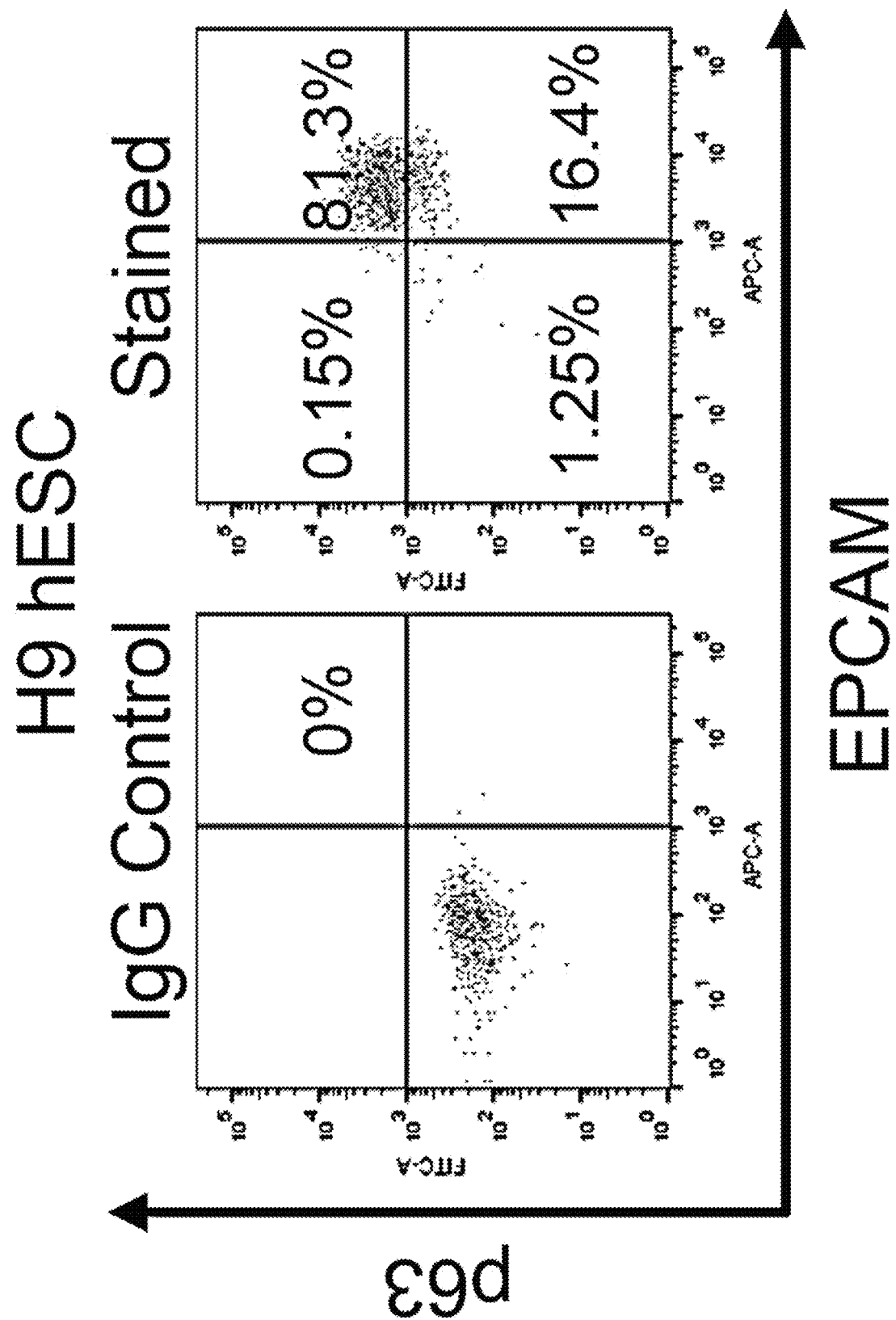
Figure 4F:
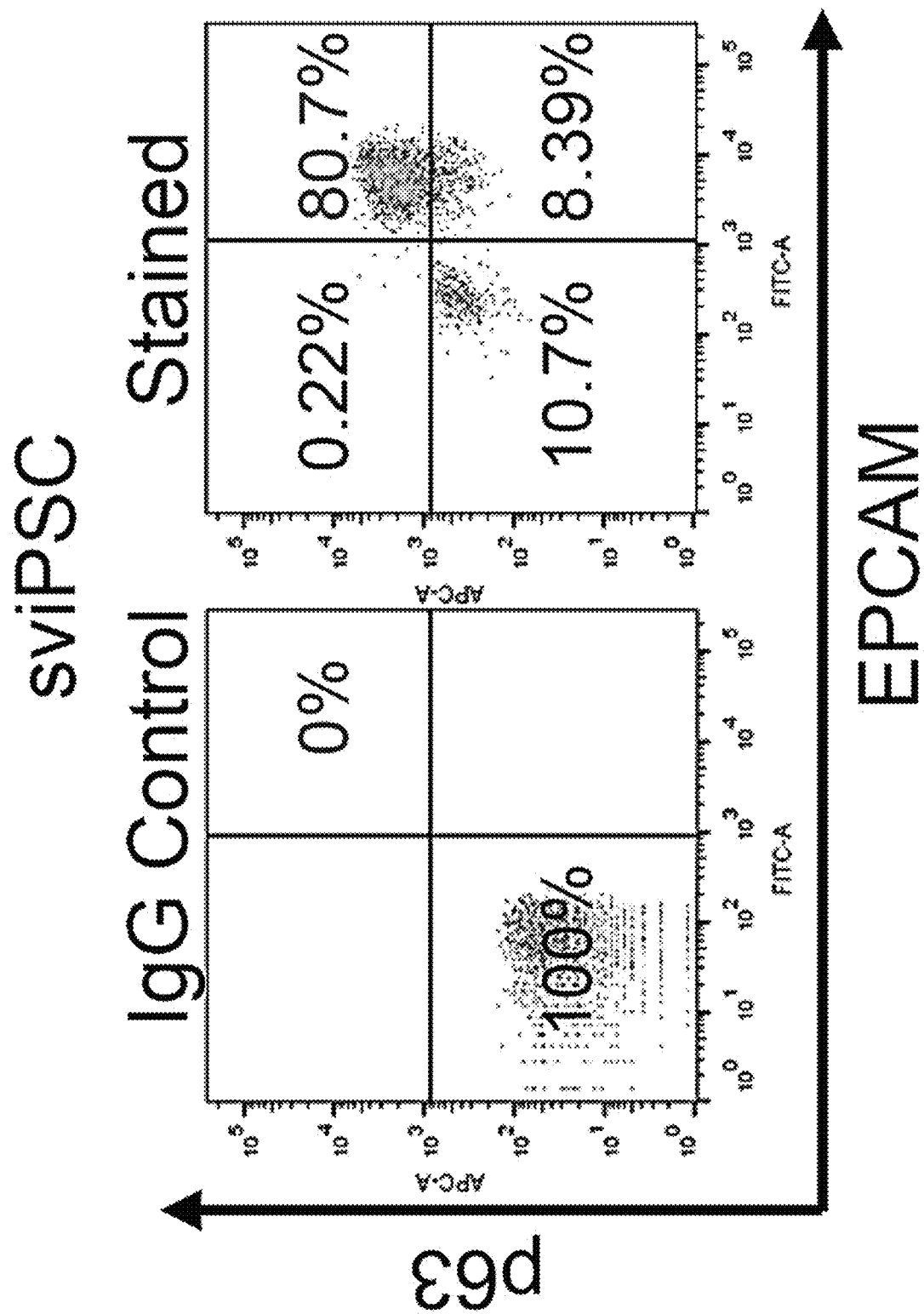
Figure 4G:
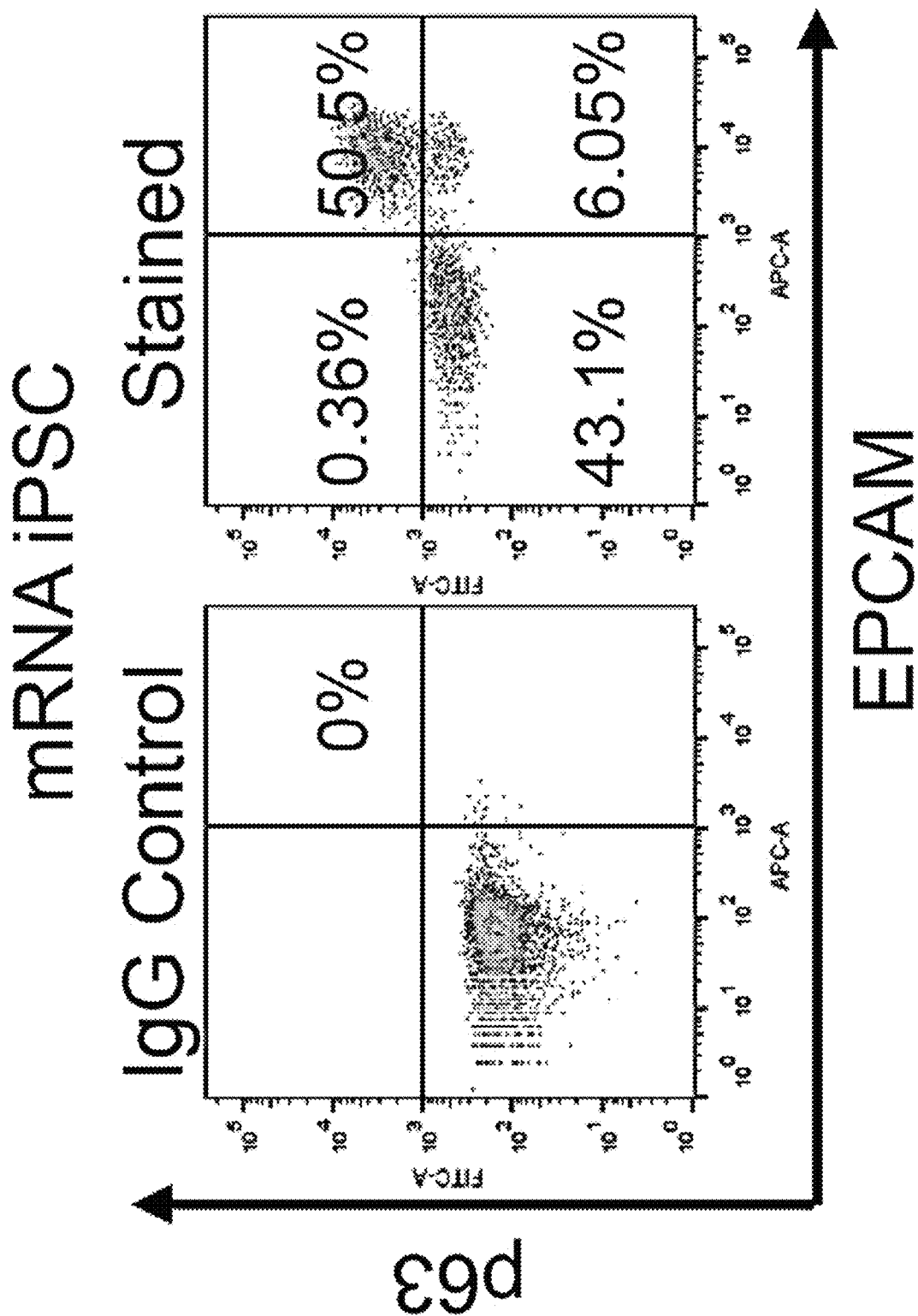
Figure 4H:
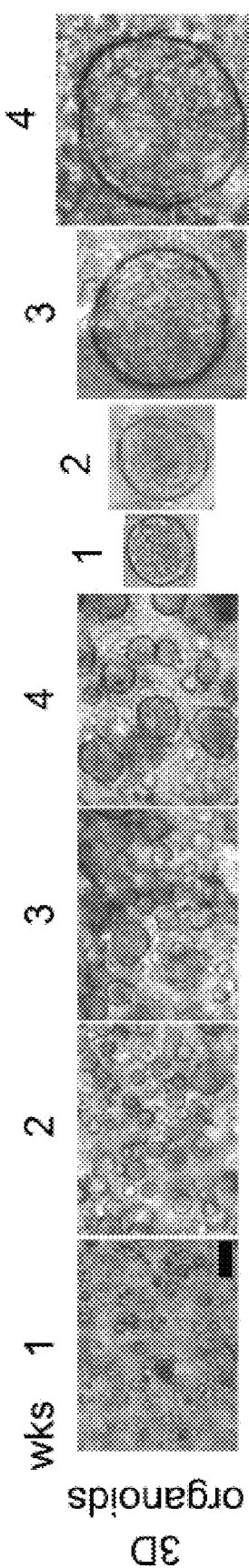

However, purification with the EPCAM magnetic beads seemed not to reach 100% efficiency and contaminated EPCAM− cells proliferated quickly after reseeding (FIG. 4D). Then EPCAM and ITGß4 were combined to further purify EPCs from the day 5 culture of EPCAM− isolated cells (FIG. 4D). Significantly, 99.2% epithelial cells purified with EPCAM and ITGß4 were also positive for p63 (FIG. 4D) while nearly all (99%) EPCAM− ITGß4-did not express p63 (FIG. 4D). There also was a small percentage of EPCAM+ ITGß4-cells which did express p63 (FIG. 4D), which is consistent with the previous finding that a small subpopulation of EPCs expressed low levels of ITGß4 in the esophagus (DeWard et al., 2014). The FACS-purified EPCs (EPCAM+ ITGß4+) were able to proliferate and form 3D organoids (FIG. 4H). Overall these findings indicated that the cell surface markers EPCAM and ITGß4 allowed purification of hESC-derived EPCs for further application.

Figure 5A:
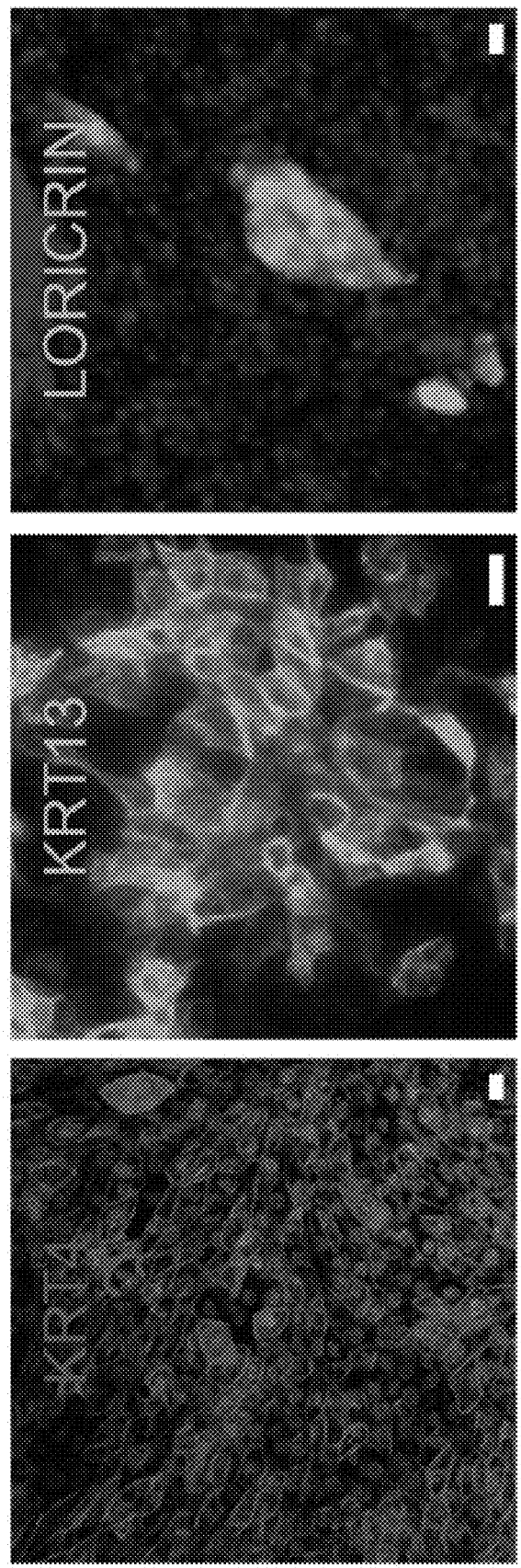
Figure 5B:
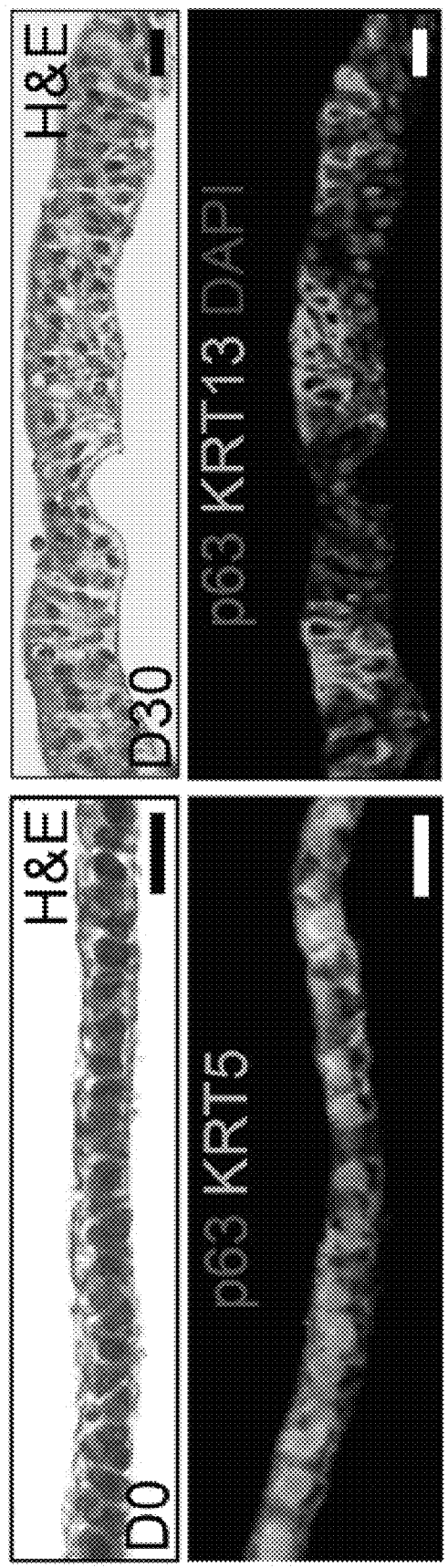
Figure 5C:
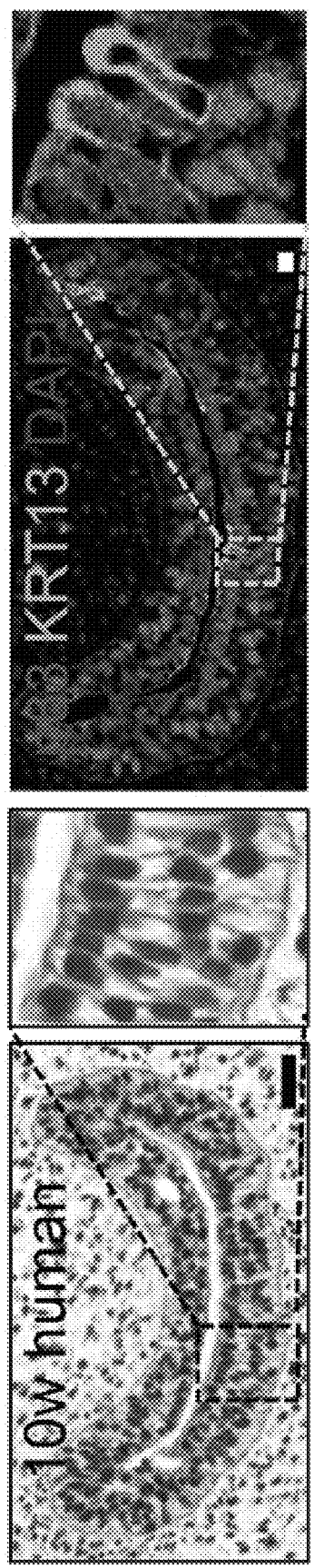

Example 5—hPSC-Derived EPCs (SOX2+p63+ NKX2.1−) were Capable of Reconstituting the Stratified Squamous Epithelium Both In Vitro and In Vivo Next, it was asked whether the hPSC-derived EPCs can undergo normal squamous differentiation. Interestingly, hESC-derived EPCs expressed the squamous differentiation proteins KRT4 and KRT13 when they were further cultured for 10 days in the medium supplemented with 5% FBS, 20 ng/ml EGF, 20 ng/ml FGF2 and 10 μM ROCK inhibitors (FIG. 5A). A very minor population of epithelial cells was observed that expressed the terminal differentiation marker LORICRIN (FIG. 5A). Consistently, LORICRIN was barely detected in the embryonic mouse and human esophagus. The nascent esophagus is initially lined by a simple layer of cells that are replaced by stratified squamous epithelia during development (Zhang et al., 2017). To test whether hPSC-derived EPCs were able to recapitulate the morphogenetic process an air-liquid interface (ALI) culture was used (Kalabis et al., 2012). The seeded EPCs initially formed a simple columnar epithelium (p63+ KRT5+) which proliferated and differentiated to form a stratified squamous epithelium composed of basal cells (p63+) and differentiating suprabasal cells (KRT13+) (FIG. 5B). The epithelium resembled the cells lining the 10-week human fetal esophagus where p63 expression was enriched in the basal layers and diminished in the suprabasal cells (KRT13+) cells (FIG. 5A).

The inventors and others previously shown that mouse esophageal progenitor cells formed organoid (esophageospheres) when cultured in Matrigel (DeWard et al., 2014; Giroux et al., 2017; Liu et al., 2013). hPSC-derived EPCs can also form 3D organoids when cultured in Matrigel (FIGS. 4H, 5D). The sphere at week 1 consisted of undifferentiated cells expressing high levels of p63 and KRT5 and low levels of KRT7 (FIG. 5D). At week 4, p63+ cells were limited to the peripheral regions of the spheres, and cells in the center expressed high levels of KRT13 (FIG. 5D). Thus hPSC-derived EPCs underwent squamous differentiation to reconstitute the stratified epithelium.

Figure 5F:
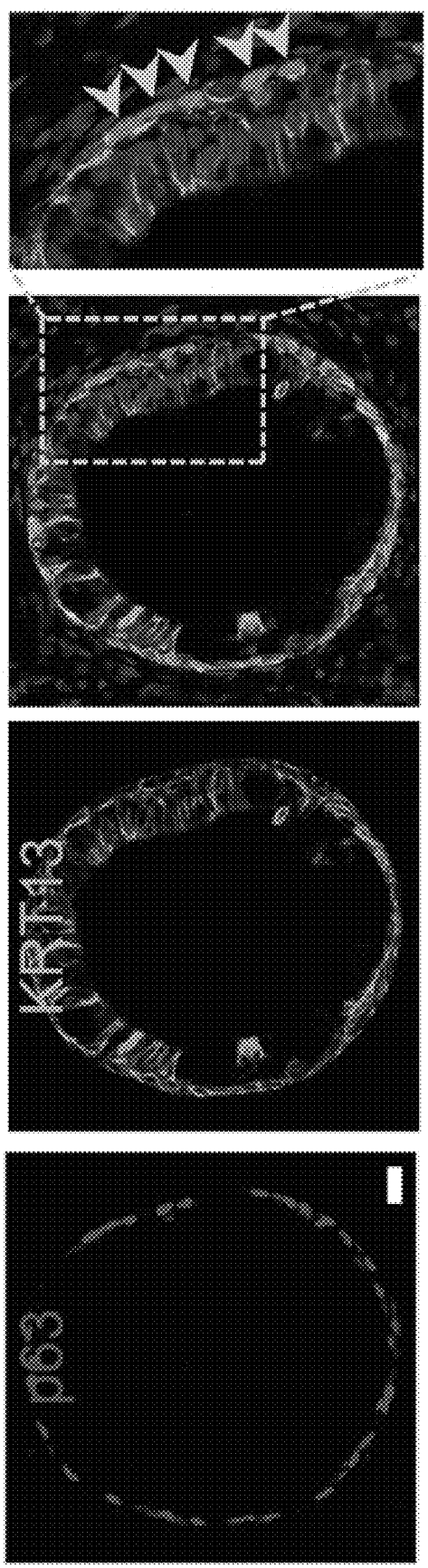

Next it was tested whether these EPCs were capable of differentiation into the stratified squamous epithelium in an in vivo setting, and Matrigel implants containing EPCs were delivered into the kidney capsule. An esophagus-like tubular structure was formed one month after implantation. The lumen was lined by the stratified epithelium with underlying p63+ cells (FIGS. 5E and 5F). Of note is that the differentiation process seemed not synchronized and unified throughout the tube which was also noticed in the developing mouse esophagus (Wang et al., 2011). While the epithelium was stratified with 2-3 layers of cells in certain parts of the tube, a large portion of the epithelium remained columnar-like (FIGS. 5E and 5F) mimicking a 10-week human fetal esophagus (FIG. 5A). Similar to ALI and organoid culture, the differentiating cells located at the top layers expressed KRT13 (FIG. 5F).

Example 6—Combined Use of hPSC Differentiation and Mouse Genetic Models Identified a Conserved Role for NOTCH Signaling in Esophageal Development The inventors have previously shown that BMP signaling activation promotes terminal differentiation of esophageal progenitors in the developing and adult esophagus (Jiang et al., 2015; Rodriguez et al., 2010). It was asked whether purified hPSCs-derived EPCs (ESC and iPSC-derived) respond to BMP activation in a similar manner. BMP4 treatment was found to significantly increase the levels of KRT13 and Involucrin (INV) (FIGS. 6A-B).

It was reasoned that the hPSC differentiation system would allow quick and efficient functional tests of candidate pathway(s) by adding chemical stimulators/inhibitors. RNA-sequencing analysis revealed that the major components (e.g., Jag1, Jag2, Notch1, Notch2, Notch3) of the NOTCH signaling pathway were enriched in hPSC-derived EPCs and human fetal esophageal epithelia. Interestingly, these components including Jag1 and Jag2 were also enriched in the epithelium of E12.5 mouse esophagus as compared to the skin. See Table 3. RNA in situ hybridization confirmed Jag1 and Jag2 expression in the E12.5 mouse esophagus and skin and E18.5 esophagus (results not shown). By contrast, Dll1, 3 and 4 were expressed at very low levels (Table 4). The expression of Notch 1 Intracellular Domain (NICD1) seemed correlated with the differentiation of esophageal progenitors. While NICD1 was not detected at E12.5, at E18.5 the expression was limited to the differentiated suprabasal cells (results not shown).

It was then tested whether NOTCH signaling is involved in the differentiation of hPSC-derived EPCs. The iPSC-derived EPCs were treated with 10 μM γ-secretase inhibitor DAPT to block NOTCH signaling. As expected, treatment with DAPT led to downregulation of HESS, HEY1 and HEY2, the downstream targets of NOTCH signaling (Kopan and Ilagan, 2009). More importantly, inhibition of NOTCH signaling led to the reduced expression of KRT13 and INV at the transcription and protein levels (FIG. 6D), supporting that NOTCH was required for the differentiation of the iPSC-derived EPCs.

It was tested whether the inhibition of NOTCH signaling affected the specification of EPCs during PSC differentiation and found that application of DAPT did not affect initial EPC commitment from the AFE (FIG. 6C). This finding is consistent with the normal specification of esophageal progenitor cells (p63+ Sox2+ NKX2.1−) in the E11.5 Shh-Cre; RBPjκloxp/loxp mouse mutants where the transcriptional regulator RBPjκ of canonical Notch signaling was ablated in the early AFE (results not shown), confirming that NOTCH signaling is not required for EPC specification from AFE in both human and mouse.

Next it was asked whether the Notch pathway has a similar role in the development of mouse esophagus. RBPj κ, the transcriptional regulator of canonical Notch signaling in the Shh-Cre; RBPj κloxp/loxp mouse mutants was deleted. Strikingly, the epithelial morphogenesis was severely disrupted, and the number of epithelial layers was decreased following the deletion of RBPj κ (FIG. 6E). In addition, deletion of RBPj κ resulted in decreased thickness of the suprabasal cells (KRT13+) (FIG. 6F). In keeping with this finding, the numbers of differentiating cells (KRT4+) were also decreased (FIG. 6G).

Next combined deletion of Jag1 and Jag2 was performed in Shh-Cre; Jag1loxp/loxp; Jag2loxp/loxp mutants. Interestingly, loss of Jag1 and Jag2 also blocked the squamous differentiation of progenitor cells in the developing esophagus (FIG. 7A), and thickness of the differentiating suprabasal layer (KRT13+ KRT4+) was significantly reduced (FIGS. 7B-C). Notably, while the impact on epithelial differentiation was apparent in the mutant esophagus lacking Jag2, epithelial differentiation was minimally affected in mutants only lacking Jag1 (FIGS. 7A-C). These findings were consistent with higher levels of Jag2 than Jag1 in E12.5 esophagus (Table 4).

Taken together, these studies suggested that hPSC differentiation and mouse genetics studies complement each other, providing an efficient platform to identify the important role of the NOTCH pathway in the morphogenesis of the esophageal epithelium.

TABLE 4

RNA Sequencing Results

| Genes | E12.5 Mouse esophagus | Skin | Human Fetal Esophagus | EPCs |
|---|---|---|---|---|
| Jag1 | 14.6 | 16.9 | 38.5 | 186.7 |
| Jag2 | 82.6 | 20.7 | 12.9 | 12.2 |
| Dll1 | 0.4 | 3.3 | 9.1 | 1.1 |
| Dll3 | 0.2 | 3.8 | 0.3 | 0.5 |
| Dll4 | 0.3 | 2 | 3.5 | 0.1 |
| Notch1 | 21.9 | 13.6 | 13.3 | 6.5 |
| Notch2 | 17.2 | 23.4 | 37.0 | 18.0 |
| Notch3 | 43.5 | 21.3 | 43.9 | 30.5 |
| Notch4 | 0.4 | 1.5 | 4.6 | 0.9 |

REFERENCES

Barbera et al., (2015). The human squamous oesophagus has widespread capacity for clonal expansion from cells at diverse stages of differentiation. *Gut* 64, 11-19.

Blank et al., (2008). An in vivo reporter of BMP signaling in organogenesis reveals targets in the developing kidney. *BMC Dev Biol* 8, 86.

Brooker et al., (2006). Notch ligands with contrasting functions: Jagged1 and Delta1 in the mouse inner ear. *Development* 133, 1277-1286.

Burke, and Oliver, (2002). Prox 1 is an early specific marker for the developing liver and pancreas in the mammalian foregut endoderm. *Mech Develop* 118, 147-155.

Chang et al., (2013). Lung epithelial branching program antagonizes alveolar differentiation. *Proc Natl Acad Sci USA* 110, 18042-18051.

Chen et al., (2017). A three-dimensional model of human lung development and disease from pluripotent stem cells. *Nat Cell Biol* 19, 542-549.

Dathan et al., (2002). Distribution of the titf2/foxe1 gene product is consistent with an important role in the development of foregut endoderm, palate, and hair. *Dev Dyn* 224, 450-456. DeWard et al., (2014). Cellular heterogeneity in the mouse esophagus implicates the presence of a nonquiescent epithelial stem cell population. *Cell Rep* 9, 701-711.

Domyan et al., (2011). Signaling through BMP receptors promotes respiratory identity in the foregut via repression of Sox2. *Development* 138, 971-981.

Giroux et al., (2017). Long-lived keratin 15+ esophageal progenitor cells contribute to homeostasis and regeneration. *J Clin Invest* 127, 2378-2391.

Goldstein et al., (2007). Overexpression of Kruppel-like factor 5 in esophageal epithelia in vivo leads to increased proliferation in basal but not suprabasal cells. *Am J Physiol Gastrointest Liver Physiol* 292, G1784-1792.

Goss et al., (2009). Wnt2/2b and beta-catenin signaling are necessary and sufficient to specify lung progenitors in the foregut. *Dev Cell* 17, 290-298.

Han et al., (2002). Inducible gene knockout of transcription factor recombination signal binding protein-J reveals its essential role in T versus B lineage decision. *Int Immunol* 14, 637-645.

Harfe et al., (2004). Evidence for an expansion-based temporal Shh gradient in specifying vertebrate digit identities. *Cell* 118, 517-528.

Harris-Johnson et al., (2009). beta-Catenin promotes respiratory progenitor identity in mouse foregut. *Proc Natl Acad Sci USA* 106, 16287-16292.

Hawkins et al., (2017). Prospective isolation of NKX2-1-expressing human lung progenitors derived from pluripotent stem cells. *J Clin Invest* 127, 2277-2294.

Huang et al., (2015). The in vitro generation of lung and airway progenitor cells from human pluripotent stem cells. *Nat Protoc* 10, 413-425.

Huang et al., (2014). Efficient generation of lung and airway epithelial cells from human pluripotent stem cells. *Nat Biotechnol* 32, 84-91.

Jacobs et al., (2012). Genetic and cellular mechanisms regulating anterior foregut and esophageal development. *Dev Biol* 369, 54-64.

Jiang et al., (2015). BMP-driven NRF2 activation in esophageal basal cell differentiation and eosinophilic esophagitis. *J Clin Invest* 125, 1557-1568.

Jiang et al., (2017). Transitional basal cells at the squamous-columnar junction generate Barrett's oesophagus. *Nature Accepted.*

Kalabis et al., (2008). A subpopulation of mouse esophageal basal cells has properties of stem cells with the capacity for self-renewal and lineage specification. *J Clin Invest* 118, 3860-3869.

Kalabis et al., (2012). Isolation and characterization of mouse and human esophageal epithelial cells in 3D organotypic culture. *Nat Protoc* 7, 235-246.

Kopan and Ilagan (2009). The canonical Notch signaling pathway: unfolding the activation mechanism. *Cell* 137, 216-233.

Liu et al., (2013). Sox2 cooperates with inflammation-mediated Stat3 activation in the malignant transformation of foregut basal progenitor cells. *Cell Stem Cell* 12, 304-315.

Longmire et al., (2012). Efficient derivation of purified lung and thyroid progenitors from embryonic stem cells. *Cell Stem Cell* 10, 398-411.

McCauley et al., (2017). Efficient Derivation of Functional Human Airway Epithelium from Pluripotent Stem Cells via Temporal Regulation of Wnt Signaling. *Cell Stem Cell* 20, 844-857 e846.

McCracken et al., (2014). Modelling human development and disease in pluripotent stem-cell-derived gastric organoids. *Nature* 516, 400-404.

McMahon et al., (1998). Noggin-mediated antagonism of BMP signaling is required for growth and patterning of the neural tube and somite. *Genes Dev* 12, 1438-1452.

Minoo et al., (1999). Defects in tracheoesophageal and lung morphogenesis in Nkx2.1(−/−) mouse embryos. *Dev Biol* 209, 60-71.

Mori et al., (2015). Notch3-Jagged signaling controls the pool of undifferentiated airway progenitors. *Development* 142, 258-267.

Mou et al., (2016). Dual SMAD Signaling Inhibition Enables Long-Term Expansion of Diverse Epithelial Basal Cells. *Cell Stem Cell* 19, 217-231.

Mou et al., (2012). Generation of multipotent lung and airway progenitors from mouse ESCs and patient-specific cystic fibrosis iPSCs. *Cell Stem Cell* 10, 385-397.

Ober et al., (2006). Mesodermal Wnt2b signaling positively regulates liver specification. *Nature* 442, 688-691.

Okano et al., (2000). The Kruppel-like transcriptional factors Zf9 and GKLF coactivate the human keratin 4 promoter and physically interact. *FEBS Lett* 473, 95-100.

Pagliuca et al., (2014). Generation of functional human pancreatic beta cells in vitro. *Cell* 159, 428-439.

Peters et al., (1998). Pax9-deficient mice lack pharyngeal pouch derivatives and teeth and exhibit craniofacial and limb abnormalities. *Genes Dev* 12, 2735-2747.

Piazzolla et al., (2014). Lineage-restricted function of the pluripotency factor NANOG in stratified epithelia. *Nat Commun* 5, 4226.

Que, (2015). The initial establishment and epithelial morphogenesis of the esophagus: a new model of tracheal-esophageal separation and transition of simple columnar into stratified squamous epithelium in the developing esophagus. Wiley Interdiscip Rev *Dev Biol* 4, 419-430.

Que et al., (2006). Morphogenesis of the trachea and esophagus: current players and new roles for noggin and Bmps. *Differentiation* 74, 422-437.

Que et al., (2009). Multiple roles for Sox2 in the developing and adult mouse trachea. *Development* 136, 1899-1907.

Que et al., (2007). Multiple dose-dependent roles for Sox2 in the patterning and differentiation of anterior foregut endoderm. *Development* 134, 2521-2531.

Rockich et al., (2013). Sox9 plays multiple roles in the lung epithelium during branching morphogenesis. *Proc Natl Acad Sci USA* 110, E4456-4464.

Rodriguez et al., (2010). BMP signaling in the development of the mouse esophagus and forestomach. *Development* 137, 4171-4176.

Roost et al., (2015). KeyGenes, a Tool to Probe Tissue Differentiation Using a Human Fetal Transcriptional Atlas. *Stem Cell Rep* 4, 1112-1124.

Shi et al., (2017). Genome Editing in hPSCs Reveals GATA6 Haploinsufficiency and a Genetic Interaction with GATA4 in Human Pancreatic Development. *Cell Stem Cell* 20, 675-688 e676. Song et al., (2014). Hippo coactivator YAP1 upregulates SOX9 and endows esophageal cancer cells with stem-like properties. *Cancer Res* 74, 4170-4182.

Spence et al., (2011). Directed differentiation of human pluripotent stem cells into intestinal tissue in vitro. *Nature* 470, 105-U120.

Trounson and DeWitt, (2016). Pluripotent stem cells progressing to the clinic. *Nat Rev Mol Cell Biol* 17, 194-200.

Tsao et al., (2016). Epithelial Notch signaling regulates lung alveolar morphogenesis and airway epithelial integrity. *Proc Natl Acad Sci USA* 113, 8242-8247.

Tetreault et al., (2016). KLF4 transcriptionally activates non-canonical WNT5A to control epithelial stratification. *Sci Rep* 6, 26130.

Wang et al., (2014). Hedgehog signaling regulates FOXA2 in esophageal embryogenesis and Barrett's metaplasia. *J Clin Invest* 124, 3767-3780.

Wang et al., (2011). Residual embryonic cells as precursors of a Barrett's-like metaplasia. *Cell* 145, 1023-1035.

Wang et al., (2006). Retinoic acid regulates morphogenesis and patterning of posterior foregut derivatives. *Dev Biol* 297, 433-445.

Wells et al., (2007). Wnt/beta-catenin signaling is required for development of the exocrine pancreas. *Bmc Developmental Biology* 7.

Wong et al., (2012). Directed differentiation of human pluripotent stem cells into mature airway epithelia expressing functional CFTR protein. *Nature Biotechnology* 30, 876-U108.

Xu et al., (2010). Generation of mice with a conditional null allele of the Jagged2 gene. *Genesis* 48, 390-393.

Yiangou et al. (2018) Human Pluripotent Stem Cell-Derived Endoderm for Modeling Development and Clinical Applications. *Cell Stem Cell* 22, 485-499.

Yu et al., (2005). Conversion of columnar to stratified squamous epithelium in the developing mouse esophagus. *Dev Biol* 284, 157-170.

Zhang et al., (2017). Development and stem cells of the esophagus. *Semin Cell Dev Biol* 66, 25-35.

The invention claimed is:

1. A method for inducing esophageal differentiation of pluripotent stem cells, comprising the steps of
   a. differentiating the pluripotent stem cells into endoderm cells by culturing the pluripotent stem cells in an endoderm differentiation medium for about one day to about four days;
   b. differentiating the endoderm cells produced from step a. into anterior foregut cells by culturing the endoderm cells in an anterior foregut differentiation medium and (i) contacting or incubating the cultured endoderm cells with Noggin and SB431542 for about 24 hours, and (ii) further contacting or incubating the cultured endoderm cells with SB431542 and IWP-2 and wherein step b(ii) does not comprise contacting or incubating the cultured endoderm cells with Noggin for about 24 hours;
   c. further culturing the anterior foregut cells produced from step b. in a first esophageal differentiation medium for about two days to ten days, wherein the first esophageal differentiation medium comprises Noggin and SB431542; and
   d. further culturing the cells produced from step c in a second esophageal progenitor cell differentiation medium under conditions and for a time sufficient to allow the cells produced by step c to differentiate into esophageal progenitor cells, wherein the esophageal progenitor cells are SOX2+p63+EPCAM+ITGβ+NKX2.1-.

2. The method of claim 1, wherein the pluripotent stem cell is derived from a mouse or a human.

3. The method of claim 1, wherein the pluripotent stem cell is chosen from the group consisting of embryonic stem cells and induced pluripotent stem cells.

4. The method of claim 1, wherein the Noggin in step b. is used in an amount ranging from about 50 ng/ml to about 200 ng/ml.

5. The method of claim 1, wherein the SB431542 in step b. is used in an amount ranging from about 1 µM to about 25 µM.

6. The method of claim 1, wherein step b. is performed starting at about day 4 to about day 5 for about 48 hours to about 72 hours.

7. The method of claim 1, wherein the IWP-2 is used in an amount ranging from about 0.5 µM to about 2 µM.

8. The method of claim 1, wherein the Noggin in step c. is used in an amount ranging from about 50 ng/ml to about 200 ng/ml.

9. The method of claim 1, wherein the SB431542 in step c. is used in an amount ranging from about 1 µM to about 25 µM.

10. The method of claim 1, wherein step c. is performed starting at about day 6 to about day 8 for about 2 days to about 10 days.

11. The method of claim 1, wherein step d. is performed for about 2 days to about 10 days.

12. The method of claim 1, wherein the endoderm differentiation medium is serum free.

13. The method of claim 1, wherein the first esophageal differentiation medium further comprises EGF and FGF10.

14. The method of claim 1, further comprising purifying the esophageal progenitor cells obtained in step d. using the cell surface markers EPCAM+ and ITGµ4+.

15. The method of claim 14, wherein antibodies for EPCAM+ and ITGµ4+ are used to purify the esophageal progenitor cells.

16. The method of claim 1, wherein step (b)(ii) takes place for about 24 hours subsequent to step b(i).

* * * * *